(12) United States Patent
Lee et al.

(10) Patent No.: US 9,844,564 B2
(45) Date of Patent: Dec. 19, 2017

(54) PVAX COPOLYMER AND PVAX MICROPARTICLES COMPRISING THE SAME

(71) Applicants: Industrial Cooperation Foundation Chonbuk National University, Jeollabuk-do (KR); Beth Israel Deaconess Medical Center, Boston, MA (US)

(72) Inventors: Dong Won Lee, Jeollabuk-do (KR); Dong Hyun Hong, Gyeonggi-do (KR); Peter M. Kang, Lexington, MA (US)

(73) Assignees: Industrial Cooperation Foundation Chonbuk University, Jeonbuk (KR); Beth Israel Deaconess Medical Center, Inc., Boston, MA (US)

( * ) Notice: Subject to any disclaimer, the term of this patent is extended or adjusted under 35 U.S.C. 154(b) by 129 days.

(21) Appl. No.: 14/432,114

(22) PCT Filed: Sep. 30, 2013

(86) PCT No.: PCT/US2013/062627
§ 371 (c)(1),
(2) Date: Mar. 27, 2015

(87) PCT Pub. No.: WO2014/052961
PCT Pub. Date: Apr. 3, 2014

(65) Prior Publication Data
US 2015/0290239 A1  Oct. 15, 2015

(30) Foreign Application Priority Data

Sep. 28, 2012 (KR) .................. 10-2012-0108696
Aug. 1, 2013 (WO) .................. PCT/KR13/06930

(51) Int. Cl.
*A61K 31/765* (2006.01)
*A61K 9/14* (2006.01)
(Continued)

(52) U.S. Cl.
CPC .............. *A61K 31/765* (2013.01); *A61K 9/14* (2013.01); *A61K 49/0093* (2013.01); *C08G 63/133* (2013.01)

(58) Field of Classification Search
CPC .... A61K 31/765; A61K 49/0093; A61K 9/14; C08G 63/133
See application file for complete search history.

(56) References Cited

FOREIGN PATENT DOCUMENTS

KR  10-2011-0124168 A  11/2011
WO  WO2011142504 A1  11/2011

OTHER PUBLICATIONS

Klein et al, ed., Organ Transplantation: A Clinical Guide, Cambridge University Press, 2011, pp. 231-233.*

(Continued)

*Primary Examiner* — Rachael E Bredefeld
(74) *Attorney, Agent, or Firm* — Melissa Hunter-Ensor; Elbert Chiang; Greenberg Traurig, LLP

(57) ABSTRACT

The present invention includes a vanillyl alcohol-containing copolyoxalate copolymer (PVAX). The present invention also includes a PVAX microparticle comprising PVAX. In one aspect, the compositions of the invention can be used as a drug delivery system, an antioxidant or anti-inflammatory composition, a composition for preventing or treating ischemic disease, a composition for inhibiting the side effects of anticancer drugs, a contrast agent, and/or a composition for diagnosing ischemic disease.

7 Claims, 36 Drawing Sheets

(51) Int. Cl.
  *A61K 49/00* (2006.01)
  *C08G 63/133* (2006.01)

(56) References Cited

OTHER PUBLICATIONS

International Search Report and Written Opinion for corresponding PCT/US2013/062627 application, dated Jan. 8, 2014 (5 pages).
International Preliminary Report on Patentability for corresponding PCT/US2013/062627 application, dated Mar. 31, 2015(10 pages).
International Search Report and Written Opinion for corresponding PCT/KR2010/005522 application, dated Jun. 29, 2011 (12 pages).
Lee, Dongwon et al., "H2O2-responsive molecularly engineered polymer nanoparticles as ischemia/reperfusion-targeted nanotherapeutic agents," Scientific reports 2013, vol. 3, Article No. 2233, See abstract results: discussion (2013).
Lee, Eunyong et al., "A biodegradable and biocompatible drug-delivery system based on polyoxalate microparticles," Journal of Biomaterials Science, vol. 22, No. 13, pp. 1683-1694, See abstract: p. 1692, Scheme 1 (2011).
Kim, Soojin et al., "Reduction of oxidative stress by p-hydroxybenzyl alcohol-containing biodegradable polyoxalate nanoparticulate antioxidant," Biomaterials, vol. 32, No. 11, pp. 3021-3029, See abstract: pp. 3027-3028, Scheme 1 (2011).
Park, Hyunjin et al., "Antioxidant and anti-inflammatory activities of hydroxybenzyl alcohol releasing biodegradable polyoxalate nanoparticles," Biomacromolecules, vol. 11, No. 8, pp. 2103-2108, See abstract: p. 2108, Scheme 1 (2010).

\* cited by examiner

| Number of value | 4 | 4 | 5 | 8 |
|---|---|---|---|---|
| Mean | 1 | 1.23 | 3.7 | 1.84 |
| SEM | 0.06218 | 0.1063 | 0.5423 | 0.09343 |

| Number of value | 4 | 6 | 8 | 12 |
|---|---|---|---|---|
| Mean | 1 | 1.152 | 3.805 | 1.726 |
| SEM | 0.1294 | 0.05886 | 0.5177 | 0.3564 |

PBS     Porous PLGA Microparticles     Porous PVAX Microparticles

PVAX COPOLYMER AND PVAX MICROPARTICLES COMPRISING THE SAME

STATEMENT OF RIGHTS TO INVENTIONS MADE UNDER FEDERALLY SPONSORED RESEARCH

This work was supported by the following grant from the National Institutes of Health, Grant No: RO1 HL091998. The government has certain rights in the invention.

CROSS-REFERENCE TO RELATED APPLICATIONS

The present application is the 35 U.S.C. §371 national phase application pursuant to 35 U.S.C. §371, of PCT International Application No. PCT/US2013/062627, filed Sep. 30, 2013, designating the United States and published in English, which claims priority to International Application No. PCT/KR2013/006930, filed Aug. 1, 2013, and published under PCT Article 21(2) in English, which claims priority to Korean Application No. 10-2012-0108696, filed Sep. 28, 2012, all of which applications are hereby incorporated by reference in their entireties herein.

BACKGROUND OF THE INVENTION

Several biodegradable polymers have found use in the field of tissue engineering, because of their attractive physical, chemical, biological and mechanical properties. Polymers useful in tissue engineering may be divided into the groups of natural polymers and synthetic polymers.

Natural polymers include, but are not limited to, collagen, hyaluronic acid, alginate, gelatin, xanthan gum, keratin, and small intestinal submucosa. These polymers have good biocompatibility and are unlikely to induce an immune response after transplantation. However, the mechanical properties of natural polymers are not completely satisfactory.

Synthetic polymers include, but are not limited to, PLA (poly(lactic acid)), PGA (poly(glycolic acid)), PLGA (poly(lactic-co-glycolic acid)) and PCL (poly(ε-caprolactone)) and are mainly hydrophobic polyesters. Among them, PGA and PLA (both of which are comprised of α-hydroxy acid monomers) and their copolymer PLGA are synthetic polymers approved by the U.S. FDA for biomedical applications. PGA, PLA and PLGA are widely used as porous tissue scaffolds and drug delivery systems, and have high biocompatibility, biodegradability and processability. However, these synthetic polymers do not adhere well to cells, because they lack biologically active components and are hydrophobic. Acids produced during the hydrolysis of PLGA reduce the pH of the surrounding tissue, causing inflammation. Further, these polymers are incapable of targeting a specific site or responding to the environment of a diseased site.

Vanillyl alcohol (also known as 4-(hydroxymethyl)-2-methoxyphenol; 3-methoxy-4-hydroxybenzyl alcohol; 4-hydroxy-3-methoxybenzenemethanol; 4-hydroxy-3-methoxybenzyl alcohol; vanillic alcohol; vanillin alcohol; or "VA"), a phenolic compound found in plant roots, tomatoes and carrots, and is the main component of *Gastrodia elata*, used to treat headaches and cancer in traditional Chinese medicine. In recent years, the medicinal effects and properties of natural vanillyl alcohol and vanillyl derivatives have been studied.

Oxidative stress has been shown to be involved in the development of many disease states including cancer, neurodegenerative disease, transplantation, end stage renal disease and atherosclerosis/heart failure. Oxidative stress injury occurs when there is an increased production of oxidizing species simultaneously with a reduction in antioxidant defenses resulting in the manifestation of reactive oxygen species (ROS). Reperfusion of a previously ischemic tissue is a prominent disease pathway in the development of a large amount of ROS. This overwhelms the cellular defense system and subsequently damages normal cellular functions that can ultimately lead to death. In particular, hydrogen peroxide ($H_2O_2$), the most abundant form of the ROS produced during ischemia/reperfusion (I/R), plays an important role by inducing the release of pro-inflammatory cytokines and apoptosis which further potentiate tissue damage. Since the amount of tissue damage is the most important determinant of morbidity and mortality associated with ischemic diseases, limiting cellular death is a paramount approach for favorable outcome in these conditions. Excess amount of $H_2O_2$ that exceeds local antioxidant capacity determines the susceptibility for oxidative damage. Therefore, focusing locally on $H_2O_2$ production is a therapeutically relevant way that could stop oxidative stress injury in a variety of disease pathologies.

Oxidative stress plays a major role in cardiac dysfunction leading to a variety of ailments including heart failure thereby resulting in the need of major surgery. In 2011 nearly 11% of US adults had been diagnosed with cardiovascular disease, where more than 50% will also experience co-morbidities such as hypertension and stroke. Although cardiovascular disease has diverse etiology, the primary induction of disease onset is atherosclerosis, the occlusion of primary vessels that carry blood supply to and from the heart. As the disease progresses there will be continued blockage of the arteries leading to necessary procedures such as cardiopulmonary bypass surgery (CPB) or coronary artery bypass graft (CABG) whereby new vessels are either diverted or created in order to bypass those already occluded with plaque allowing for improved circulation. Nearly 2% of US adults, or 395,000 individuals, require a CABG procedure annually in order to forgo life-threatening events such as cardiac arrest.

CABG is a major surgical procedure that requires lengthy hospital stays and likely results in post-operative ischemia or reperfusion-related complications. Complications associated with oxidative damage during CABG (with respective % incidence) include, but are not limited to, atrial fibrillation (up to 40%), infarct extension: reocclusion of an infarct-related artery (IRA) (5-30%), recurrent infarction (17-25%), arrhythmia (13.6%), renal function decrease (5-10%), stroke (6.1%), small-to-moderate MI (2-4%), ventricular tachycardia/fibrillation (2-3%), congestive heart failure (2.4%), GI dysfunction (2.3%), and acute renal failure (0.7%).

Nearly 15% of those patients develop perioperative complications, specifically ischemia and/or reperfusion injury, adding at least an additional $10,000 per patient. Adding insult to injury, one of the main pathogenic mechanisms following CABG surgery is subsequent ischemia/reperfusion (I/R) injury, which can appear as reocclusion of an infarct-related artery (IRA). Approximately 5-30% of patients experience infarct extension and 17-25% of patients likely experience early IRA. Patients who experience I/R can also clinically present symptoms that include arrhythmias (13.6%) combined with myocardial and microvascular stunning, and hemorrhage (5.6%) often being indistinguishable from the initial injury. Moreover, myocardial necrosis, a clear result of I/R, has been present in a majority of CPB patients with fatal outcome.

There is a need in the art to develop novel biodegradable polymers that are useful in tissue engineering and other biomedical applications. Such polymers should display good mechanical properties and biocompatibility.

SUMMARY OF THE INVENTION

As described below, the present invention generally features vanillyl alcohol-containing copolyoxalate copolymers, compositions containing these copolymers, and methods of using these compositions as anti-oxidative agents.

In one aspect, the invention includes a copolymer containing 2-(4-hydroxymethyl)-2-methoxy phenoxy)-2-oxoacetic acid (VAOX) as a monomer.

In another aspect, the invention provides a microparticle containing a copolymer, where the copolymer contains VAOX as a monomer, where the copolymer undergoes at least partial degradation to release vanillyl alcohol within the body of a subject.

In still another aspect, the invention further provides a drug delivery system containing a microparticle of the invention.

In yet another aspect, the invention further provides a pharmaceutical composition containing a microparticle of the invention as an active ingredient, where the composition further contains at least one pharmaceutically acceptable carrier, where the composition treats or prevents an oxidative-related disease, an inflammatory disease, an ischemic disease, or a side effect of an anticancer agent.

In still another aspect, the invention provides compositions for ameliorating hypoxia or ischemia associated with organ transplantation, a complication or condition associated with organ preservation.

In yet another aspect, the invention further provides a method of treating or preventing a disease or condition in a subject in need thereof, wherein the method involves administering to the subject a therapeutically effective amount of a pharmaceutically acceptable composition containing a microparticle as an active ingredient, where the microparticle contains a copolymer containing 2-(4-hydroxymethyl)-2-methoxy-phenoxy)-2-oxoacetic acid as a monomer, where the copolymer undergoes at least partial degradation to release vanillyl alcohol within the body of the subject.

In yet another aspect, the invention further provides a method of inhibiting or preventing the formation of reactive oxygen species (ROS) in at least one bodily site of a subject, where the method involves administering to the subject a therapeutically effective amount of a pharmaceutically acceptable composition containing a microparticle as an active ingredient, where the microparticle contains a copolymer containing 2-(4-hydroxymethyl)-2-methoxy-phenoxy)-2-oxoacetic acid as a monomer, where the copolymer undergoes at least partial degradation to release vanillyl alcohol within the body of the subject, and, whereby the formation of ROS in at least one bodily site of the subject is inhibited or prevented.

In still another aspect, the invention provides a method of detecting or diagnosing a state associated with formation or accumulation of ROS in at least one bodily site of a subject, where the method comprises administering to the subject a pharmaceutically acceptable composition comprising a microparticle as an active ingredient, wherein the microparticle comprises a copolymer comprising 2-(4-hydroxymethyl)-2-methoxy-phenoxy)-2-oxoacetic acid as a monomer, wherein the copolymer undergoes at least partial degradation to release vanillyl alcohol within the body of the subject, and, wherein the method further comprises administering to the subject at least one bio-imaging agent selected from the group consisting of a fluorescent agent, a far infrared-emitting agent, a radiation tracer, a PET tracer agent and a MRI contrast agent, whereby the state associated with formation or accumulation of ROS in at least one bodily site of the subject is detected or diagnosed.

In yet another aspect, the invention provides a method for reducing ischemic damage or reperfusion injury in a tissue or organ for transplantation, the method involving contacting the tissue or organ (e.g., a cardiac tissue, heart, kidney tissue, kidney, hepatic tissue, liver, lung tissue, lung, pancreatic tissue, pancreas, intestine tissue, intestine, thymus, bone, cartilage, muscular tissue, tendon, cornea, epithelial tissue, skin, cardiac valve, neurons, nerves, endothelial tissue, artery, or vein) with the pharmaceutical composition of any previous aspect before, during or after transplantation, thereby reducing ischemic damage or reperfusion injury in said tissue or organ.

In various embodiments of any of the above aspects or any other aspect of the invention delineated herein, the copolymer undergoes at least partial degradation to release vanillyl alcohol within the body of a subject. In certain embodiments of any of the above aspects, the subject is human. In other embodiments of any of the above aspects, VAOX is bound through ester bonds to other monomers within the copolymer. In certain embodiments of any of the above aspects, the copolymer further contains 1,4-cyclohexanedimethanol (CHD) as a monomer. In other embodiments of any of the above aspects, the copolymer further contains 2-((4-(hydroxymethyl)cyclohexyl)methoxy)-2-oxoacetic acid (CHDOX) as a monomer. In certain embodiments of any of the above aspects, the copolymer is represented by Formula (I):

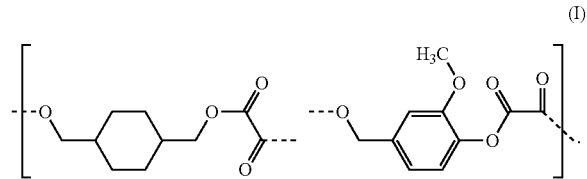

In other embodiments of any of the above aspects, in (I) the number of CHDOX monomers is an integer ranging from 10 to 50, and the number of VAOX monomers is an integer ranging from 5 to 30. In certain embodiments of any of the above aspects, in (I) the molar ratio of CHDOX to VAOX ranges from about 4:1 to about 2:3. In other embodiments of any of the above aspects, in (I) the molar ratio of CHDOX to VAOX is about 2:3. In certain embodiments of any of the above aspects, the average molecular weight of (I) is about 10,000-20,000 Dalton.

In various embodiments of any of the above aspects or any other aspect of the invention delineated herein, the microparticle has an average diameter ranging from about 200 nm to about 20 μm (e.g., 200, 300, 400, 500, 750, 1000 nm, or 1, 5, 10, 15, or 20 μm). In certain embodiments of any of the above aspects, at least one agent is encapsulated within the microparticle or chemically bound to the microparticle. In other embodiments of any of the above aspects, the at least one agent is selected from the group consisting of a therapeutic agent, a bio-imaging agent and combinations thereof. In certain embodiments of any of the above aspects, the therapeutic agent is at least one agent selected from the group consisting of an anti-oxidative agent, an anti-inflammatory agent, an anti-apoptotic agent and a thrombolytic agent. In other embodiments of any of the above aspects, the bio-imaging agent is any one or more of a fluorescent agent, a far infrared-emitting agent, a radiation tracer, a PET tracer agent and an MRI contrast agent. In certain embodiments of any of the above aspects, the fluorescent agent is any one or more of rubrene, pentacene, indocyanine green and salts thereof. In other embodiments of any of the above aspects, the far infrared-emitting agent is any one or more of HgTe nanocrystals, PbSe nanocrystals and PbS nanocrystals. In certain embodiments of any of the above aspects, the radiation tracer is any one or more of technetium-99m, molybdenum-99, thallium-201, strontium-82, and salts thereof. In other embodiments of any of the above aspects, the PET tracer agent is a any one or more of compounds labeled with $^{11}C$, $^{15}N$, $^{15}O$, $^{18}F$ and $^{82}Rb$ isotopes, and salts thereof. In certain embodiments of any of the above aspects, the MRI contrast agent is any one or more of $Fe_2O_3$, $Fe_3O_4$, iron platinum, manganese, and salts thereof.

In various embodiments of any of the above aspects or any other aspect of the invention delineated herein, the disease or condition is any one or more of an oxidative-related disease, an inflammatory disease, an ischemic disease, a complication or condition associated with solid organ transplantation, a complication or condition associated with solid organ preservation, and a side effect of a anticancer agent, where the disease or condition is treated or prevented. In other embodiments of any of the above aspects, the ischemic disease is any one or more of atherosclerosis, asthma, brain ischemia, heart ischemia, diabetic cardiovascular diseases, heart failure, myocardial hypertrophy, retinal ischemia, ischemic colitis, critical limb ischemia, ischemic acute renal failure, stroke, brain trauma, Alzheimer's disease, Parkinson's disease, fetal hypoxia, glaucoma, diabetic neuropathy, and ischemia/reperfusion injury. In certain embodiments of any of the above aspects, the anticancer drug is any one or more of doxorubicin, adriamycin, cisplatin, taxol, 5-fluorouracil and salts thereof. In other embodiments of any of the above aspects, the side effect of the anticancer drug is any one or more of cardiomuscular dysfunction, heart dysfunction, shock, pancytopenia, anemia, leucopenia, neutropenia, thrombocytopenia, bleeding, fever, chill, urticaria, liver dysfunction, proteinruia, loss of appetite, vomiting, nausea, mucositis, stomatitis, esophagitis, diarrhea, and headache. In certain embodiments of any of the above aspects, the ROS comprises a superoxide or peroxide species. In other embodiments of any of the above aspects, the composition and the at least one bio-imaging agent are co-administered to the subject. In certain embodiments of any of the above aspects, the composition and the at least one bio-imaging agent are coformulated.

The invention provides vanillyl alcohol-containing copolyoxalate copolymers and methods of using such compositions as anti-oxidants. Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIG. 12, comprising

FIG. 36, comprising FIG. 36A: representative SEM image, FIG. 36B: representative dynamic light scattering.

FIG. 43, comprising FIG. 43A: ALT activity, FIG. 43B: H&E staining, FIG. 43C: TUNEL staining.

FIG. 44, comprising

FIG. 50, comprising

FIG. 52, comprising FIG. 52A: Quantification of caspase-3 activities. FIG. 52B: Quantification of PARP-1 activity. *, P<0.05 vs. Saline I/R; †, P<0.05 vs same dose of HPOX IR group, N=4/each group.

FIG. 53, comprising FIG. 53A: Image of mRNA expression of tumor necrosis factor (TNF)-α and monocyte chemotactic protein-1 (MCP-1). S=Saline, H=HPOX, P=PVAX. FIG. 53B: Quantification of mRNA expression of TNF-α. FIG. 53C: Quantification of mRNA expression of MCP-1. *, P<0.05 vs Saline I/R; †, P<0.05 vs same dose of HPOX IR group, N=4/each group.

FIG. 54, comprising FIG. 54A: Quantification of caspase-3 activities. FIG. 54B: Quantification of PARP-1 activity. *, P<0.05 vs saline IR group, S=Saline, P20=PVAX20, P60=PVAX60, N=3-4/each group.

DETAILED DESCRIPTION OF THE INVENTION

Figure 1:
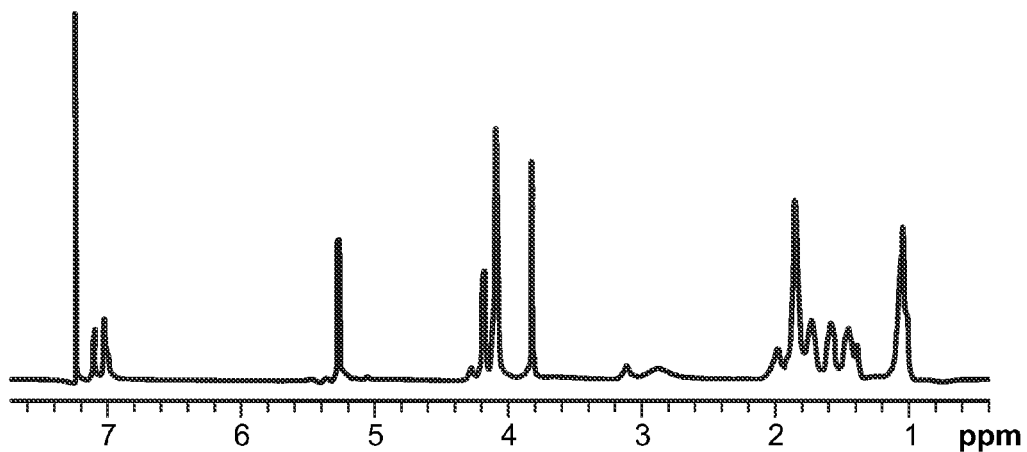
FIG. 1 illustrates the $^1H$ NMR spectrum of a vanillyl alcohol-containing copolyoxalate copolymer (or PVAX).

The present invention relates to the unexpected discovery of novel vanillyl alcohol-containing copolyoxalate copolymers (also known as PVAX). The present invention further relates to the unexpected discovery of a PVAX microparticle comprising a PVAX copolymer. In one embodiment, the compositions of the invention are useful as drug delivery systems or contrast agents. In one embodiment, the compositions of the invention are useful in diagnosing, treating and/or preventing oxidative-related diseases, inflammation, ischemic disease and side effects of anticancer drugs.

In one embodiment, the copolymer of the invention comprises vanillyl alcohol (also known as 4-hydroxymethyl-2-methoxy-phenol, 4-hydroxy-3-methoxybenzyl alcohol or VA) as a monomer (or building block). In another embodiment, the copolymer of the invention comprises oxalic acid, 1,4-cyclohexamethanol and vanillyl alcohol as monomers (or building blocks).

In one aspect, the copolymers of the invention are non-toxic, are biocompatible and are degraded under physiological conditions while releasing vanillyl alcohol. Without wishing to be limited by theory, the release of vanillyl alcohol or a derivative thereof by degradation of the copolymer of the invention accounts at least in part for the anti-oxidative, anti-inflammatory and anti-apoptotic effects of the copolymer; the preventive or ameliorative effect on side effects of anticancer drugs (such as hepatic or cardiac abnormalities) by the copolymer; and the copolymer's ability to detect hydrogen peroxide in vivo.

The microparticles of the invention are useful to prepare drug delivery systems and antioxidant or anti-inflammatory compositions. Further, the microparticles of the invention inhibit side effects of anticancer drugs (such as hepatic or cardiac abnormalities), and are thus useful in treating or preventing side effects of anticancer drugs. Further, the microparticles of the invention specifically detect hydrogen peroxide in vivo, and thus are useful as contrast agents or as diagnostic tools for ischemic disease.

Definitions

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

By "disease" is meant any condition or disorder that damages or interferes with the normal function of a cell, tissue, or organ. Examples of diseases include ischemic diseases (such as asthma, atherosclerosis, brain ischemia, heart ischemia, diabetic cardiovascular diseases, heart failure, myocardial hypertrophy, retinal ischemia, ischemic colitis, critical limb ischemia, ischemic acute renal failure, stroke, brain trauma, Alzheimer's disease, Parkinson's disease, fetal hypoxia, glaucoma, diabetic neuropathy, ischemia/reperfusion injury or ischemia/reperfusion injury complications). "Disease" also refers to ischemia/reperfusion injury associated with cardiopulmonary bypass (CPB) surgery, wherein CPB surgery includes coronary arterial bypass graft (CABG) surgery; valve, defect or aneurysm repair; heart and/or lung transplantation; pulmonary thrombectomy; or pulmonary thromboendarterectomy. "Disease" also refers to ischemia/reperfusion injury complications associated with CPB (and/or CABG) surgery, such as atrial fibrillation, infarct extension, with reocclusion of an infarct-related artery (IRA), recurrent infarction, arrhythmia, renal function decrease, stroke, small-to-moderate MI, ventricular tachycardia/fibrillation, congestive heart failure, GI dysfunction and acute renal failure. "Disease" also refers to any side effect of anticancer drugs, such as cardiomuscular dysfunctions (such as electrocardiogram abnormality, tachycardia, arrhythmia and chest pain), heart dysfunction, shock, pancytopenia, anemia, leucopenia, neutropenia, thrombocytopenia, bleeding, fever, chill, urticaria, liver dysfunction, proteinruia, loss of appetite, vomiting, nausea, mucositis, stomatitis, esophagitis, diarrhea, or headache. "Disease" also refers to any complication or condition associated with solid organ transplantation (such as liver, kidney, lung or heart) or solid organ preservation (such as liver, kidney, lung or heart).

As used herein, the term "microparticle" refers to a particle with an average diameter ranging from about 10 nm to 1,000 µm. In one embodiment, the average diameter of the particle ranges from about 100 nm to 100 µm. In another embodiment, the average diameter of the particle ranges from about 100 nm to 10 µm. In yet another embodiment, the average diameter of the particle ranges from about 200 nm to 1 µm. In yet another embodiment, the average diameter of the particle ranges from about 200 nm to 800 nm. In yet another embodiment, the average diameter of the particle is about 500 nm. In yet another embodiment, the particle is approximately spherical.

As used herein, the term "ROS" refers to reactive oxygen species. ROS are chemically reactive molecules containing oxygen, and include oxygen ions, superoxides and peroxides.

As used herein, the term "PVAX" refers to a vanillyl alcohol-containing copolyoxalate copolymer or a salt thereof. As used herein, the term "VA" refers to vanillyl alcohol; 4-(hydroxymethyl)-2-methoxyphenol; 3-methoxy-4-hydroxybenzyl alcohol; 4-hydroxy-3-methoxybenzenemethanol; 4-hydroxy-3-methoxybenzyl alcohol; vanillic alcohol; or vanillin alcohol. As used herein, the term "VAOX" refers to 2-(4-(hydroxymethyl)-2-methoxyphenoxy)-2-oxoacetic acid or a salt thereof. As used herein, the term "CHD" refers to 1,4-cyclohexanedimethanol (CHD) or a salt thereof. As used herein, the term "CHDOX" refers to 2-((4-(hydroxymethyl)cyclohexyl)methoxy)-2-oxoacetic acid or a salt thereof. As used herein, the term "HBA" refers to p-hydroxy-benzyl alcohol or a salt thereof.

As used herein, the term "PLA" refers to poly(lactic acid) or a salt thereof. As used herein, the term "PGA" refers to poly(glycolic acid) or a salt thereof. As used herein, the term "PLGA" refers to poly(lactic-co-glycolic acid) or a salt thereof. As used herein, the term "PCL" refers to poly(ε-caprolactone) or a salt thereof.

As used herein, the term "THF" refers to tetrahydrofuran. As used herein, the term "DCM" refers to dichloromethane. As used herein, the term "DMSO" refers to dimethylsulfoxide.

As used herein, the term "MTT" refers to 3-(4,5-dimethylthiazol-2-yl)-2,5-diphenyltetrazolium bromide. As used herein, the term "PMA" refers to phorbol-12-myristate-13-acetate. As used herein, the term "DCFH-DA" refers to dichlorofluorescin-diacetate. As used herein, the term "DCF" refers to dichlorodihydrofluorescein. As used herein, the term "LPS" refers to lipopolysaccharide. As used herein, the term "iNOS" refers to inducible nitric oxide synthase. As used herein, the term "COX-2" refers to cyclooxygenase-2. As used herein, the term "I/R" refers to ischemia/reperfusion. As used herein, the term "PARP-1." refers to polyADP ribose polymerase-1. As used herein, the term "TNF-α" refers to tumor necrosis factor-alpha. As used herein, the term "MCP-1" refers to monocyte chemotactic protein-1. As used herein, the term "SOD" refers to superoxide dismutase. As used herein, the term "DOX" refers to doxorubicin or a salt thereof. As used herein, the term "MnP" refers to manganese porphyrin. As used herein, the term "APAP" refers to acetaminophen or a salt thereof. As used herein, the term "TUNEL" refers to Terminal deoxynucleotidyl transferase dUTP nick end labeling. As used herein, the term "OVA" refers to ovalbumin. As used herein, the term Dex" refers to dexamethasone.

As used herein, the term "CABG" refers to coronary arterial bypass graft. As used herein, the term "CPB" refers to cardiopulmonary bypass.

The term "monomer" or "building block" refers to any discreet chemical compound of any molecular weight. A monomer or building block may comprise two or more smaller monomers connected through chemical bonds, for example.

As used herein, the term "polymer" refers to a molecule composed of repeating structural units (or monomers) typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In one embodiment, polymerization or crosslinking of at least one functional group results in about 100% consumption of the at least one functional group. In another embodiment, polymerization or crosslinking of at least one functional group results in less than about 100% consumption of the at least one functional group. Polymerization reactions comprise, for example, ether formation, thioether formation, thioester formation, ester formation and amide formation.

A "heteropolymer" or "copolymer" is a polymer derived from two or more monomeric species (or monomers or building blocks), as opposed to a homopolymer where only one monomer is used. Copolymerization refers to methods used to chemically synthesize a copolymer. Copolymers vary depending on the different types and arrangement of monomers. For example, in a copolymer consisting of two different types of monomers, the copolymers may be alternating (wherein the two different types of monomers alternate on the copolymer), periodic (wherein a specific sequence of the two types of monomers repeats itself throughout the copolymer), statistical (wherein the sequence of monomers follows a statistical rule), and block (wherein the copolymer comprises two or more homopolymers linked by covalent units).

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "subject," "patient" or "individual" may be a human or non-human mammal or a bird. Non-human mammals include, for example, livestock and pets, such as ovine, bovine, equine, porcine, canine, feline and murine mammals. Preferably, the subject is human.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The terms "treat" "treating" and "treatment," as used herein, means reducing the frequency or severity with which symptoms of a disease or condition are experienced by a subject by virtue of administering an agent or compound to the subject.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "salt" refers to a salt of a compound contemplated within the invention, including inorganic acids, organic acids, inorganic bases, organic bases, solvates, hydrates, or clathrates thereof. As used herein, the term "salt" embraces addition salts of free acids or free bases that are compounds useful within the invention. Suitable acid addition salts may be prepared from an inorganic acid or an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, the term "cancer" is defined as disease characterized by the rapid and uncontrolled growth of aberrant cells. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, and lung cancer.

As used herein, the term "administration" means providing the composition of the present invention to a subject by any suitable method.

In one aspect, the terms "co-administered" and "co-administration" as relating to a subject refer to administering to the subject a composition of the invention, or salt thereof, along with a composition that may also treat any of the diseases contemplated within the invention. In one embodiment, the co-administered compositions are administered separately, or in any kind of combination as part of a single therapeutic approach. The co-administered composition may be formulated in any kind of combinations as mixtures of solids and liquids under a variety of solid, gel, and liquid formulations, and as a solution.

As used herein, the term "instructional material" includes a publication, a recording, a diagram, or any other medium of expression that may be used to communicate the usefulness of the compositions of the invention. In some instances, the instructional material may be part of a kit useful for generating a copolymer of the invention. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DISCLOSURE

The invention includes a copolymer comprising vanillyl alcohol as a monomer, whereby the copolymer undergoes at least partial degradation to release vanillyl alcohol within the body of a subject. In one embodiment, the subject is a mammal. In another embodiment, the mammal is human.

In one embodiment, the copolymer comprises vanillyl alcohol (VA) as a monomer. In another embodiment, (VA) is chemically bound to other monomers within the copolymer through chemical bonds to the benzylic and phenolic hydroxyl groups. In yet another embodiment, the chemical bonds comprise ester bonds.

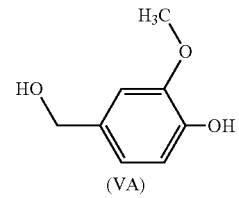

(VA)

In one embodiment, the copolymer further comprises oxalic acid as a monomer. In another embodiment, the copolymer comprises 2-(4-(hydroxymethyl)-2-methoxyphenoxy)-2-oxoacetic acid (VAOX) as a monomer, wherein VAOX may be formed by the monoesterification of oxalic acid by VA. VAOX may form chemical bonds to monomers through its benzylic hydroxyl group and/or its free carboxylic acid. In one embodiment, a PVAX copolymer comprises VAOX as a monomer.

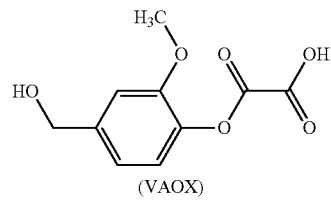

(VAOX)

In one embodiment, the copolymer further comprises 1,4-cyclohexanedimethanol (CHD) as a monomer. In another embodiment, the copolymer further comprises 2-((4-(hydroxymethyl)cyclohexyl)methoxy)-2-oxoacetic acid (CHDOX) as a monomer, wherein CHDOX may be formed by the monoesterification reaction of oxalic acid by CUD.

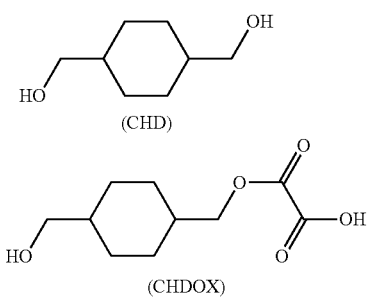
(CHD)

(CHDOX)

In one embodiment, the copolymer comprises VAOX and CHDOX as monomers. In another embodiment, the copolymer is represented by Formula (I):

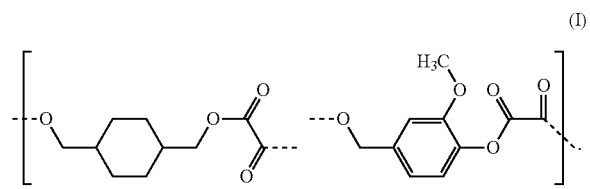

In yet another embodiment, the number of CHDOX monomers in (I) is an integer ranging from 10 to 50, and the number of VAOX monomers in (I) is an integer ranging from 5 to 30.

In one embodiment, the molar ratio of CHDOX to VAOX in the copolymer ranges from about 4:1 to about 2:3. In another embodiment, the molar ratio of CHDOX to VAOX in the copolymer is about 2:3. In yet another embodiment, the average molecular weight of the copolymer is about 10,000-20,000 Dalton.

The copolymer of the invention may be prepared according to methods known to those skilled in the art. In a non-limiting example, the copolymerization of CHDOX and VAOX building blocks may be carried out in a non-protic organic solvent, such as but not limited to dry tetrahydrofuran (THF) or dimethylformamide, under an inert atmosphere, such as nitrogen gas. In one embodiment of the present invention, 1,4-cyclohexanedimethanol and vanillyl alcohol are dissolved in dry THF. In another embodiment, the molar ratio of 1,4-cyclohexanedimethanol to vanillyl alcohol is preferably 4:1 to 2:3, and more preferably 2:3.

An organic base, such as but not limited to triethylamine or diisopropylethylamine may be then added to the mixture. In one aspect, the base serves as a catalyst and a base to remove hydrogen chloride generated in a polymer synthesis step, thus promoting the polymerization reaction. A solution of oxalyl chloride in dry organic solvent, such as THF, may then be added to the mixture, generating a PVAX copolymer. Extraction of the prepared PVAX copolymer from solution can be carried out using, in a non-limiting example, dichloromethane, and precipitation of the prepared copolymer can be carried out using, but is not limited to, cold hexane.

The present invention further includes a PVAX microparticle comprising a PVAX copolymer, wherein the PVAX copolymer comprises VAOX as a monomer. The PVAX microparticles of the present invention are non-toxic, have outstanding biocompatibility and are degraded under physiological conditions while releasing vanillyl alcohol, which has outstanding antioxidant, anti-inflammatory and anti-apoptotic effects. The PVAX microparticles of the invention are useful as drug delivery systems and components of antioxidant or anti-inflammatory compositions. Further, the PVAX microparticles inhibit or prevent side effects of anti-cancer drugs, such as hepatic or cardiac abnormalities. Further, the PVAX microparticles may be used to detect hydrogen peroxide in vivo, and are thus useful as contrast agents or for the diagnosis of ischemic disease.

In one embodiment, the PVAX copolymer is represented by Formula (I).

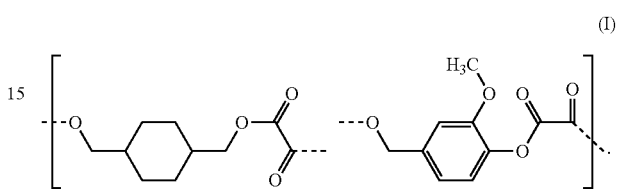

In one embodiment, the diameter of the PVAX microparticles ranges from about 200 to about 20 μm. In another embodiment, the diameter of the PVAX microparticles ranges from about 200 to about 800 nm. In yet another embodiment, the diameter of the PVAX microparticles ranges from about 400 to about 600 nm.

The PVAX microparticles may be prepared by adding a solution of the PVAX copolymer of Formula (I) in an organic solvent, such as dichloromethane, to a solution of an emulsifier. A non-limiting example of emulsifier useful within the invention is poly(vinyl alcohol), and the PVAX microparticles may be prepared by an oil-in-water emulsion method.

In one embodiment, the PVAX microparticles may further comprise a therapeutic agent or a bio-imaging agent. For example, the therapeutic agent may be an antioxidant agent, an anti-inflammatory agent, an anti-apoptotic agent or a thrombolytic agent.

Examples of the therapeutic agent include, but are not limited to, 4-amino-1,8-naphthalimide (4-AN), N-(6-oxo-5,6-dihydrophenanthridin-2-yl))-N,N-di methyl-acetamide hydrochloride (PJ34), aurintricarboxylic acid, tissue plasminogen activator protein (tPA), N-benzyloxycarbonyl-Val-Ala-Asp-fluoromethylketone (Z-VAD-FMK), manganese porphyrin, tirifiban, Glycoprotein IIb/IIIa inhibitors, or biliverdin.

Examples of the bio-imaging agent include, but are not limited to, a fluorescent agent, a far infrared-emitting agent, a radiation tracer, a PET tracer agent or a MRI contrast agent. Examples of the fluorescent agent include, but are not limited to, BODIPY dyes, DiI dyes, rubrene, pentacene, or indocyanine green. Examples of the far infrared-emitting agent include, but are not limited to, HgTe nanocrystals, PbSe nanocrystals or PbS nanocrystals. Examples of the radiation tracer include, but are not limited to, technetium-99m, molybdenum-99, thallium-201, or strontium-82. Examples of the PET tracer agent include, but are not limited to, compounds labeled with $^{11}$C, $^{15}$N, $^{15}$O, $^{18}$F or $^{82}$Rb isotopes (such as fludeoxyglucose (18F)). Examples of the MRI contrast agent include, but are not limited to, $Fe_2O_3$, $Fe_3O_4$, iron platinum and manganese.

The present invention includes a drug delivery system comprising a PVAX microparticle. As used herein, the term "drug delivery system" refers to a delivery system capable of controlling the sustained release of a therapeutic agent or drug for over a period of time e.g., hours, days, weeks, months). One or more therapeutic agents may be incorporated in the drug delivery system of the present invention. The therapeutic agent may be any biological or chemical substance that is used to prevent, treat, relief or alleviate disease, Specific examples of a therapeutic agent include, but are not limited to, proteins, peptides, compounds, extracts and nucleic acids (e.g., DNA, RNA, microRNA, recombinant virus, plasmid, nanoparticles, small molecules, oligonucleotides, or vectors). Non-limiting examples of therapeutic agents useful within the present invention include antioxidants, antibiotics, anticancer drugs, anti-inflammatory drugs, antiviral agents, antibacterial agents, anti-apoptotic agents, or hormones. The therapeutic agent may optionally contain various excipients known in the art, including diluents, release-retarding agents, inert oil or binders. The therapeutic agent incorporated in the drug delivery system of the present invention may be released by diffusion, dissolution, osmotic action or ion exchange in cells.

The present invention further includes an anti-oxidative or anti-inflammatory pharmaceutical composition, wherein the composition comprises a PVAX microparticle as an active ingredient.

Without wishing to be limited by theory, in the presence of $H_2O_2$, PVAX copolymer is cleaved, consuming one molecule of $H_2O_2$, and releasing one molecule of alcohol, which is a potent antioxidant itself. In one embodiment, the anti-oxidative activity of the composition is produced only at sites of oxidative distress.

The present invention further includes a pharmaceutical composition for preventing or treating ischemic disease, wherein the composition comprises a PVAX microparticle as an active ingredient.

Non-limiting examples of ischemic diseases contemplated within the invention include brain ischemia, heart ischemia, diabetic cardiovascular diseases, heart failure, myocardial hypertrophy, retinal ischemia, ischemic colitis, critical limb ischemia, ischemic acute renal failure, stroke, brain trauma, Alzheimer's disease, Parkinson's disease, fetal hypoxia, glaucoma, diabetic neuropathy, ischemia/reperfusion injury or ischemia/reperfusion injury complications.

In one embodiment, the ischemia/reperfusion injury is associated with cardiopulmonary bypass (CPB) surgery. In another embodiment, CPB surgery includes coronary arterial bypass graft (CABG) surgery; valve, defect or aneurysm repair; heart and/or lung transplantation; pulmonary thrombectomy; or pulmonary thromboendarterectomy.

In one embodiment, the ischemia/reperfusion injury complications associated with CPB (and/or CABG) surgery comprises atrial fibrillation, infarct extension, with reocclusion of an infarct-related artery (IRA), recurrent infarction, arrhythmia, renal function decrease, stroke, small-to-moderate MI, ventricular tachycardia/fibrillation, congestive heart failure, GI dysfunction and acute renal failure.

The present invention further includes a pharmaceutical composition for preventing or treating a complication or condition relating to solid organ transplantation (such as liver, kidney, lung or heart) or solid organ preservation (such as liver, kidney, lung or heart), wherein the composition comprises a PVAX microparticle as an active ingredient.

The present invention further includes a composition for inhibiting the side effects of anticancer drugs, comprising a PVAX microparticle as an active ingredient. As used herein, the term "anticancer drugs" collectively refers to chemotherapeutic agents used for the treatment of malignant tumors, and non-limiting examples of anticancer drugs include doxorubicin, adriamycin, cisplatin, taxol, 5-fluorouracil, and pharmaceutical acceptable salts thereof. In one embodiment, the anticancer drug is doxorubicin. Non-limiting examples of side effects of anticancer drugs include cardiomuscular dysfunctions (such as electrocardiogram abnormality, tachycardia, arrhythmia and chest pain), heart dysfunction, shock, pancytopenia, anemia, leucopenia, neutropenia, thrombocytopenia, bleeding, fever, chill, urticaria, liver dysfunction, proteinruia, loss of appetite, vomiting, nausea, mucositis, stomatitis, esophagitis, diarrhea, or headache. In one embodiment, the side effects of anticancer drugs include cardiomuscular dysfunctions or liver dysfunctions.

For providing antioxidant or anti-inflammatory effects, preventing or treating ischemic disease, or inhibiting the side effects of anticancer drugs, the composition of the present invention may be used alone or in combination with surgery, radiotherapy, hormone therapy, chemotherapy, or biological or chemical agents that control biological responses.

The pharmaceutical composition of the present invention may contain at least one known active ingredient having an antioxidant effect, an anti-inflammatory effect, the effect of preventing or treating ischemic disease, or the effect of inhibiting the side effects of anticancer drugs.

The present invention further includes a contrast agent comprising a PVAX microparticle.

The present invention further includes a composition for diagnosing ischemic disease, wherein the composition comprises a PVAX microparticle as an active ingredient.

In one embodiment, the contrast agent or the diagnostic composition further comprises a bio-imaging agent. Examples of bio-imaging agents include, but are not limited to, a fluorescent agent, a far infrared-emitting agent, a radiation tracer, a PET tracer agent and an MRI contrast agent. Examples of the fluorescent agent include, but are not limited to, BODIPY dyes, DiI dyes, rubrene, pentacene, or indocyanine green. Examples of the far infrared-emitting agent include, but are not limited to, HgTe nanocrystals, PbSe nanocrystals or PbS nanocrystals. Examples of the radiation tracer include, but are not limited to, technetium-99m, molybdenum-99, thallium-201, or strontium-82. Examples of the PET tracer agent include, but are not limited to, compounds labeled with $^{11}C$, $^{15}N$, $^{15}O$, $^{18}F$ and $^{82}Rb$ isotopes (such as fludeoxyglucose (18F)). Examples of the MRI contrast agent include, but are not limited to, $Fe_2O_3$, $Fe_3O_4$, iron platinum and manganese.

Organ or Tissue Transplantation

The invention features improved methods for organ or tissue transplantation. Ischemic damage and reperfusion injury reduces the viability of cells, tissues, or organs available for transplantation. The invention provides compositions that reduce such injury. Preferably, a composition of the invention is administered to a tissue or organ (donor organ or tissue), including but not limited to, cardiac tissue, heart, kidney tissue, kidney, hepatic tissue, liver, lung tissue, lung, pancreatic tissue, pancreas, intestine tissue, intestine, thymus, bone, cartilage, muscular tissue, tendon, cornea, epithelial tissue, skin, cardiac valve, neurons, nerves, endothelial tissue, artery, or vein, prior to, during, or after transplantation. Methods for organ transplantation are known in the art.

Methods

In one aspect, the invention includes a method of treating or preventing a disease or condition in a subject in need thereof. In one embodiment, the method comprises administering to the subject a therapeutically effective amount of a pharmaceutically acceptable composition comprising a microparticle as an active ingredient, wherein the microparticle comprises a copolymer comprising 2-(4-hydroxymethyl)-2-methoxy-phenoxy)-2-oxoacetic acid as a monomer, wherein the copolymer undergoes at least partial degradation to release vanillyl alcohol within the body of the subject, and, wherein the disease or condition is at least one selected from the group consisting of an oxidative-related disease, an inflammatory disease, an ischemic disease, a complication or condition associated with solid organ transplantation, a complication or condition associated with solid organ preservation, and a side effect of a anticancer agent, whereby the disease or condition is treated or prevented.

In another aspect, the invention includes a method of inhibiting or preventing the formation of reactive oxygen species (ROS) in at least one bodily site of a subject, wherein the method comprises administering to the subject a therapeutically effective amount of a pharmaceutically acceptable composition comprising a microparticle as an active ingredient, wherein the microparticle comprises a copolymer comprising 2-(4-hydroxymethyl)-2-methoxy-phenoxy)-2-oxoacetic acid as a monomer, wherein the copolymer undergoes at least partial degradation to release vanillyl alcohol within the body of the subject, and, whereby the formation of ROS in at least one bodily site of the subject is inhibited or prevented.

In yet another aspect, the invention includes a method of detecting or diagnosing a state associated with formation or accumulation of reactive oxygen species (ROS) in at least one bodily site of a subject, wherein the method comprises administering to the subject a pharmaceutically acceptable composition comprising a microparticle as an active ingredient, wherein the microparticle comprises a copolymer comprising 2-(4-hydroxymethyl)-2-methoxy-phenoxy)-2-oxoacetic acid as a monomer, wherein the copolymer undergoes at least partial degradation to release vanillyl alcohol within the body of the subject, and, wherein the method further comprises administering to the subject at least one bio-imaging agent selected from the group consisting of a fluorescent agent, a far infrared-emitting agent, a radiation tracer, a PET tracer agent and a MRI contrast agent, whereby the state associated with formation or accumulation of ROS in at least one bodily site of the subject is detected or diagnosed.

In still another aspect, the invention includes a method for reducing ischemic damage or reperfusion injury in a tissue or organ for transplantation, the method comprising contacting the tissue or organ with the pharmaceutical composition of claim 28 before, during or after transplantation, thereby reducing ischemic damage or reperfusion injury in said tissue or organ.

In various embodiments of any of the above aspects or any other aspect of the invention delineated herein, the ischemic disease is at least one selected from the group consisting of atherosclerosis, asthma, brain ischemia, heart ischemia, diabetic cardiovascular diseases, heart failure, myocardial hypertrophy, retinal ischemia, ischemic colitis, critical limb ischemia, ischemic acute renal failure, stroke, brain trauma, Alzheimer's disease, Parkinson's disease, fetal hypoxia, glaucoma, diabetic neuropathy, and ischemia/reperfusion injury. In other embodiments of any of the above aspects, the anticancer drug is at least one selected from the group consisting of doxorubicin, adriamycin, cisplatin, taxol, 5 fluorouracil and salts thereof. In certain embodiments of any of the above aspects, the side effect of the anticancer drug is at least one selected from the group consisting of cardiomuscular dysfunction, heart dysfunction, shock, pancytopenia, anemia, leucopenia, neutropenia, thrombocytopenia, bleeding, fever, chill, urticaria, liver dysfunction, proteinruia, loss of appetite, vomiting, nausea, mucositis, stomatitis, esophagitis, diarrhea, and headache. In other embodiments of any of the above aspects, the ROS comprises a superoxide or peroxide species. In other embodiments of any of the above aspects, the composition and the at least one bio-imaging agent are co-administered to the subject. In certain embodiments of any of the above aspects, the composition and the at least one bio-imaging agent are coformulated. In other embodiments of any of the above aspects, the tissue or organ is a cardiac tissue, heart, kidney tissue, kidney, hepatic tissue, liver, lung tissue, lung, pancreatic tissue, pancreas, intestine tissue, intestine, thymus, bone, cartilage, muscular tissue, tendon, cornea, epithelial tissue, skin, cardiac valve, neurons, nerves, endothelial tissue, artery, or vein.

Formulations/Administration

The compositions of the present invention may contain a pharmaceutical acceptable carrier, excipient and/or diluent, and may be administered by a suitable method to a subject. The compositions of the present invention may be formulated in various forms, including oral dosage forms or sterile injectable solutions, according to any conventional method known in the art. In addition, the compositions may also be used as an inhalation-type drug delivery system. In one embodiment, the compositions of the invention may be formulated as solid nanopowder.

The compositions may be formulated as powders, granules, tablets, capsules, suspensions, emulsions, syrup, aerosol, preparations for external application, suppositories and sterile injectable solutions. Suitable formulations known in the art are disclosed in, for example, Remington's Pharmaceutical Science (Mack Publishing Company, Easton Pa.). Carriers, excipients and diluents that may be contained in the composition of the present invention include lactose, dextrose, sucrose, sorbitol, mannitol, xylitol, erythritol, maltitol, starch, *acacia* gum, alginate, gelatin, calcium phosphate, calcium silicate, cellulose, methyl cellulose, microcrystalline cellulose, polyvinyl pyrrolidone, water, methyhydroxybenzoate, propyl hydroxylbenzoate, talc, magnesium stearate or mineral oil.

The compositions of the present invention may be formulated with commonly used diluents or excipients, such as fillers, extenders, binders, wetting agents, disintegrants, or surfactants. Solid formulations for oral administration include tablets, pills, powders, granules, or capsules, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, or injectable esters such as ethyl oleate may be used. As the base of the suppositories, witepsol, Macrogol, Tween 61, cacao butter, laurin fat, or glycerogelatin may be used.

The preferred dose of the pharmaceutical compositions of the present invention varies depending on the patient's condition and weight, the severity of the disease, the type of drug, and the route and period of administration and may be suitably selected by those skilled in the art. For preferred effects, the pharmaceutical composition of the present invention may be administered at a dose of 0.01-100 mg/kg/day. The composition may be administered once or several times a day.

The compositions of the present invention may be administered to a subject by various routes. All modes of administration are contemplated, for example, orally, rectally or by intravenous, intramuscular, subcutaneous, intracutaneous, intrauterine, epidural or intracerebroventricular injection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Preparation of PVAX Copolymer 1,4-cyclohexanedimethanol (approximately 10.98 mmol) and vanillyl alcohol (approximately 16.47 mmol) were dissolved in 20 mL of dry tetrahydrofuran (THF) under a nitrogen atmosphere, and triethylamine (60 mmol) was added thereto at 4° C., Herein, the amount of vanillyl alcohol in the mixture was 60% on a molar basis. To the mixture, 25 ml of a solution of oxalyl chloride (approximately 27.45 mmol) in dry THF was added dropwise at 4° C. The reaction mixture was maintained at room temperature in a nitrogen atmosphere for 6 hours, and the synthesized polymer was extracted with dichloromethane and then precipitated in cold hexane, thereby generating a PVAX copolymer.

The chemical structure of the PVAX copolymer was analyzed using $^1$H NMR spectrometry, and the molecular weight of the PVAX copolymer was analyzed by gel permeation chromatography (GPC). FIG. 1 illustrates the results of the $^1$H NMR analysis. The results of the gel permeation chromatography indicated that the PVAX copolymer had a molecular weight of about 12,000 Da (polydispersity=approximately 1.8), $^1$H NMR: 7.0-7.3 (m, 3H, Ar), 5.3 (m, 2H OCH$_2$-PhO—CH$_3$), 4.1-4.2 (m, 4H, COOCH$_2$CH), 3.8 (m, 3H, OCH$_3$), 2.2 (m, 2H, C(CH$_2$)$_3$HO), 1.0-1.8 (m, 8H, cyclic CH$_2$).

Example 2: Preparation of PVAX Microparticles

PVAX microparticles were prepared from the PVAX copolymer prepared in Example 1. Specifically, to a solution of 50 mg of the PVAX copolymer in 500 μL of DCM, 5 mL of 10 (w/v) % poly(vinyl alcohol) solution was added. The reaction mixture was sonicated using a sonicator (Fisher Scientific, Sonic Dismembrator 500) for 30 seconds and homogenized (PRO Scientific, PRO 200-homogenizer) for 2 minutes to form a purified oil/water emulsion, 20 mL of PVA w/w %) solution was added to the emulsion, which was then homogenized for 1 minute. The resulting solution was evaporated using a rotary evaporator to remove the remaining solvent, followed by centrifugation at 4° C. and 11,000 rpm for 5 minutes, thereby obtaining PVAX microparticles. The PVAX microparticles were washed twice with deionized water and used in subsequent tests.

Example 3: Properties of PVAX Microparticles

Physical Properties

Figure 2:
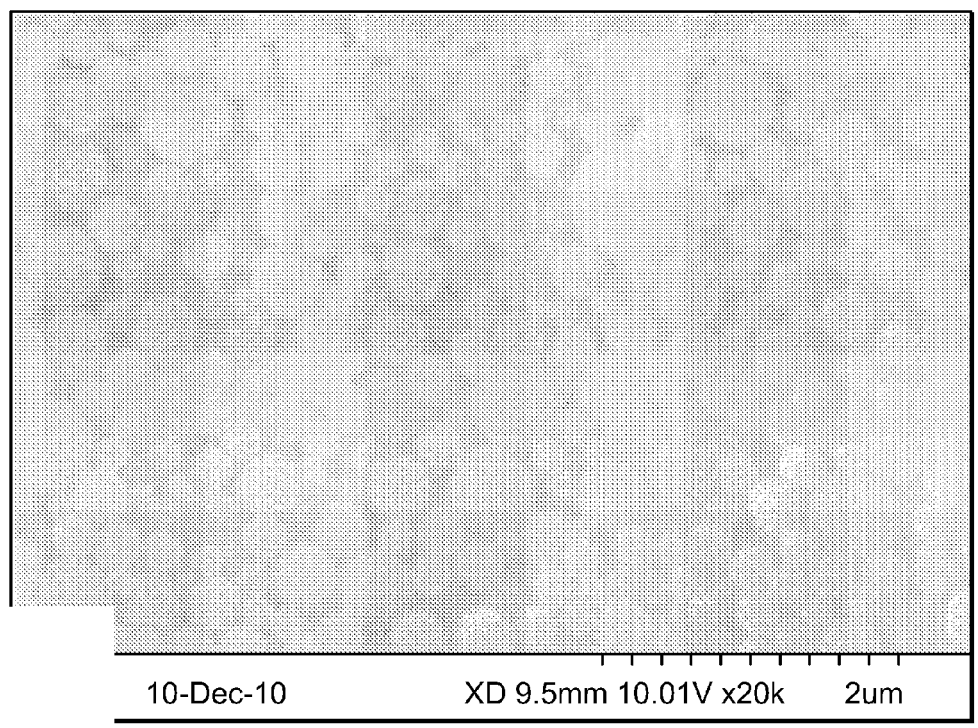
FIG. 2 is a scanning electron microscope (SEM) photograph illustrating the shape of PVAX microparticles.
Figure 3:
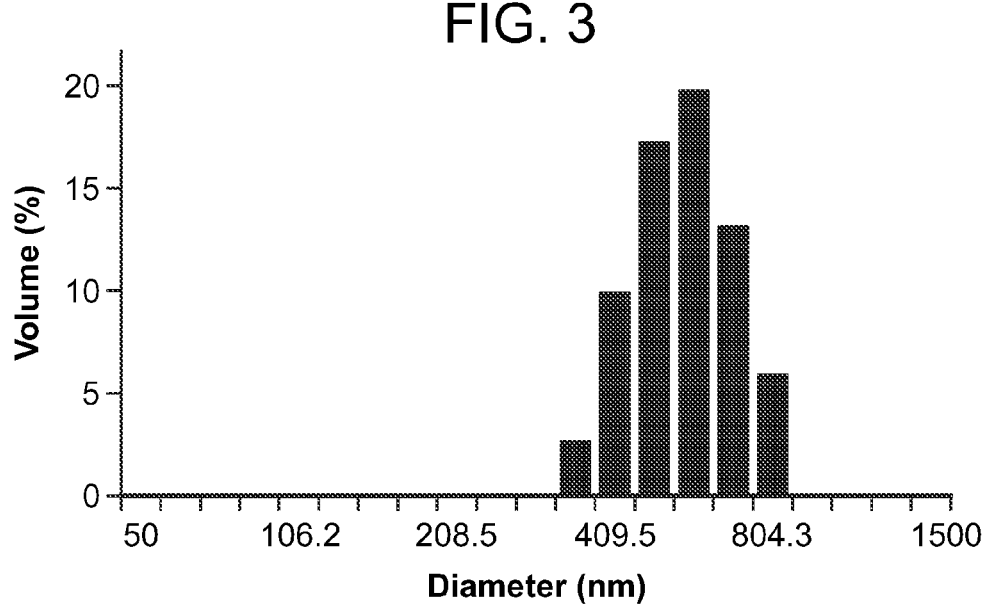
FIG. 3 is a bar graph illustrating the size of PVAX microparticles as measured by a particle size analyzer.

The shape and size of the PVAX microparticles prepared in Example 2 were evaluated. The shape of the PVAX microparticles was studied with a scanning electron microscope (SEM) (S-3000N, Hitachi, Japan), and the diameter of the microparticles was measured with a particle size analyzer (ELS-8000, Photal Otsuka Electronics, Japan). The results of the measurement, illustrated in FIGS. 2-3, indicated that the PVAX microparticles were round spheres having an average diameter of about 500 nm.

Intracellular Absorption

In order to examine the intracellular absorption of the PVAX microparticles prepared in Example 2, the following test was carried out using macrophages known to phagocytose foreign matter having a size of 0.5-3 μm.

Figure 4:
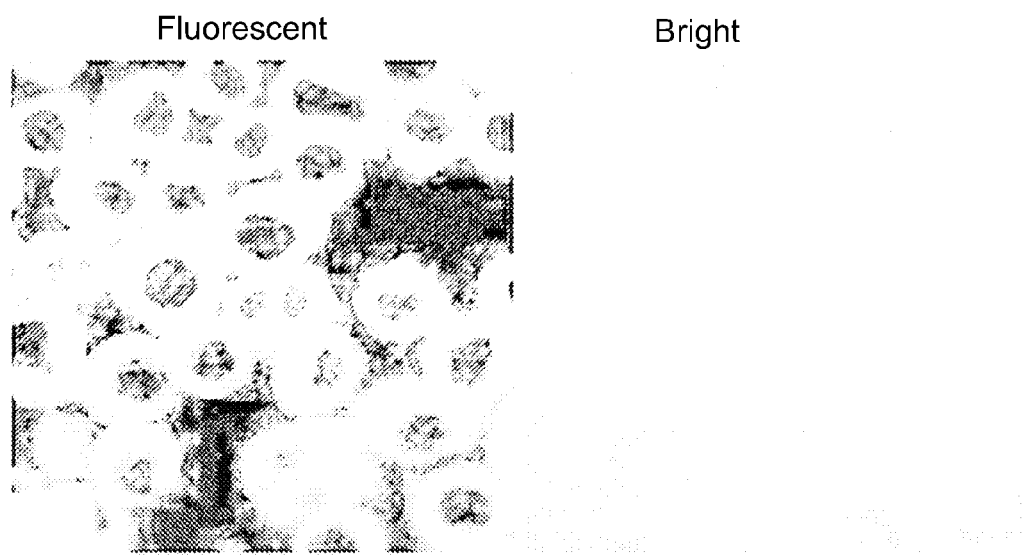
FIG. 4 is a set of confocal laser scanning micrographs illustrating the intracellular absorption of PVAX microparticles.

RAW 264.7 cells were incubated with coumarin-conjugated PVAX microparticles for 1 hour, and then observed with a confocal laser scanning microscope. As illustrated in FIG. 4, the macrophages showed the intact and bright green fluorescent particles, demonstrating that the PVAX microparticles are taken up by macrophages and are useful as intracellular drug delivery systems.

Release of Vanillyl Alcohol

In order to confirm the release of vanillyl alcohol from the PVAX microparticles prepared in Example 2, the following test was carried out. First, 5 mg of the PVAX microparticles were added to 5 ml of PBS (pH 7.4), followed by stirring at 37 C. At appropriate intervals, the stirred solution was centrifuged at 2,000 g for 20 seconds, and 1 ml of the supernatant was taken and replaced with the same amount of fresh PBS. The concentration of vanillyl alcohol in the supernatant was measured using a UV spectrometer (S-3100, Scinco, Korea) and the release kinetics was analyzed.

Figure 5:
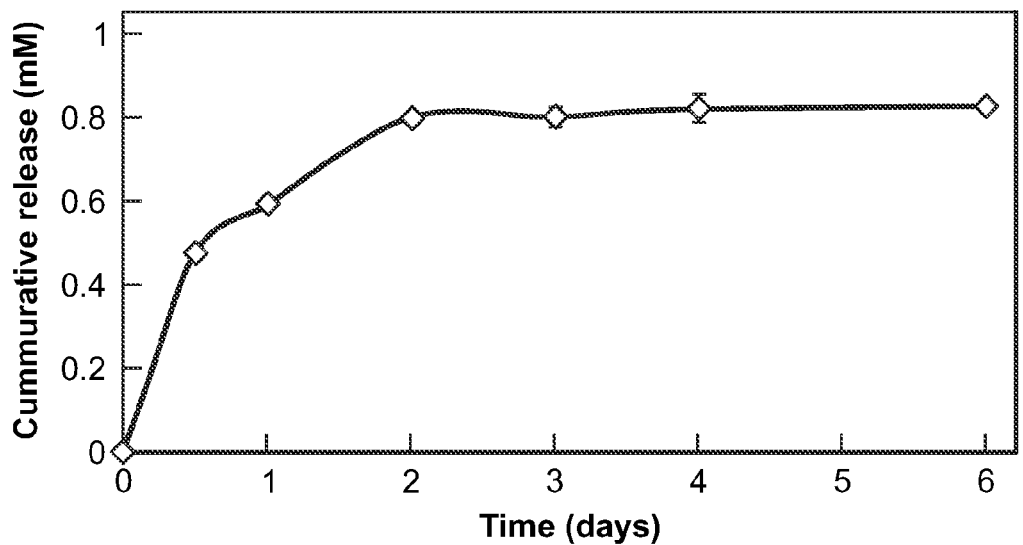
FIG. 5 is a graph illustrating the rate of release of vanillyl alcohol from PVAX microparticles.

As illustrated in FIG. 5, the PVAX microparticles (1 mg/ml) released about 0.8 mM of vanillyl alcohol (~110 mg) during hydrolysis, and half of vanillyl alcohol was released within about 24 hours. The above results are consistent with the hydrolysis of labile peroxalate ester bonds in the copolyoxalate backbone of the PVAX microparticles, with release of vanillyl alcohol. The rapid hydrolysis and VA release may provide benefits for the treatment of diseases that require fast onset of therapeutic action.

Example 4: Toxicity of PVAX Microparticles

Cytotoxicity

In order to analyze the cytotoxicity of the PVAX microparticles prepared in Example 2, a MTT (3-(4,5-dimethylthiazol-2-yl)-2,5-diphenyltetrazolium bromide) assay was carried out.

Specifically, RAW 264.7 cells were seeded in a 24-well plate at a density of $1 \times 10^6$ cells/well, and then cultured for 24 hours. The cells were treated with the PVAX microparticles at various concentrations (10-100 µg/mL) and then incubated for 2.4 hours. The medium was removed, and 20 µL of an MTT reagent was added to each well, followed by incubation for 4 hours. Then, 200 µL of DMSO (dimethyl sulfoxide) was added to each well and incubated for 30 minutes, after which the absorbance at 570 nm was measured using a microplate reader (E-Max, Molecular Device Co. US). The cell viability was analyzed by comparing the absorbance of PVAX microparticles-treated cells to that of control cells.

Figure 6:
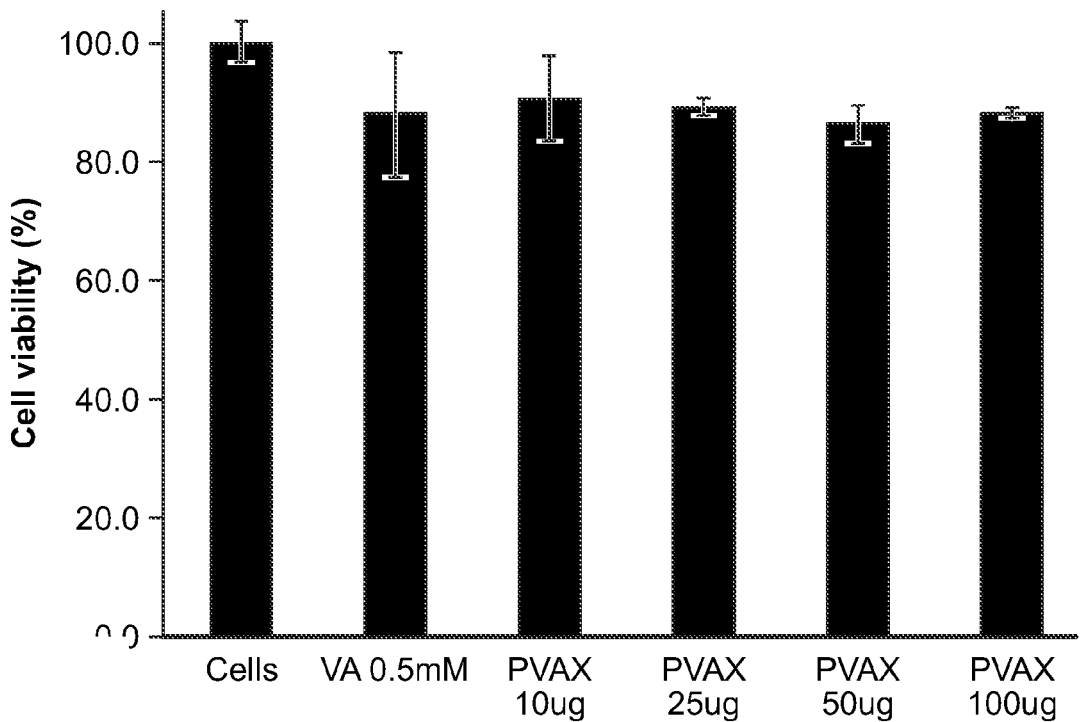
FIG. 6 is a bar graph illustrating the results of a MTT assay conducted to evaluate the cytotoxicity of PVAX microparticles.

As illustrated in FIG. 6, the PVAX microparticles did not display significant cytotoxicity up to a concentration of 100 µg/ML and were biocompatible. This indicates that the PVAX microparticles are biocompatible and non-toxic to cells.

In Vivo Toxicity

In order to analyze the in vivo toxicity of the PVAX microparticles prepared in Example 2, the following test was carried out. The PVAX microparticles were administered to mice every day for 7 days, and blood was collected from the mice to analyze the effects of the PVAX microparticles on the kidney and liver functions.

Figure 7:
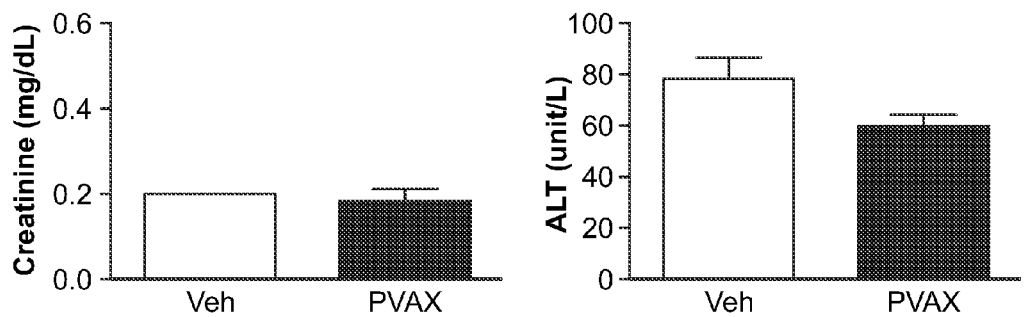
FIG. 7 is a set of bar graphs illustrating blood creatinine and ALT levels measured after administration of PVAX microparticles to mice.

As illustrated in FIG. 7, the levels of the kidney function-related marker creatinine and the liver function-related marker ALT in the mice administered with the PVAX microparticles had no significant difference from those of a control group.

Figure 8:
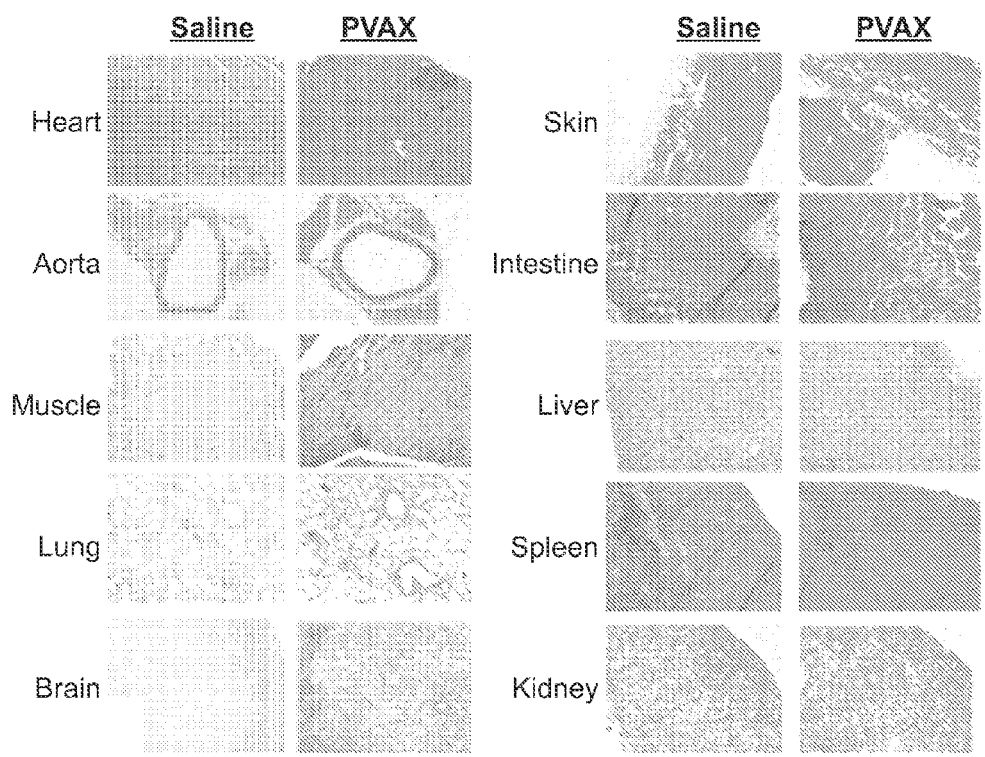
FIG. 8 is a set of photographs illustrating the results of histological analysis conducted to examine the toxic effects of PVAX microparticles on mice tissues (heart, skin, artery, intestinal organs, muscle, liver, lung, spleen, brain and kidney).

Also, various tissues (heart, skin, artery, intestinal organs, muscle, liver, lung, spleen, brain, and kidney) were extracted from the mice, and the histological analysis of the tissues was carried out. As illustrated in FIG. 8, histological data did not show signs of PVAX-related toxicity in various tissues of the mice administered with the PVAX microparticles.

Example 5: Anti-Oxidative Activity of PVAX Microparticles

In order to examine the anti-oxidative activity of the PVAX microparticles prepared in Example 2, the following test was carried out.

Amplex Red Assay 1 ml of 10 µM hydrogen peroxide ($H_2O_2$) was treated with the PVAX microparticles at various concentrations (250-1,000 µg/mL) and incubated with stirring at 37° C. for 24 hours. After short centrifugation, the concentration of $H_2O_2$ in the supernatant was measured using an amplex red assay (Invitrogen, US). The results of the measurement are illustrated in FIGS. 9-11.

Figure 9:
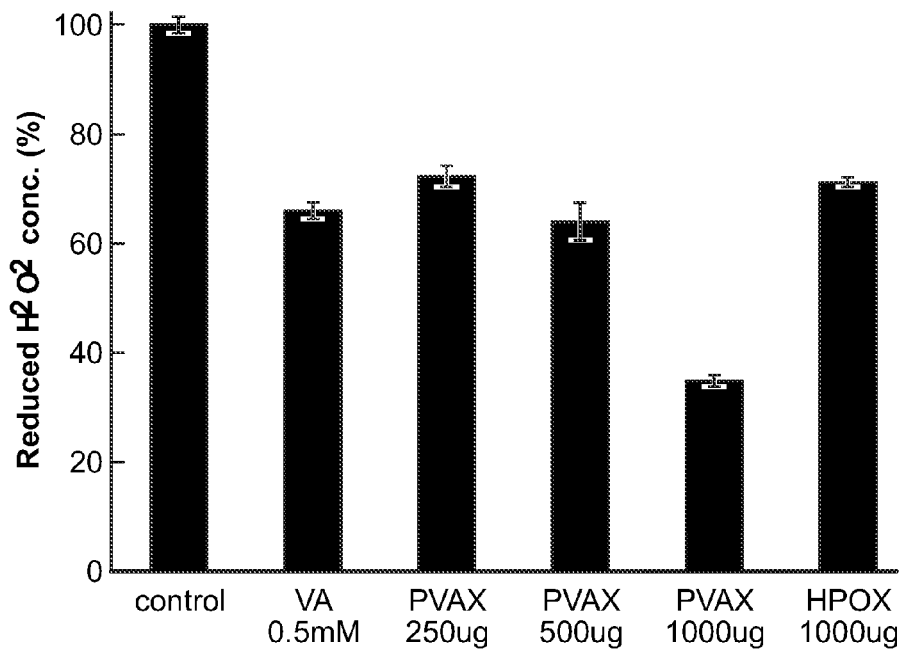
FIG. 9 is a bar graph illustrating the results of an Amplex Red assay conducted to determine the antioxidant activity of PVAX microparticles.
Figure 10:
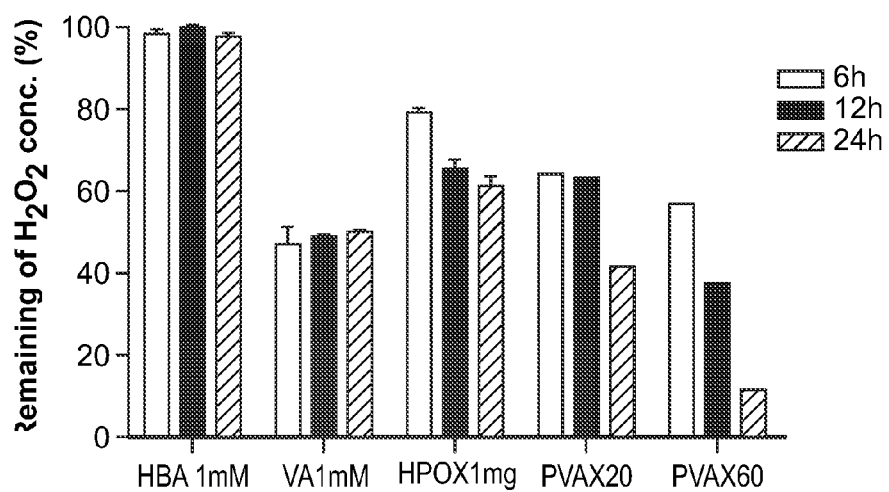
FIG. 10 is a bar graph illustrating the sensitivity of PVAX microparticles to hydrogen peroxide ($H_2O_2$).
Figure 11:
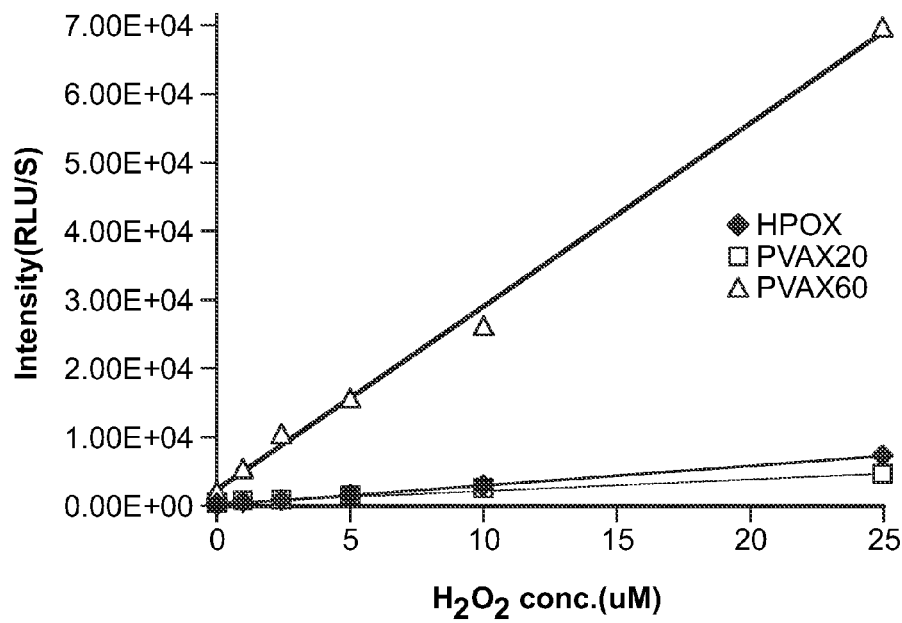
FIG. 11 is a graph illustrating the sensitivity of PVAX microparticles to hydrogen peroxide.

As illustrated in FIG. 9, the concentration of hydrogen peroxide decreased in a manner dependent on the concentration of the PVAX microparticles, addition, as illustrated in FIGS. 10-11, the PVAX microparticles (PVAX60) prepared using vanillyl alcohol in a molar amount of 60% had increased sensitivity to hydrogen peroxide compared to the PVAX microparticles (PVAX20) prepared using vanillyl alcohol in a molar amount of 20%, suggesting that PVAX60 has a significant antioxidative effect.

Measurement of Reactive Oxygen Species (ROS) Production

The effect of the PVAX microparticles on the production of ROS RAW 264.7 cells activated with PMA (phorbol-12-myristate-13-acetate) was analyzed.

Specifically, RAW 264.7 cells were treated with 100 µg of the PVAX microparticles and incubated for 4 hours. The cells were treated with 0.5 mg PMA to stimulate the production of reactive oxygen species in the cells. After 4 hours, the cells were treated with DCFH-DA (dichlorofluorescin-diacetate), after which DCF (dichlorodihydrofluorescein) (a marker of intracellular oxidative stress) was analyzed using a flow cytometer (Becton Dickinson, US).

Figure 12A:
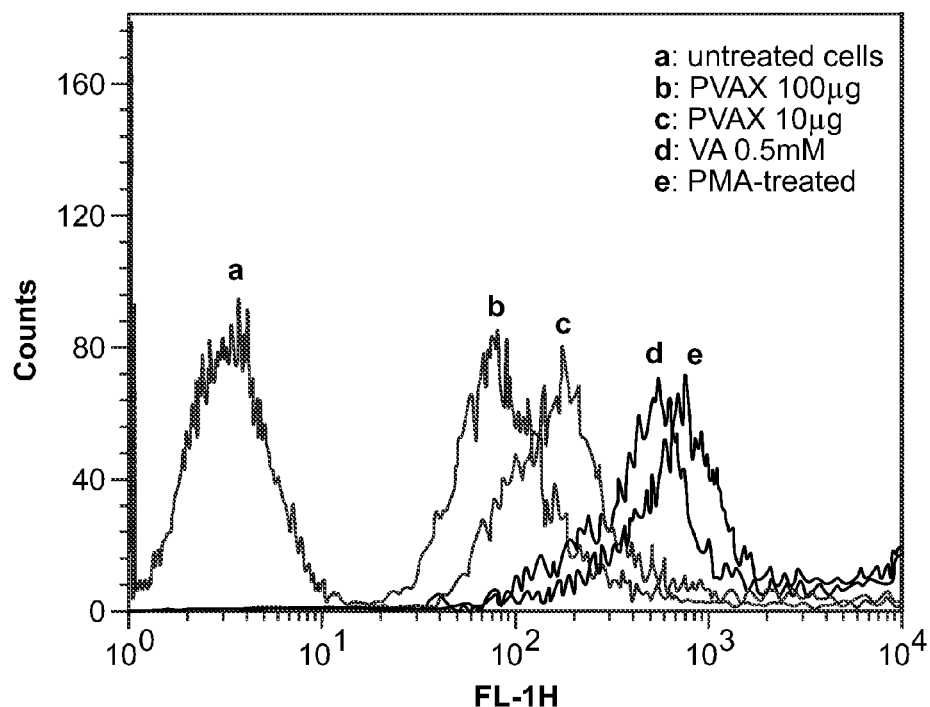
FIGS. 12A-12C, is a set of graphs and table illustrating the effect of PVAX microparticles on the inhibition of ROS production.

As illustrated in FIG. 12A, PMA treatment resulted in strong dichlorofluorescein (DCF) fluorescence in cells, which is indicative of oxidative stress in cells. Alone VA (0.5 mM) only slightly suppressed ROS generation, but PVAX remarkably inhibited the intracellular ROS generation.

Figure 12B:
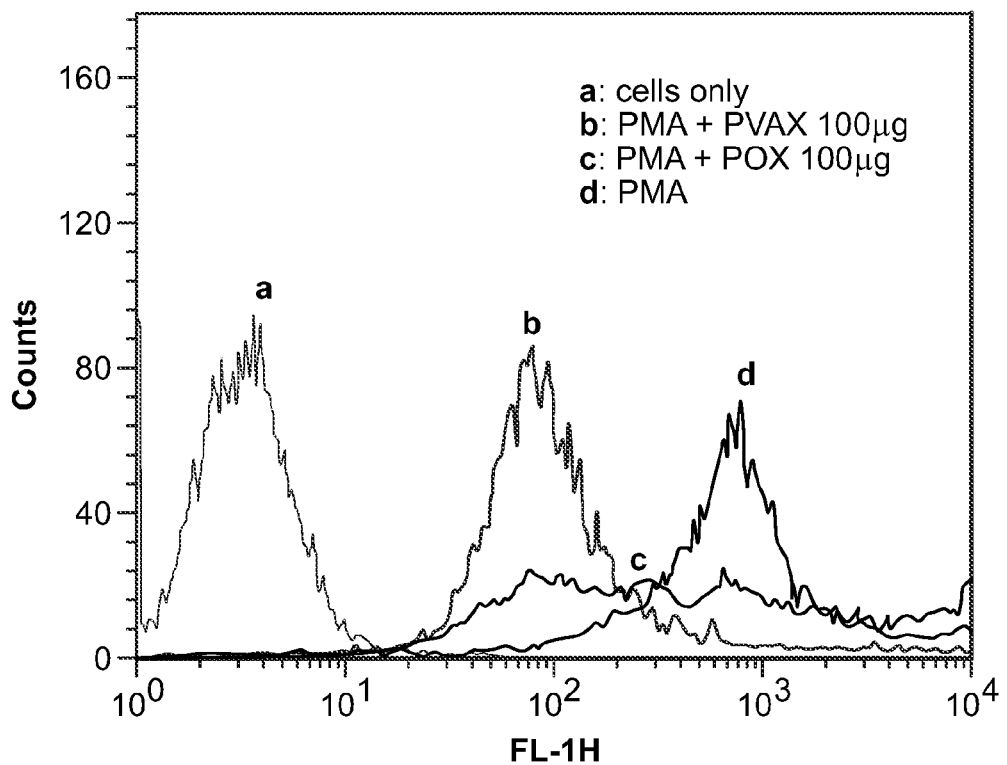
Figure 12C:
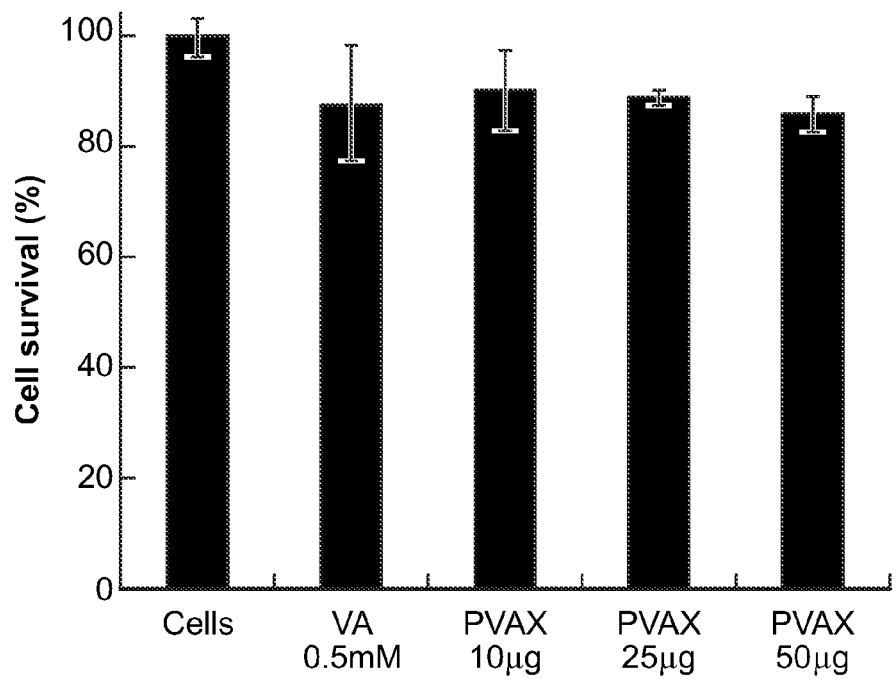

To shed light on the mechanism of action of the inhibitory effects of VA on ROS generation, the action of VA alone was compared to polyoxalate (POX), which has only aliphatic peroxalate ester bonds and cannot release VA (FIG. 12B). These results demonstrate that PVAX exhibited significantly more reduction in PMA-induced ROS generation than POX particles, indicating that antioxidant activities of PVAX occurs by first scavenging intracellular $H_2O_2$ and then releasing VA that inhibits the further generation of ROS in a biocompatible way.

Example 6: Anti-Inflammatory Activity of PVAX Microparticles

In order to examine the anti-inflammatory activity of the PVAX microparticles prepared in Example 2, the expression of inflammation-related cytokines in cells activated with UPS (lipopolysaccharide) was analyzed.

Figure 13:
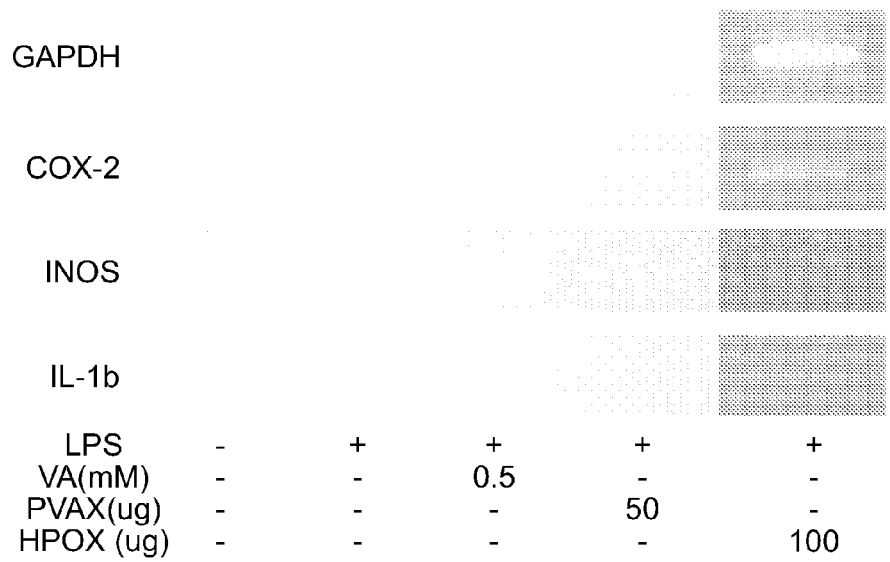
FIG. 13 is a set of gel photographs illustrating the effect of PVAX microparticles on glyceraldehyde 3-phosphate dehydrogenase (GAPDH), cyclooxygenase-2 (COX-2), inducible nitrogen oxide synthase (iNOS), and interleukin-1 beta (IL-beta), which is an inflammatory cytokine.

As illustrated in FIG. 13, in the cells treated with LPS alone, the mRNA expressions of proinflammatory cytokines or mediators, such as IL-1, iNOS (inducible nitric oxide synthase) and COX-2 (cyclooxygenase-2), significantly increased. However, in the cells treated with LPS together with the PVAX microparticles, the mRNA expressions of the cytokines decreased, suggesting that the PVAX microparticles have an anti-inflammatory effect.

Example 7: Analysis of Anti-Apoptotic Activity of PVAX Microparticles

In order to examine the anti-apoptotic activity of the PVAX microparticles prepared in Example 2, the following test was carried out.

RAW 264.7 cells were treated with the PVAX microparticles at various concentrations (50 and 100 μg) and incubated for 4 hours. The cells were treated with 100 of $H_2O_2$ to induce apoptosis. After 4 hours, the cells were treated with FITC-labeled Annexin-V for 15 minutes, and then analyzed using a flow cytometer (Becton Dickinson, USA).

Figure 14:
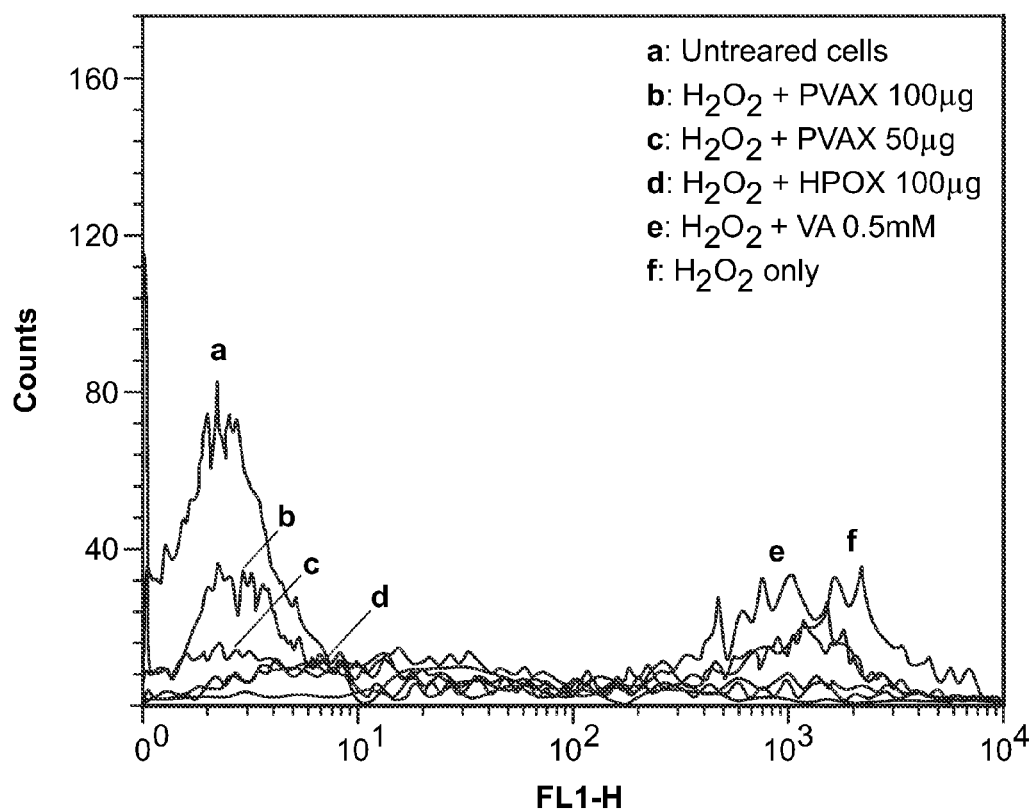
FIG. 14 is a graph illustrating the apoptosis inhibitory activity of PVAX microparticles.

As illustrated in FIG. 14, in the cells treated with $H_2O_2$ alone, apoptosis appeared, but in the cells treated with $H_2O_2$ together with the PVAX microparticles, apoptosis induced by $H_2O_2$ was significantly inhibited.

Example 8: Function of PVAX Microparticles as Contrast Agent

In order to confirm whether the PVAX microparticles prepared in Example 2 functions as a contrast agent, the following test was carried out using an ischemia/reperfusion (I/R) injury animal model.

Specifically, ischemia was induced in the hindlimb of mice according to a general experimental method, and rubrene-conjugated PVAX microparticles were injected into the ischemic site for 1 minute before reperfusion. Then, chemiluminescent images of the ischemic site were analyzed using an IVIS imaging system.

Figure 15:
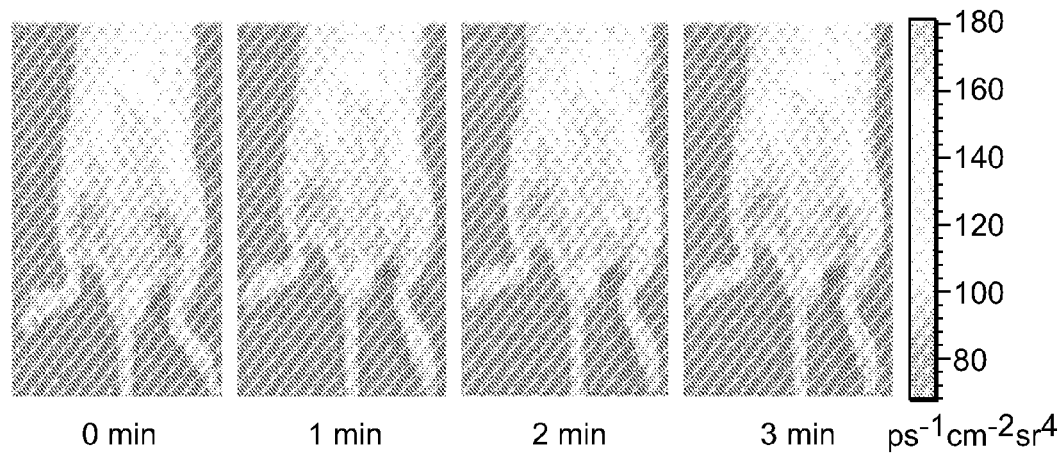
FIGS. 15 and 16 are sets of photographs illustrating the function of PVAX microparticles as a hydrogen peroxide-specific contrast agent in an ischemia/reperfusion injury model.

As illustrated in FIG. 15, strong chemiluminescence intensity appeared at the ischemia/reperfusion injury site and disappeared 5 minutes after reperfusion. In contrast, negligible chemiluminescent emission was observed in the site of ischemia only. Such results demonstrate that the PVAX microparticles are capable of imaging $H_2O_2$ endogenously generated during I/R injury.

In order to further confirm the $H_2O_2$-specific detection of the PVAX microparticles, catalase (a $H_2O_2$-degrading enzyme) was injected into the ischemic site prior to injection of the PVAX microparticles.

Figure 16:
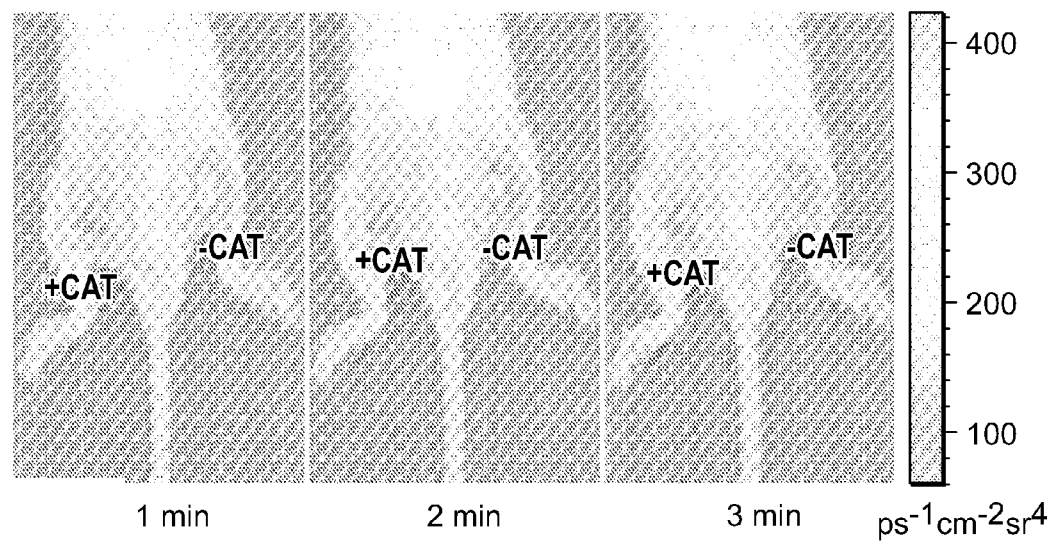

As illustrated in FIG. 16, pre-administration of catalase almost completely inhibited chemiluminescence emission from the PVAX microparticles at the site of I/R injury. Such results suggest that the PVAX microparticles can be used as a substance of diagnosing I/R injury by specifically detecting $H_2O_2$.

Example 9: Therapeutic Effect of MAX Microparticles in Hindlimb Ischemia/Reperfusion Animal Model In order to examine the therapeutic effect of the PVAX microparticles, prepared in Example 2, in a hindlimb ischemia/reperfusion animal model, the following test was carried out.

After ischemia/reperfusion injury has occurred in the mouse hindlimb, the PVAX microparticles were administered into the gastrocnemius muscle at various concentrations (25, 50, and 100 μg). After 2 days, the mice were sacrificed and the expressions of enzymes and cytokines in the muscle tissue were analyzed. After 2 weeks, the gastrocnemius muscle tissue was separated and analyzed by H&E staining. The results of the analysis are illustrated in FIGS. 17-22.

Figure 17:
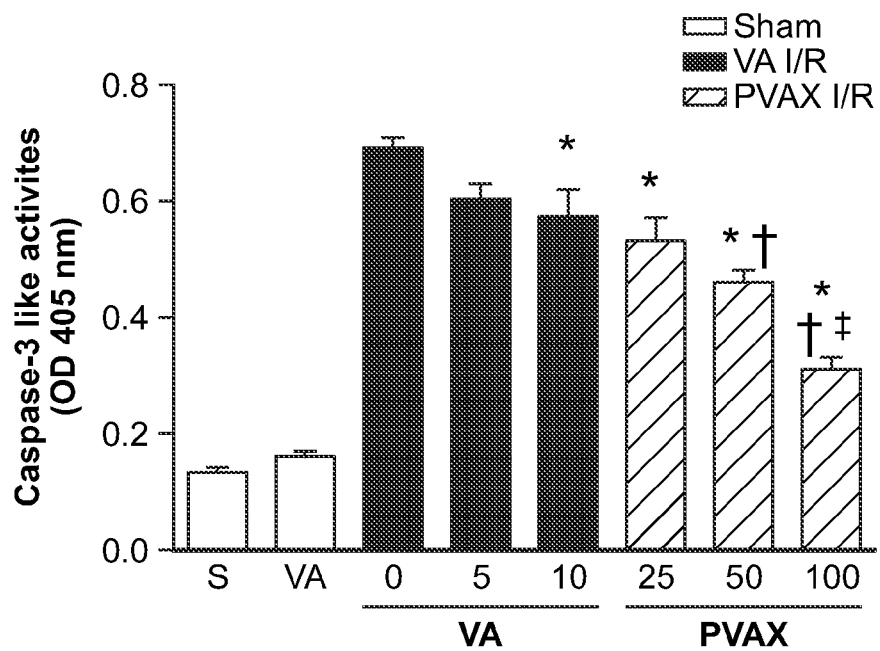
FIG. 17 is a bar graph illustrating the effect of PVAX microparticles in caspase-3 enzyme activity in a hindlimb ischemia/reperfusion injury model.
Figure 18:
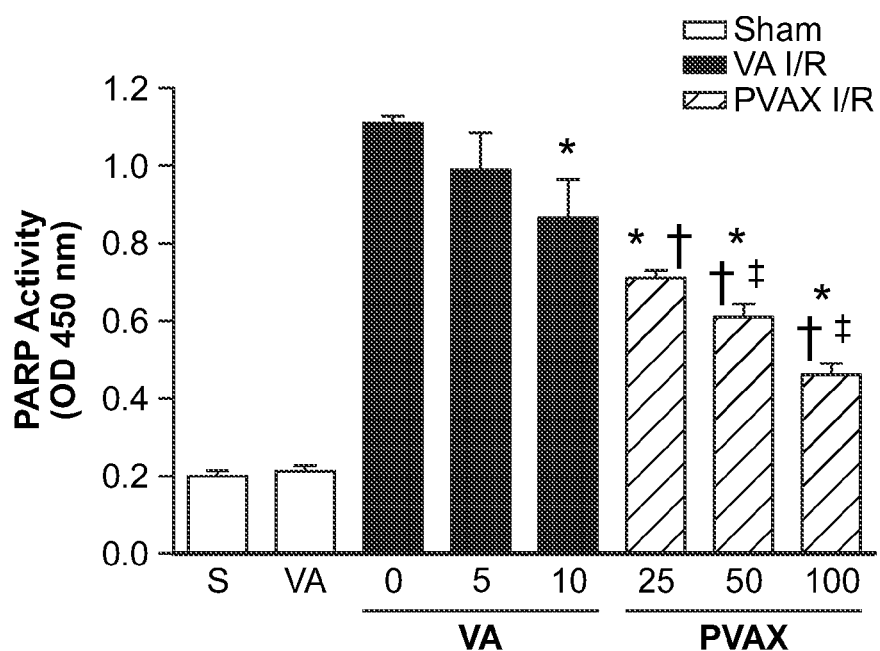
FIG. 18 is a bar graph illustrating the effect of PVAX microparticles in PARP-1 enzyme activity in a hindlimb ischemia/reperfusion injury model.

As illustrated in FIGS. 17-18, in the group injected with 100 μg of the PVAX microparticles, the activities of PARP-1 (polyADP ribose polymerase-1) and caspase-3, which are apoptosis-related enzymes, were significantly inhibited, and the PVAX microparticles showed excellent effects compared to vanillyl alcohol alone.

Figure 19:
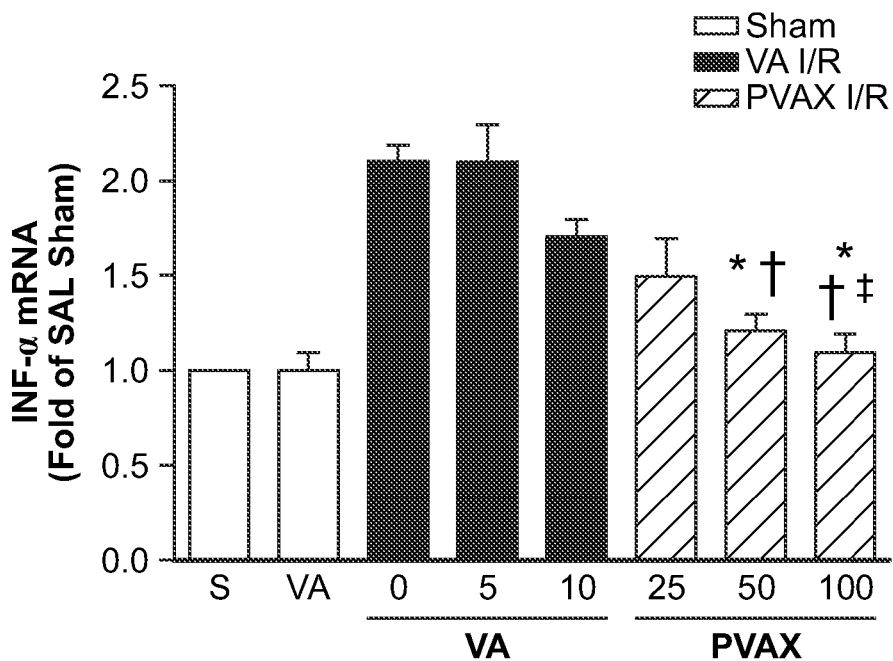
FIG. 19 is a bar graph illustrating the effect of PVAX microparticles on the expression of TNF- in a hindlimb ischemia/reperfusion injury model.
Figure 20:
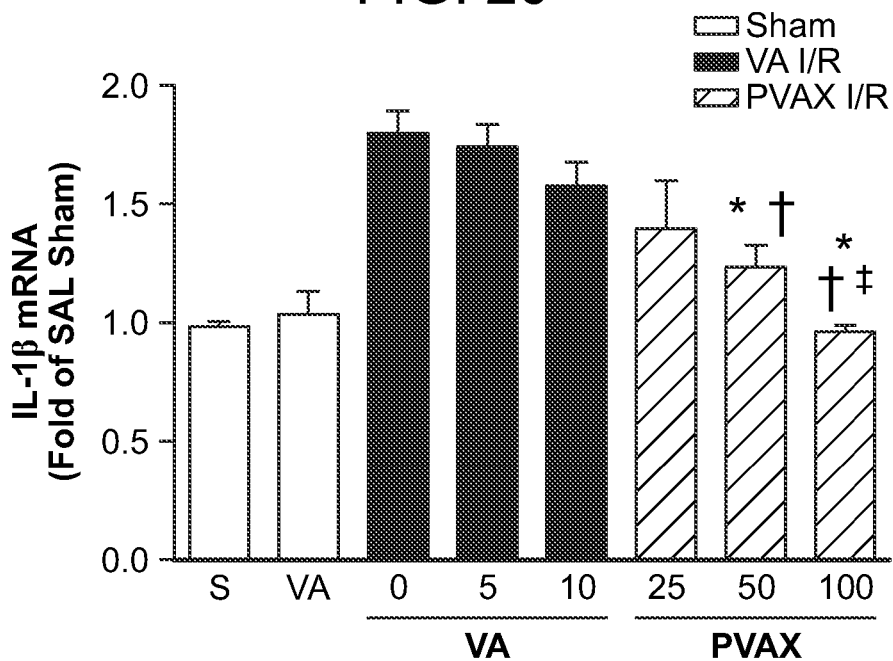
FIG. 20 is a bar graph illustrating the effect of PVAX microparticles on the expression of IL-1 in a hindlimb ischemia/reperfusion injury model.
Figure 21:
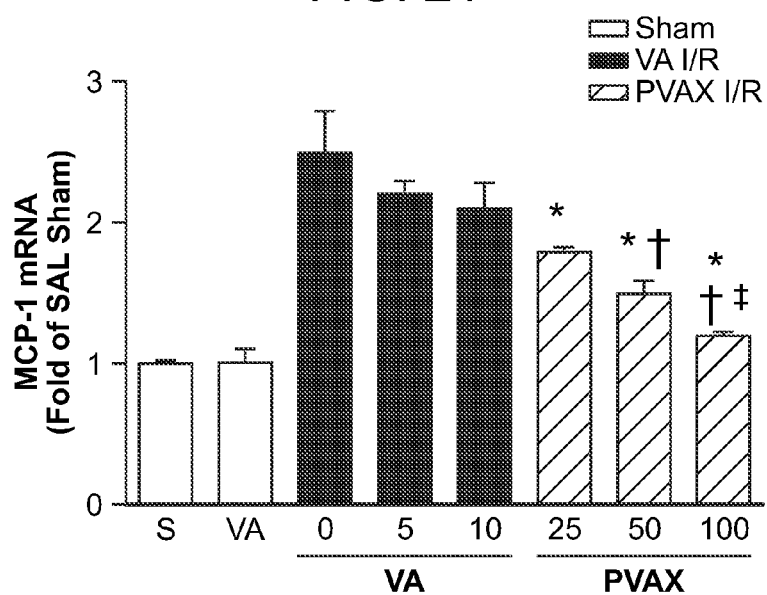
FIG. 21 is a bar graph illustrating the effect of PVAX microparticles on the expression of MCP-1 in a hindlimb ischemia/reperfusion injury model.

As illustrated in FIGS. 19-21, in the group injected with 100 μg of the PVAX microparticles, the mRNA expressions of the inflammation-related cytokines TNF-α (tumor necrosis factor-alpha), IL-1β and MCP-1 (monocyte chemotactic protein-1) significantly decreased, and the PVAX microparticles showed excellent effects compared to vanillyl alcohol alone.

Figure 22:
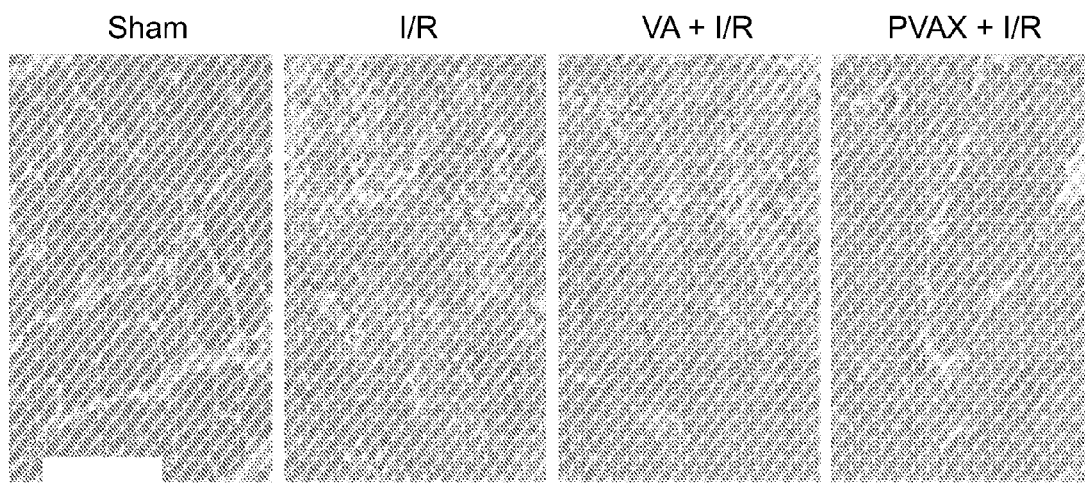
FIG. 22 is a set of photographs illustrating the effect of PVAX microparticles on recovery from muscle damage in a hindlimb ischemia/reperfusion injury model.

As illustrated in FIG. 22, in the group injected with 100 μg of the PVAX microparticles, muscle damage induced by ischemia/reperfusion injury significantly decreased.

Example 10: Therapeutic Effect of PVAX Microparticles in Hepatic Ischemia/Reperfusion Animal Model In order to examine the therapeutic effect of the PVAX microparticles, prepared in Example 2, in a hepatic ischemia/reperfusion animal model, the following test was carried out.

200 μg of the PVAX microparticles were administered intraperitoneally into mice, and ischemia in the mice was induced. At the start of reperfusion, 100 μg of the PVAX microparticles were injected intraperitoneally into the mice, and reperfusion injury in the mice was induced for 6 hours. At 24 hours after the first administration of the PVAX microparticles, the mice were sacrificed, and the serum ALT levels and the expressions of enzymes and cytokines in the hepatic tissue were analyzed. The results of the analysis are illustrated in FIGS. 23-28.

Figure 23:
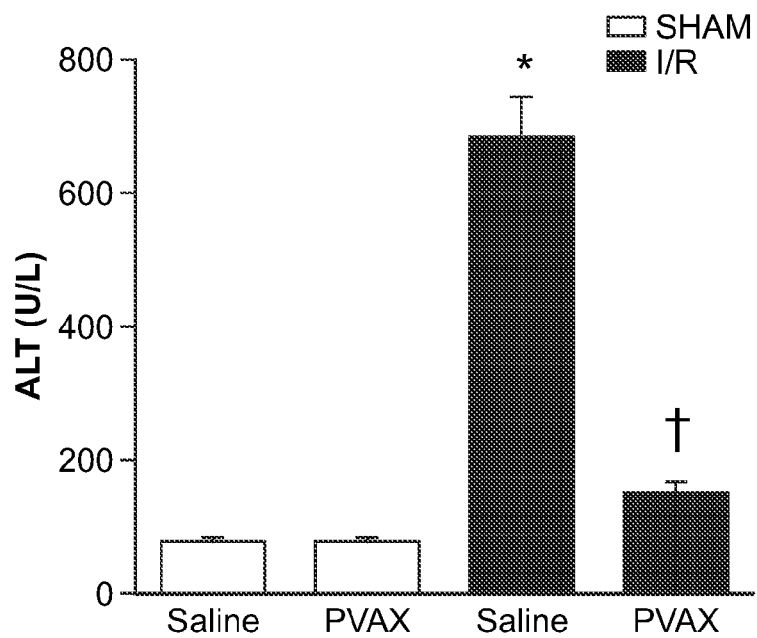
FIG. 23 is a bar graph illustrating the effect of PVAX microparticles on serum ALT levels in a hepatic ischemia/reperfusion injury model.

As illustrated in FIG. 23, the serum ALT level of the control group significantly increased compared to that of the normal group (SHAM), and a rise in the liver injury marker ALT in the group injected with the PVAX microparticles was inhibited.

Figure 24:
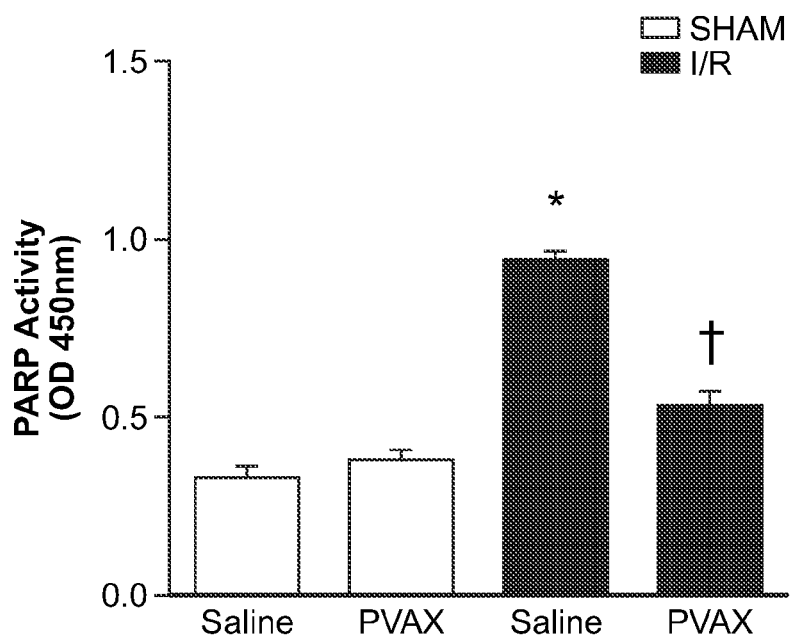
FIG. 24 is a bar graph illustrating the effect of PVAX microparticles on PARP-1 enzyme activity in a hepatic ischemia/reperfusion injury model.
Figure 25:
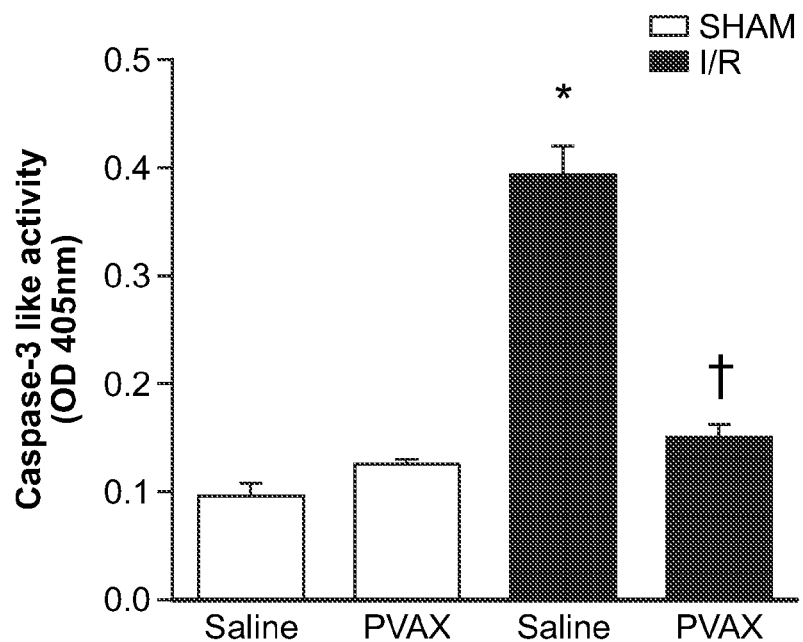
FIG. 25 is a bar graph illustrating the effect of PVAX microparticles on caspase-3 enzyme activity in a hepatic ischemia/reperfusion injury model.

As illustrated in FIGS. 24-25, in the liver tissue of the group injected with the PVAX microparticles, the activities of PARP-1 and caspase-3, which are apoptosis-related enzymes, were significantly inhibited.

Figure 26:
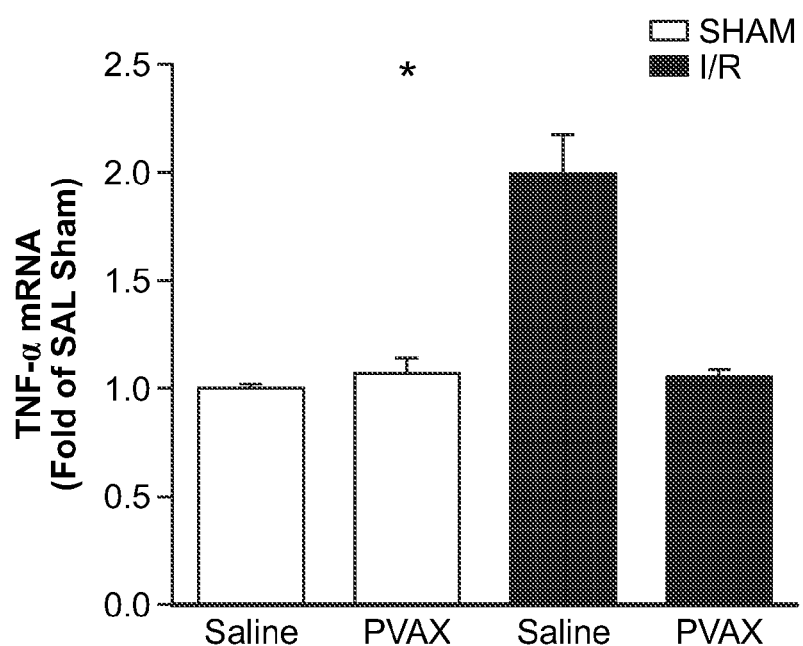
FIG. 26 is a bar graph illustrating the effect of PVAX microparticles on the expression of TNF-α in a hepatic ischemia/reperfusion injury model.
Figure 27:
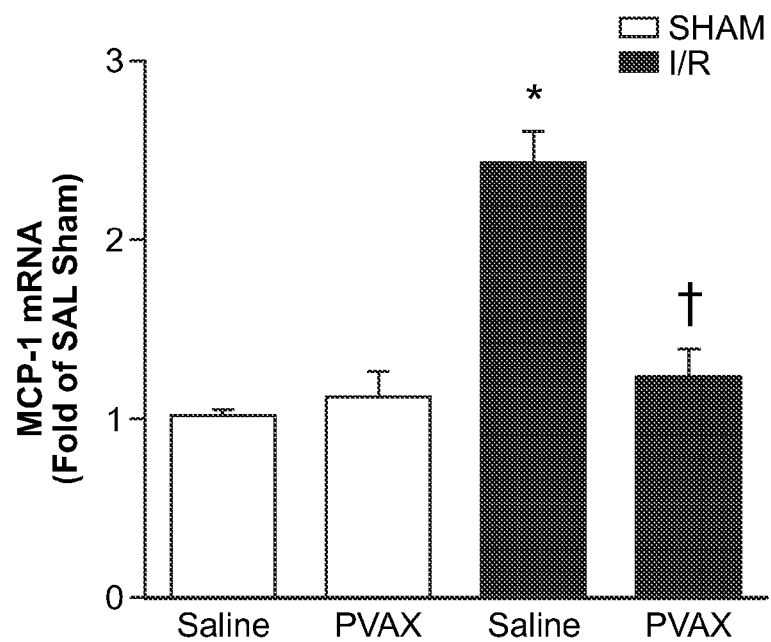
FIG. 27 is a bar graph illustrating the effect of PVAX microparticles on the expression of MCP-1 in a hepatic ischemia/reperfusion injury model.
Figure 28:
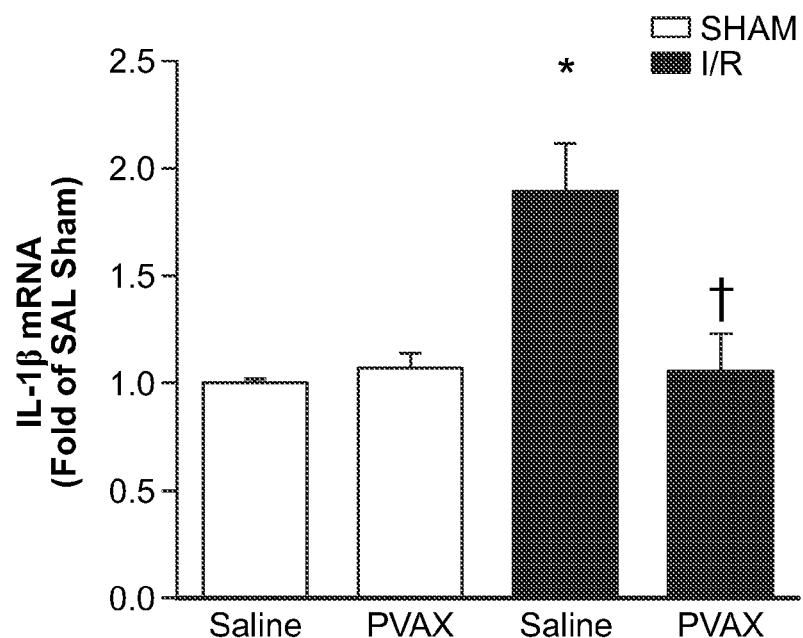
FIG. 28 is a bar graph illustrating the effect of PVAX microparticles on the expression of IL-1β in a hepatic ischemia/reperfusion injury model.

As illustrated in FIGS. 26-28, in the liver tissue of the group injected with the PVAX microparticles, the mRNA expressions of TNF-α, MCP-1 and IL-1β which are inflammation-related cytokines, significantly decreased.

Example 11: Function of PVAX Microparticles as Agent for Inhibiting Side Effects of Anticancer Drugs: Doxorubicin-Induced Cardio and Hepatoxicities In Vivo Doxorubicin (DOX) is a widely used anticancer agent; however its clinical use has been limited due to serious side effects of cardiac and hepatic injury. Reactive species oxygen (ROS) played a key role in their toxic mechanism of oxidative stress and cell death. Since PVAX polymers have anti-oxidative and anti-inflammatory effects, their effect on DOX-induced cardio and hepatotoxicities in vivo were evaluated.

DOX-treated control groups exhibited a high level of TNF-α and MCP-1. However, with the addition of PVAX (3 mg/kg/day) DOX-treated mice there was a significant decrease TNF-< and MCP-1 expressions as well as reduced apoptosis. In addition, evaluation PARP-1 and caspase-3 activity, markers of apoptosis, showed that DOX treatment significantly increased PARP-1 and caspase-3 activity. PVAX effectively reduced PARP-1 and caspase-3 activation. These results support that PVAX have significant anti-oxidant and anti-inflammatory effect as well as effective inhibition of apoptosis.

DOX treatment has been shown to result in cardiac dysfunction. Thus, cardiac function was assessed by measuring ejection fraction (EF) and fractional shortening (FS) between particle-treated group and vehicle group by echocardiogram, DOX-treated groups demonstrated lower EF (mean 25.54, SEM 2.69) and FS (mean 50.41, SEM 0.75), compared to DOX followed by WAX particle-treated group (EF mean 35.52, SEM 2.59 and FS mean 59.2, SEM 1.03, respectively). The PVAX-treated mice have less deterioration of cardiac function, reflecting cardio-protective effects of PVAX in the setting of DOX-induced myocardial damage.

In order to examine whether the PVAX microparticles prepared in Example 2 function as an agent for inhibiting the side effects of anticancer drugs, the following test was carried out using a doxorubicin (DOX)-induced acute heart failure animal model. This animal model is associated with an increase in oxidative stress and causes significant hepatopathy after DOX injection.

Specifically, 20-week-old male mice were injected intraperitoneally once with 20 mg/kg of DOX. A test group (DOX-PVAX) was injected intraperitoneally with 100 µg of the PVAX microparticles for 7 days, and a control group (DOX-saline) was injected intraperitoneally with the same amount of vehicle. Mortality was observed up to 10 days after DOX administration. After 10 days, the mice were sacrificed and the expressions of enzymes in the heart and liver tissues were analyzed. The cardiac function of the mice was also measured by echocardiogram. The results of the analysis are illustrated in FIGS. 29-36.

Figure 29:
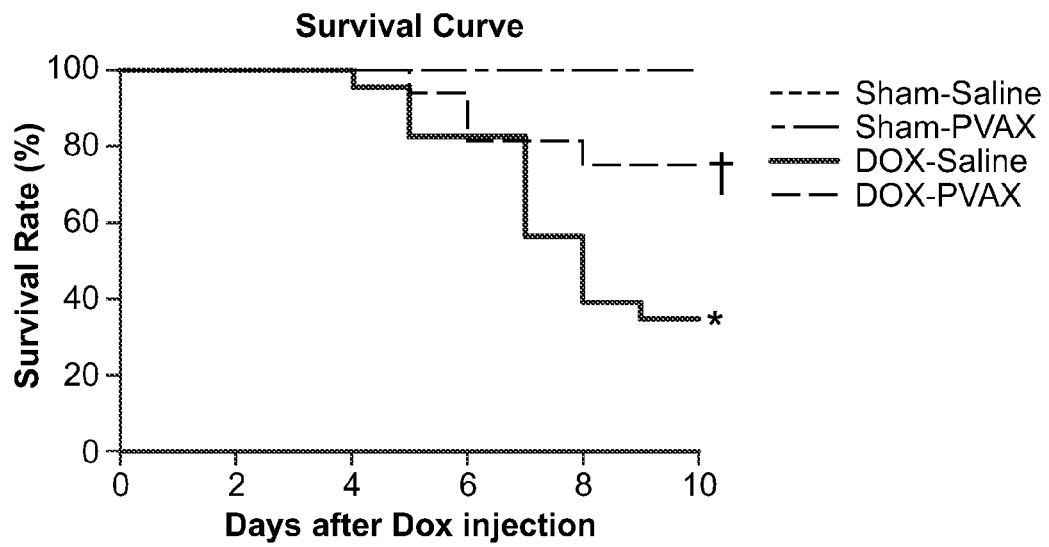
FIG. 29 is a bar graph illustrating the effect of PVAX microparticles on mouse survival rate in a doxorubicin (DOX)-induced acute heart failure model.
Figure 30:
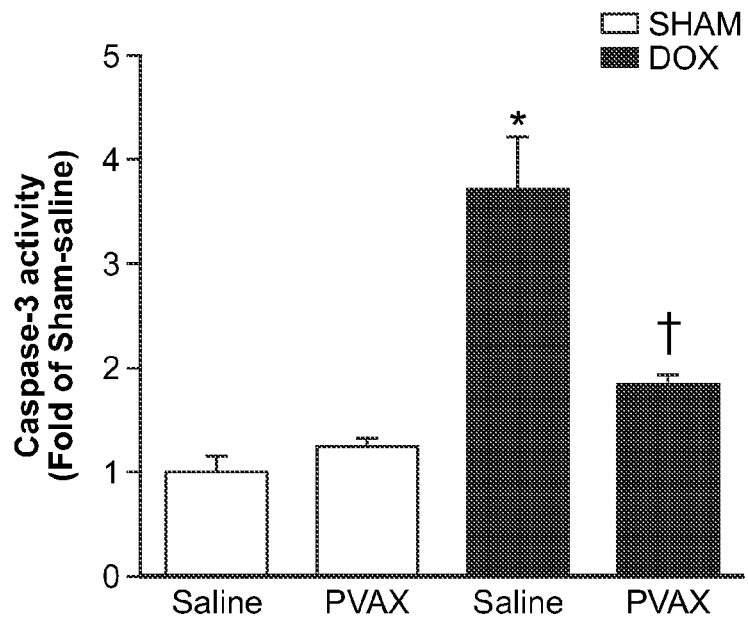
FIG. 30 is a bar graph and table illustrating the effect of PVAX microparticles caspase-3 enzyme activity in the heart of a DOX-induced acute heart failure model.
Figure 31:
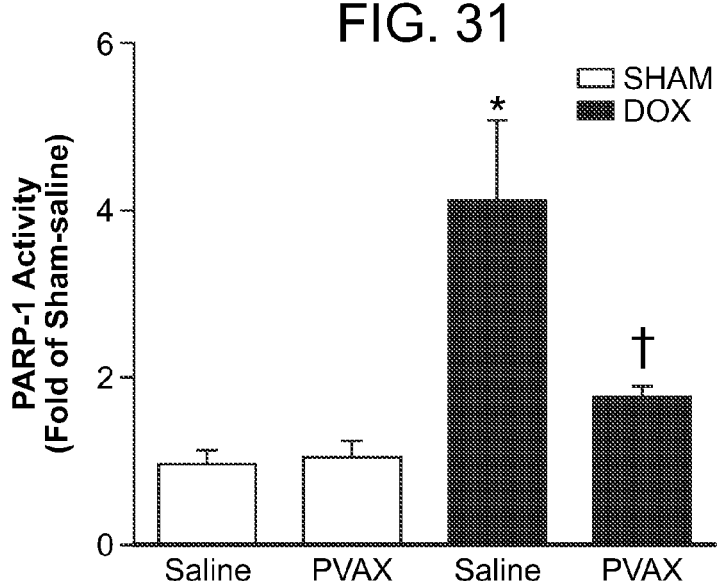
FIG. 31 is a bar graph and table illustrating the effect of PVAX microparticles on PARP-1 enzyme activity in the heart of DOX-induced acute heart failure model.
Figure 32:
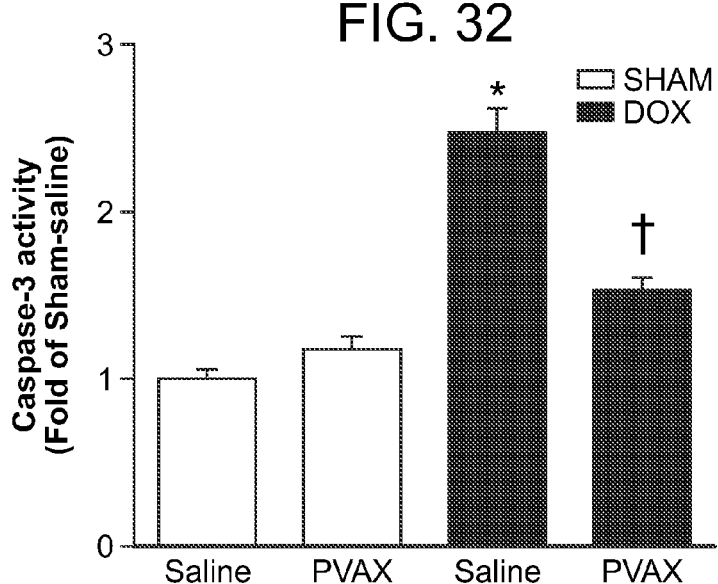
FIG. 32 is a bar graph and table illustrating the effect of PVAX microparticles on caspase-3 enzyme activity in the liver tissue of a DOX-induced acute heart failure model.
Figure 33:
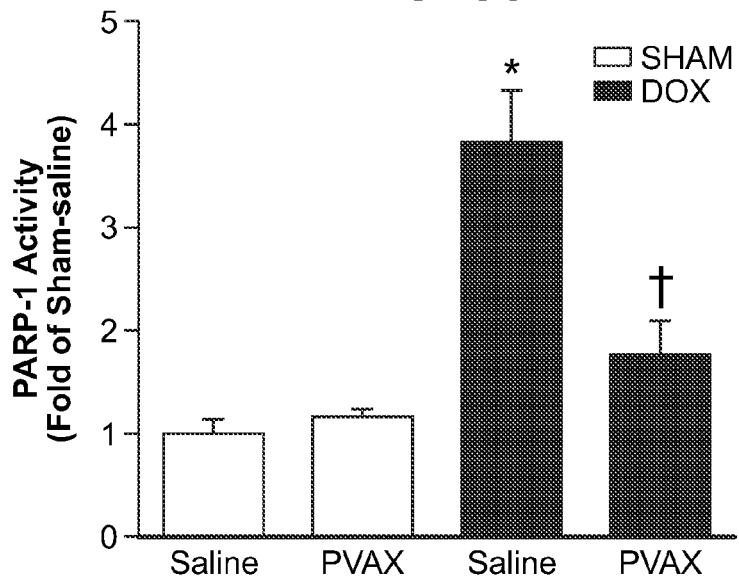
FIG. 33 is a bar graph and table illustrating the effect of PVAX microparticles on PARP-1 enzyme activity in the liver tissue of a DOX-induced acute heart failure model.

As illustrated in FIG. 29, 10 days after DOX injection, the mortality of the group injected with the PVAX microparticles significantly decreased. There were no differences in cardiac parameters at the beginning of the experiment, however during the observation period the animals in the DOX treated group showed mortality rate of 65%. The group that received daily doses of PVAX with initial DOX treatment revealed only 25% of mortality. This result demonstrates that PVAX improves survival outcome in animals that have DOX-induced cardiac injury (DOX only=35% vs, DOX with PVAX=75%; p<0.05).

As illustrated in FIGS. 30-33, in the heart and liver tissues of the group injected with the PVAX microparticles, the activities of the apoptosis-related enzymes PARP-1 and caspase-3 were significantly inhibited.

Figure 34:
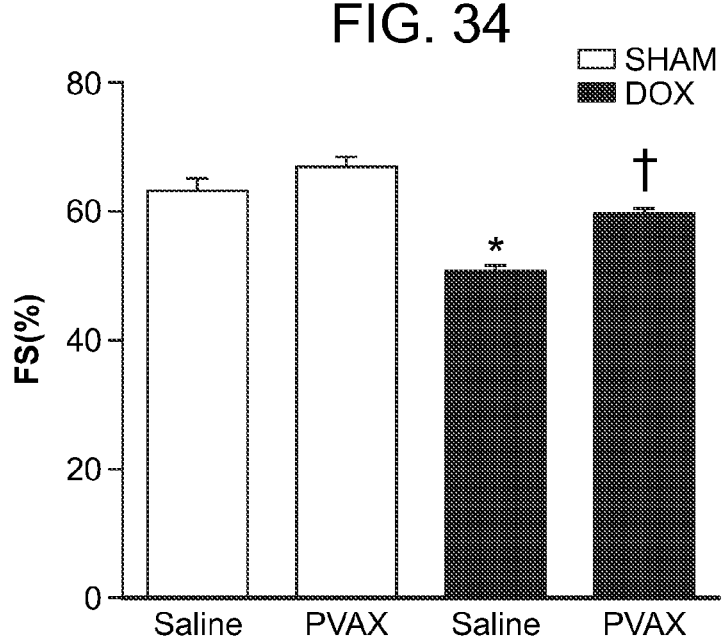
FIG. 34 is a bar graph illustrating the effect of PVAX microparticles on the heart function of a DOX-induced acute heart failure model, PVAX effect on fractional shortening (FS) is shown.
Figure 35:
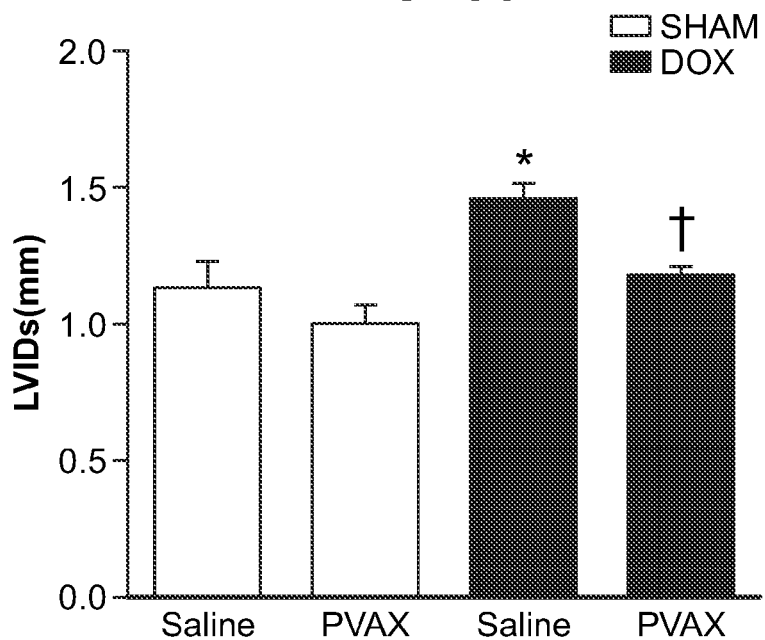
FIG. 35 is a bar graph illustrating the effect of PVAX microparticles on the heart function of a DOX-induced acute heart failure model. PVAX effect on LVIDS, a measure of left ventricular internal dimension in systole, is shown.

As illustrated in FIGS. 34-35, the cardiac functions (as measured by fractional shortening (FS) and left ventricle inner diameters (LVIDs)) of the group injected with the PVAX microparticles were improved.

Example 12: PVAX Microparticles for APAP-Induced Acute Liver Failure

MnP (manganese porphyrin) is a SOD (superoxide dismutase) mimic with anti-oxidative and anti-inflammatory activity. MnP was used as a model drug to evaluate the potential of PVAX microparticles as drug delivery systems using a mouse model of acute liver failure. MnP-loaded PVAX (MnP-PVAX) microparticles were prepared by a double emulsion method. APAP (acetaminophen) was used to induce acute liver failure.
Preparation of MnP-PVAX Microparticles
Five milligrams of MnP (manganese porphyrin) in 300 µL of deionized water were added into 1 mL of DCM (dichlomethane) containing 100 mg of PVAX, followed by sonication (Fisher Scientific, Sonic Dismembrator 500) for 30 seconds and homogenization (PRO Scientific, PRO 200) for 1 minute.

Figure 36A:
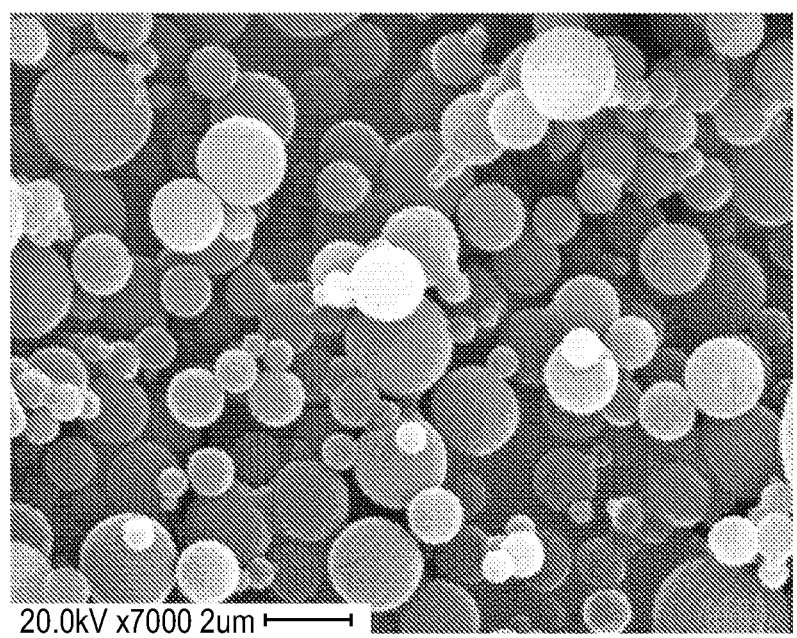
FIGS. 36A-36B, illustrates the characterization of MnP-PVAX microparticles.
Figure 36B:
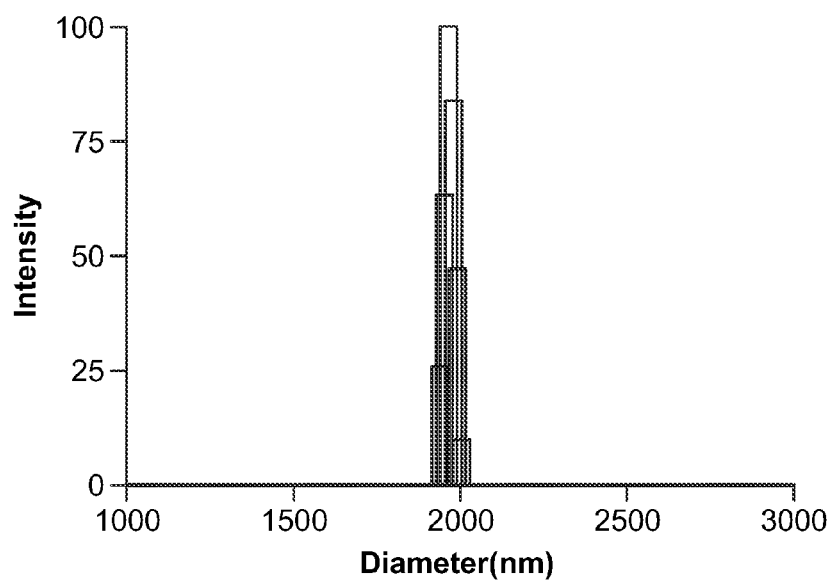
Figure 37:
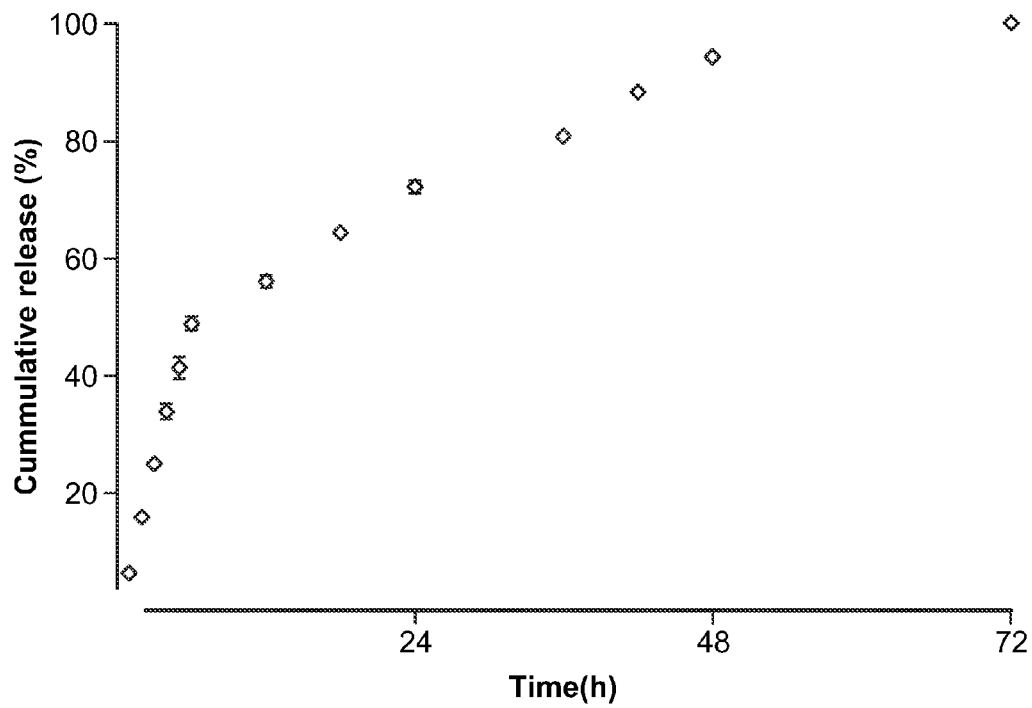
FIG. 37 is a graph illustrating the release kinetics of MnP from MnP-PVAX microparticles. At neutral conditions, 60% of MnP was released at 12 hours and most MnP was released at 48 hours.

The prepared w/o emulsion was added into 10 mL of 10% (w/w) aqueous PVA (polyvinyl alcohol) solution and the mixture was homogenized for 1 minute. The resulting w/o/w emulsion was stirred to evaporate the solvent for 3 hours at room temperature. Microparticles were obtained by the centrifugation at 8,000×g for 5 minutes at 4° C., followed by lyophilization of the recovered pellets.
Characterization of MnP-PVAX Microparticles
The shape of the PVAX microparticles was observed with a scanning electron microscope (SEM) (S-3000N, Hitachi, Japan), and the diameter of the microparticles was measured with a particle size analyzer (ELS-8000, Photal Otsuka Electronics, Japan). Results are illustrated in FIG. 36.
Drug Release Kinetics
10 mg of the MnP-PVAX microparticles were added to 2 ml of PBS (pH 7.4), followed by stirring at 37° C. At appropriate intervals, the stirred solution was centrifuged at 2,000×g for 5 minutes and 200 µl of the supernatant was taken and replaced with the same amount of fresh PBS. The concentration of MnP in the supernatant was determined using an UV spectrometer (S-3100, Scinco, Korea) at 466 nm and the release kinetics was analyzed. Results are illustrated in FIG. 37. In one embodiment, the fast release kinetics of PVAX microparticles allows for the treatment of diseases that need fast therapeutic actions, such as acute liver failure.
MTT Assay
In order to analyze the cytotoxicity of the PVAX or MnP-PVAX microparticles, a MTT [3-(4,5-dimethylthiazol-2-yl)-2,5-diphenyltetrazolium bromide] assay was carried out.

Figure 38:
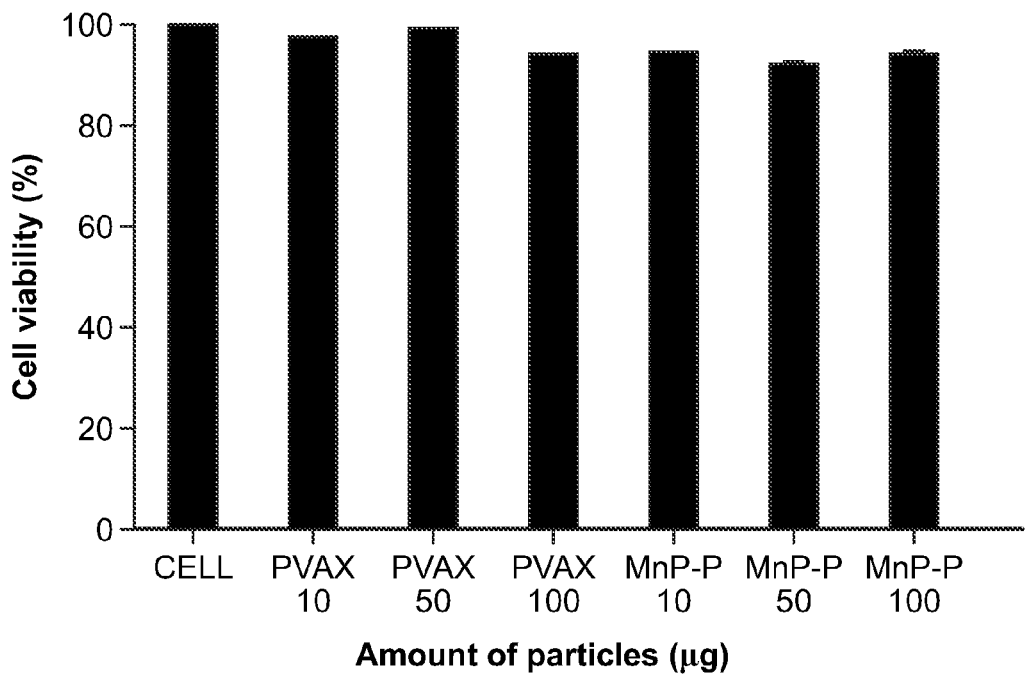
FIG. 38 is a bar graph illustrating the cytotoxicity of MnP-PVAX microparticles. PVAX or MnP-PVAX microparticles showed no or minimal toxicity on RAW 264.7 cells after 24 hours of incubation (MnP-P=MnP-PVAX).
Figure 39:
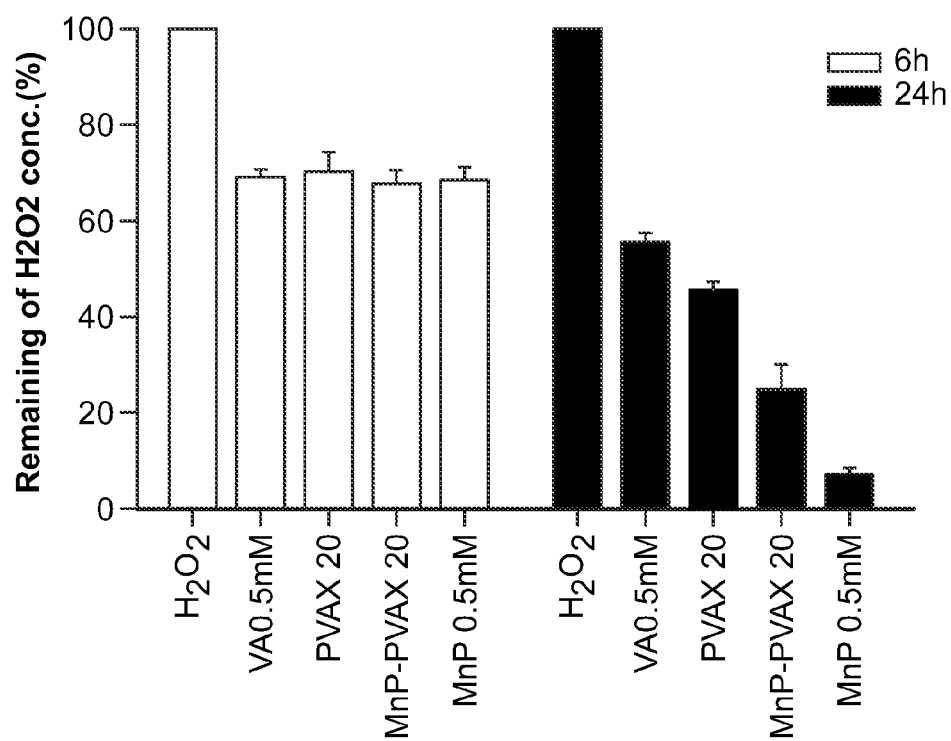
FIG. 39 is a bar graph illustrating the scavenging of $H_2O_2$ by PVAX or MnP-PVAX microparticles.

Specifically, RAW 264.7 cells were seeded in a 24-well plate at a density of $3\times10^5$ cells/well, and cultured for 24 h. The cells were treated with various concentrations of PVAX or MnP-PVAX microparticles (10~100 µg), and then incubated for 24 hours. The medium was removed, and 20 µl of a MTT reagent was added to each well, followed by incubation for 4 hours. 200 µl of DMSO (dimethyl sulfoxide) was added to each well and incubated for 30 minutes, after which the absorbance at 570 nm was measured using a microplate reader (Synergy MX, BioTek Instruments, US). The cell viability was analyzed by comparing the absorbance of PVAX microparticles-treated cells to that of control cells. Results are illustrated in FIG. 38 and suggest that the composition may be used in a biomedical application.
$H_2O_2$ Scavenging
1 ml of 10 µM $H_2O_2$ solution was treated with 1 mg of PVAX or MnP-PVAX microparticles and incubated with stirring at 37° C. for 6 or 24 h. After short centrifugation, the concentration of $H_2O_2$ in the supernatant was measured using an amplex red assay (Invitrogen, US). Results are illustrated in FIG. 39. PVAX and MnP displayed $H_2O_2$ scavenging activity in a time-dependent manner. MnP-PVAX microparticles displayed a greater $H_2O_2$ scavenging activity than empty PVAX microparticles.
Inhibitory Effects of MnP-PVAX Microparticles on ROS Generation
The inhibitory effect of the MnP-PVAX microparticles on the production of ROS in RAW 264.7 cells activated with LPS (lipopolysaccharide) was analyzed.

Figure 40:
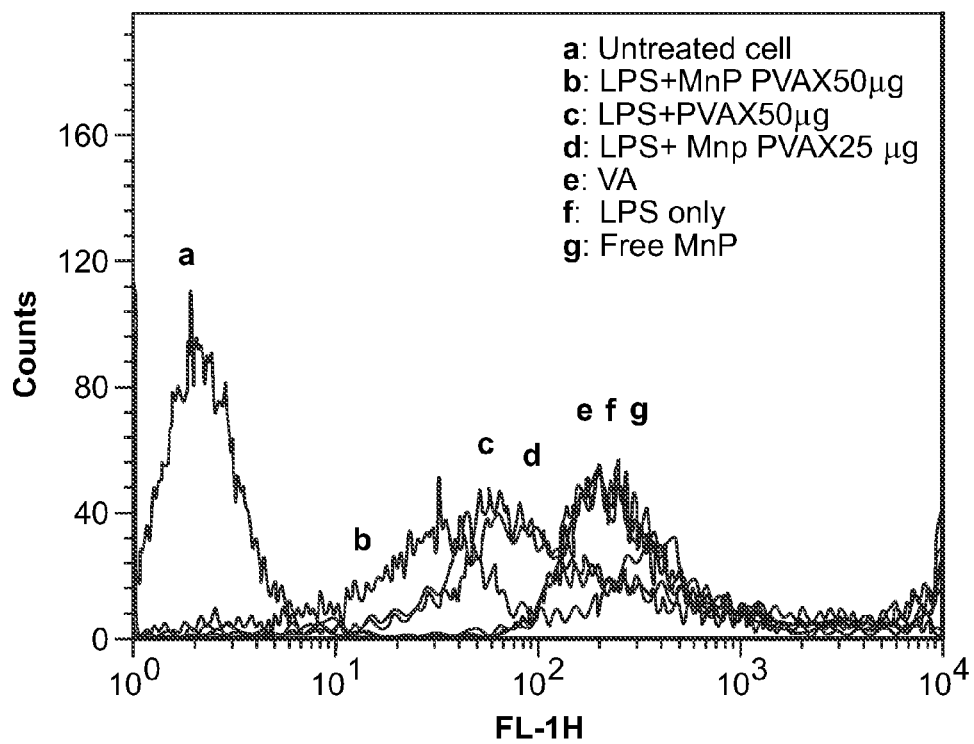
FIG. 40 is a graph illustrating the inhibitory activity of MnP-PVAX on ROS generation in RAW 264.7 cells treated with LPS.

Specifically, RAW 264.7 cells were treated with 25 or 50 µg of the PVAX microparticles and incubated for 24 h. The cells were treated with LPS (1 µg/ml) to stimulate the production of ROS in cells, and after 24 h, the cells were treated with DCFH-DA (dichlorofluorescin-diacetate), after which DCF (dichlorodihydrofluorescein), a marker of intracellular oxidative stress, was analyzed using a flow cytometer (Becton Dickinson, US). Results are illustrated in FIG. 40. MnP-PVAX microparticles showed a higher inhibitory activity on ROS generation than empty PVAX microparticles.

Inhibitory Effects of NO Production

Figure 41:
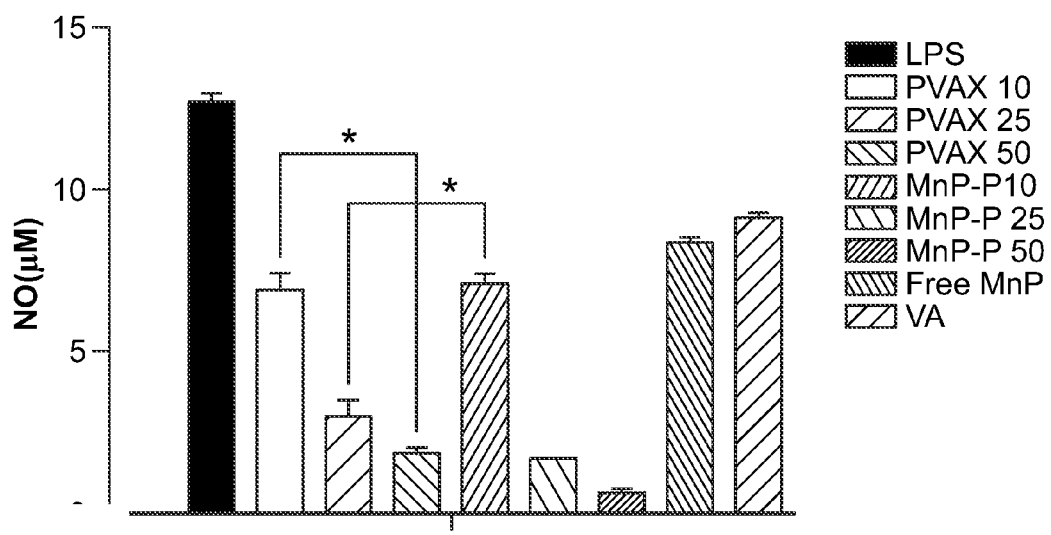
FIG. 41 is a bar graph illustrating the inhibitory effects of MnP-PVAX microparticles on nitric oxide (NO) production. *p<0.05.

RAW 264.7 cells ($3 \times 10^5$ cells/well in a 24 well plate) were pretreated with a various amount of PVAX or MnP-PVAX microparticles for 24 hours, and then treated with 1 µL of LPS (1 mg/mL) for 24 hours. The concentration of NO was determined using a colorimetric assay based on the Griess reaction. 50 µL of cell culture medium was collected and given 100 µL of Griess reagent (6 mg/mL) at room temperature for 10 min, and then the NO concentration was determined by measuring the absorbance at 540 nm using a microplate reader (Synergy MX, BioTek Instruments, US). The NO standard curve was constructed using known concentrations of sodium nitrite. Results are illustrated in FIG. 41. VA and MnP showed inhibitory effects on NO production, not significant. PVAX showed highly potent inhibitory effects on NO production. However, MnP-PVAX microparticles showed higher inhibitory effects than empty PVAX microparticles.

Anti-Inflammatory Activity

Figure 42:
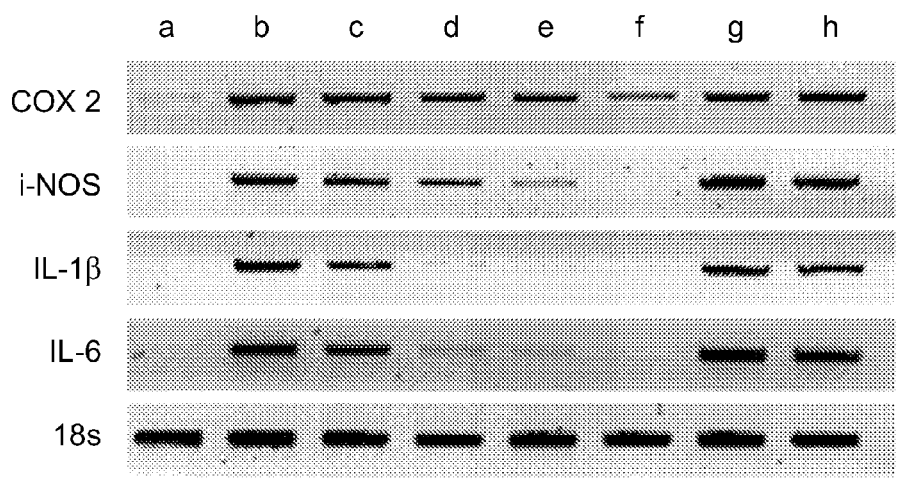
FIG. 42 is a set of gel photographs illustrating anti-inflammatory effects of MnP-PVAX microparticles in LPS-stimulated cells. Lanes: (a) Control, (b) LPS 1 µg/ml, (c) PVAX 25 µg, (d) PVAX 50 µg, (e) MnP-PVAX 25 µg, (f) MnP-PVAX 50 µg (g) Free MnP, (h) VA (0.5 mM).
Figure 43A:
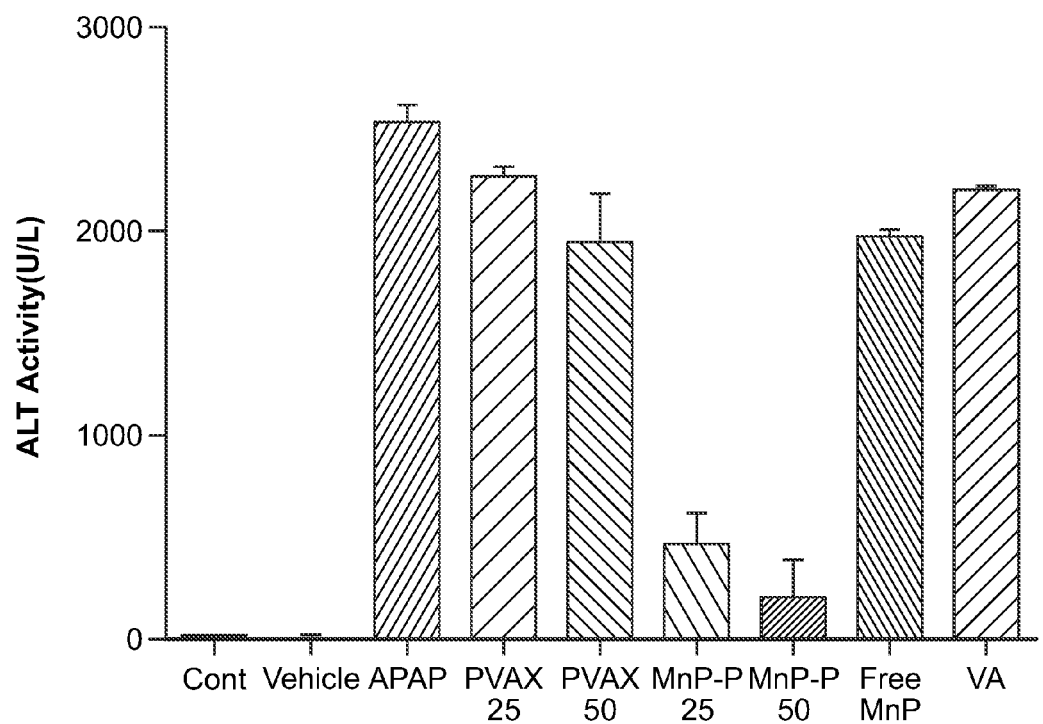
FIGS. 43A-43C, illustrates the effects of PVAX microparticles on acetaminophen (APAP)-intoxicated mice.
Figure 43B:
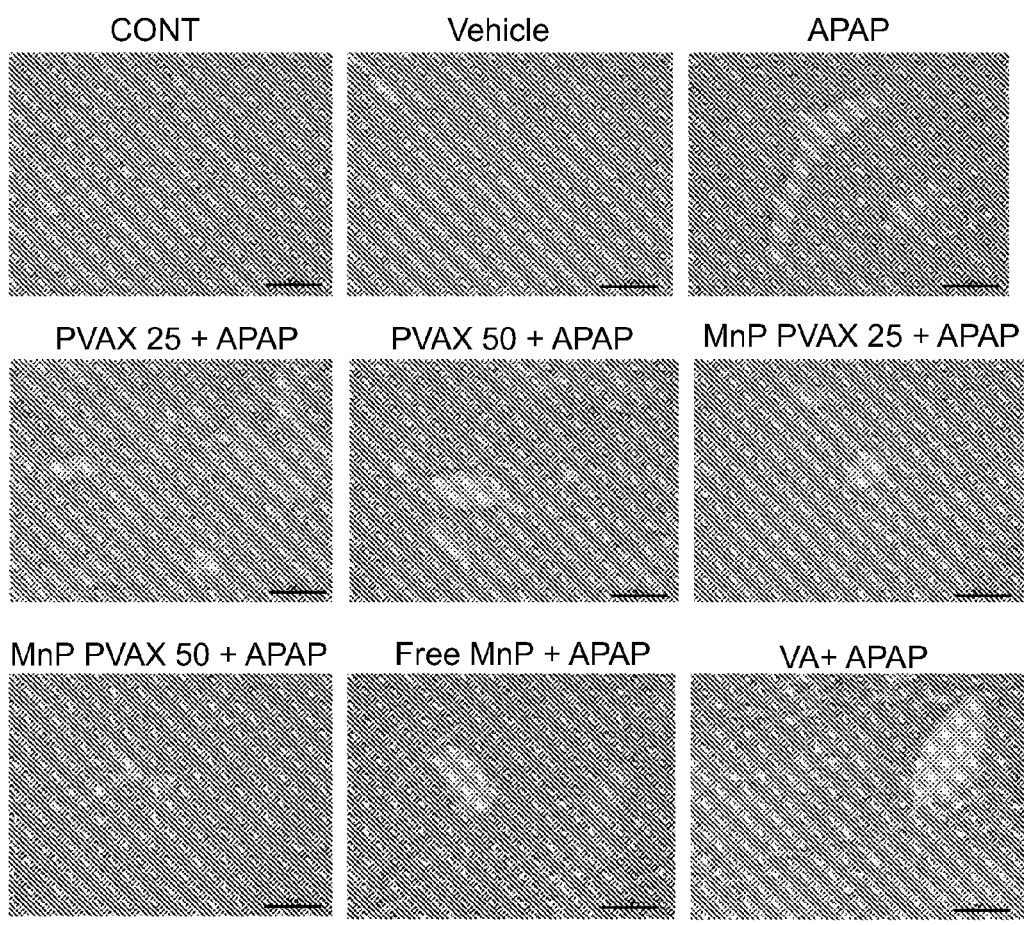
Figure 43C:
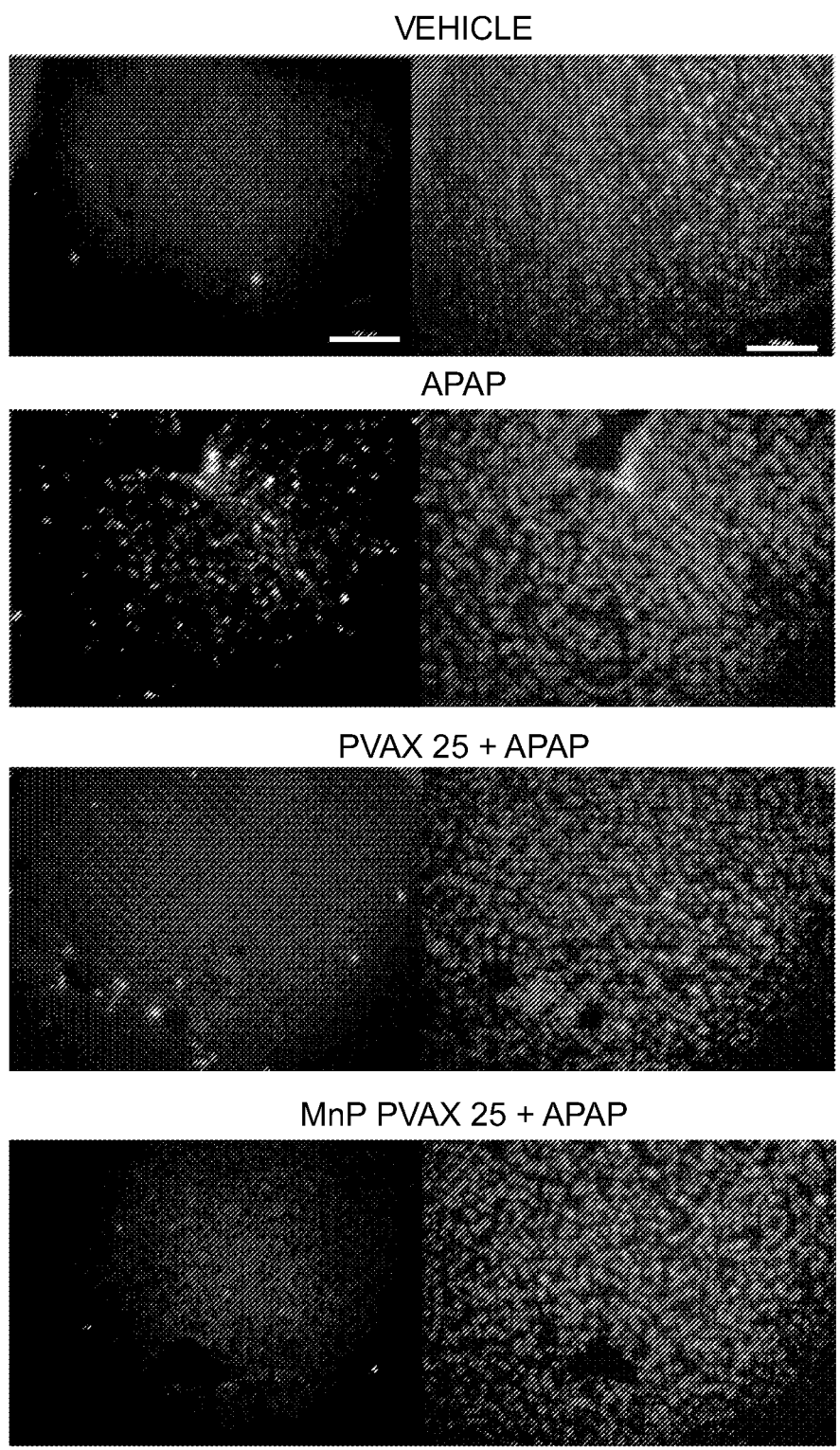

RAW 264.7 cells ($3 \times 10^5$ in a 24 well culture plate) were pretreated with 1 µL of LPS (1 mg/mL) for 4 h. PVAX or MnP-PVAX microparticles were given to cells and cells were incubated for 20 h. Total cellular RNA was isolated using 1 mL of Trizol (Invitrogen, Life Technologies Co, Groningen, Netherlands) and 0.2 mL of chloroform. Three microgram of total RNA was reverse-transcribed into cDNA using oligo (dT) primer (Invitrogen), 5× First Strand buffer (Invitrogen), dNTP (dGTP, dATP, dTTP, dCTP, Gibco), RNase inhibitor (Invitrogen), SuperScript II (Invitrogen), RNase H reverse transcriptase (Invitrogen) and DNase/RNase free water (Gibco, Gland Island, N.Y.). PCR was performed on aliquots of the cDNA preparations to detect COX-2, iNOS, IL-1β and IL-6 and 18S (the internal standard) gene expressions by Authorized Thermal Cycler (TP 600, Takara Bio Inc, Japan). After amplification, portions of the PCR reactions were subjected to electrophoresis using 2% agarose gel and visualized under UV (365 nm) after ethidium bromide staining. Results are illustrated in FIG. 42. PVAX suppressed the expression of COX-2, iNOS, IL-1β and IL-6 PVAX in a dose-dependent manner. However, MnP-PVAX microparticles showed higher anti-inflammatory effects than PVAX microparticles.

Mouse Model of APAP-Induced Acute Liver Failure

Mice (~20 g) were fasted for 12 h prior to the experiments. VA, MnP, PVAX or MnP-PVAX microparticles (0.75 mg/kg) were injected to mice (n=4) through a tail vein. After 1 hour, acute liver failure was induced by the intraperitoneal injection of 200 µL of APAP (25 mg/mL). Mice were sacrificed 24 hours after APAP intoxication, and whole blood and livers were collected. The activity of serum ALT was determined with an ALT enzymatic assay kit (Asan Pharma, Seoul, Korea) using a microplate reader (Synergy MX, BioTek Instruments, Inc, Winooski, Vt.). The liver tissues were fixed with 10% formalin (Sigma-Aldrich, St. Louis, Mo.) and embedded into paraffin. Histological sections were made and stained with hematoxylin and eosin (H&E). Apoptotic cells were observed by TUNEL (Terminal deoxynucleotidyl transferase dUTP nick end labeling) staining. PVAX showed moderate therapeutic activity. However, MnP-PVAX microparticles suppressed the ALT activity and cellular damages more effectively than PVAX microparticles. Less apoptotic cell death induced by APAP intoxication was observed with a MnP-PVAX treated group.

Example 13: PVAX Microparticles for Allergic Airway Inflammatory Diseases

Ovalbumin (OVA) was used to induce allergic asthma in mice and dexamethasone (Dex) was used as a model drug to evaluate the potential of PVAX as drug delivery systems. The therapeutic activities of Dex-loaded PVAX (Dex-PVAX) microparticles were studied in vitro as well as in vivo.

Preparation of Porous Dex-PVAX Microparticles 5 mg of Dex was added to 1 mL of DCM containing 100 mg of PVAX. Ammonium bicarbonate (10 mg) was dissolved in deionized water, followed by sonication (Fisher Scientific, Sonic Dismembrator 500) for 30 seconds and homogenization (PRO Scientific, PRO 200) for 1 minute.

Figure 44A:
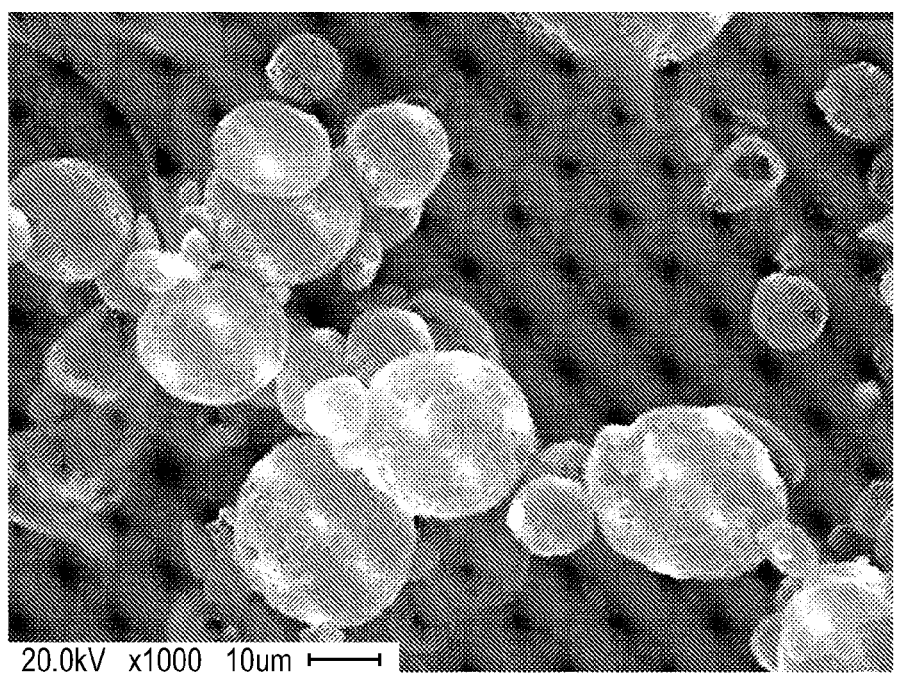
FIGS. 44A-44B, is a set of representative SEM images of porous PVAX microparticles.
Figure 44B:
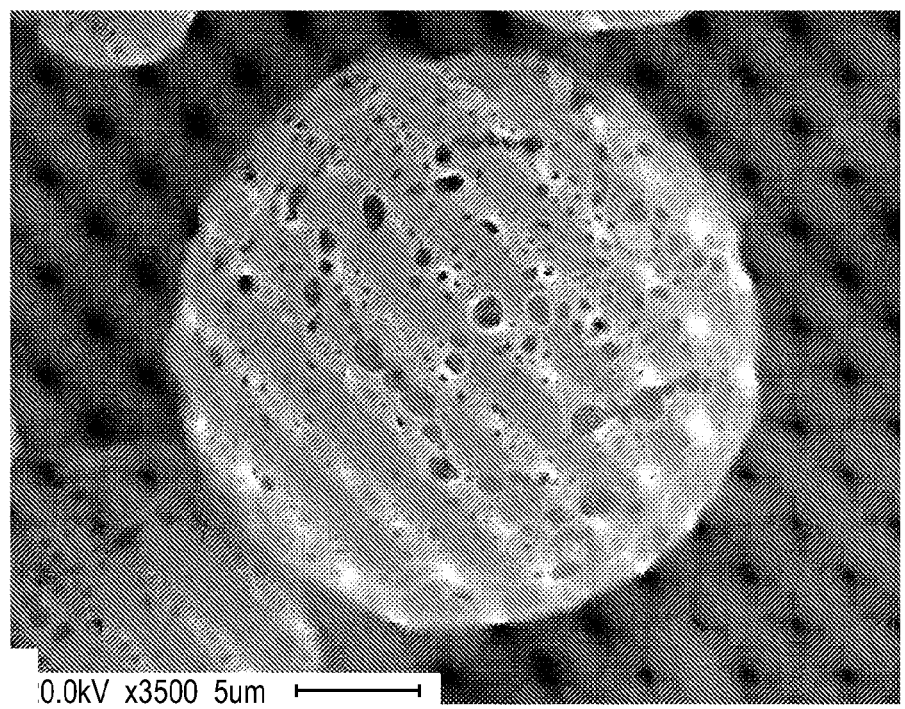

The prepared w/o emulsion was added into 10 mL of 10% (w/w) aqueous PVA (polyvinyl alcohol) solution and the mixture was homogenized for 1 minute. The resulting w/o/w emulsion was stirred to evaporate the solvent for 3 hours at room temperature. Microparticles were obtained by the centrifugation at 8,000×g for 5 minutes at 4° C. followed by lyophilization of the recovered pellets. The size and surface of Dex-PVAX microparticles were observed using a scanning electron microscope. Results are illustrated in FIG. 44. Dex-PVAX microparticles displayed a number of pores and were in the range of 10-20 µm in diameter.

Figure 45:
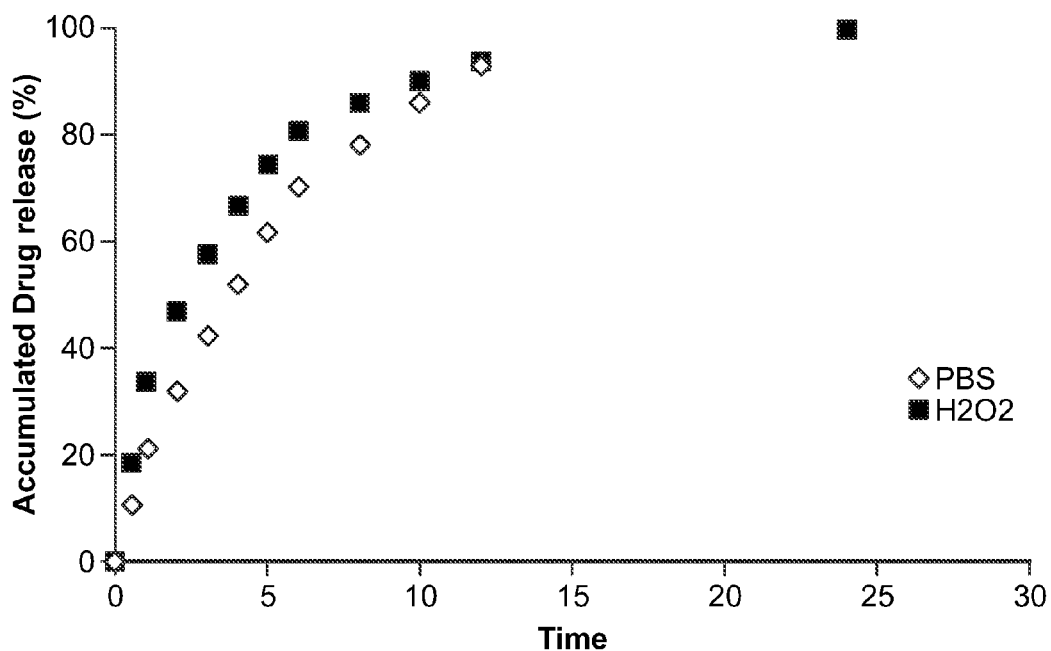
FIG. 45 is a graph illustrating the release of dexamethasone (Dex) from dexamethasone-PVAX porous microparticles.

Drug Release Kinetics 12.5 mg of porous Dex-PVAX microparticles were added into 10 mL of PBS (pH 7.4) with or without 1 mM of $H_2O_2$, followed by stirring at 37° C. At appropriate intervals, the stirred solution was centrifuged at 1,667×g for 5 minutes and 1 mL of the supernatant was taken and replaced with the same amount of fresh PBS. The concentration of Dex in the supernatant was determined using an UV spectrometer (S-3100, Scinco, Korea) at 466 nm and the release kinetics was analyzed. Results are illustrated in FIG. 45. Porous PVAX microparticles showed a fast drug release profile due to fast hydrolysis of PVAX and high porosity, with 50% release at 5 hours under physiological condition. In the presence of $H_2O_2$, Dex release was accelerated.

Cytotoxicity Determined by MTT Assay

Figure 46:
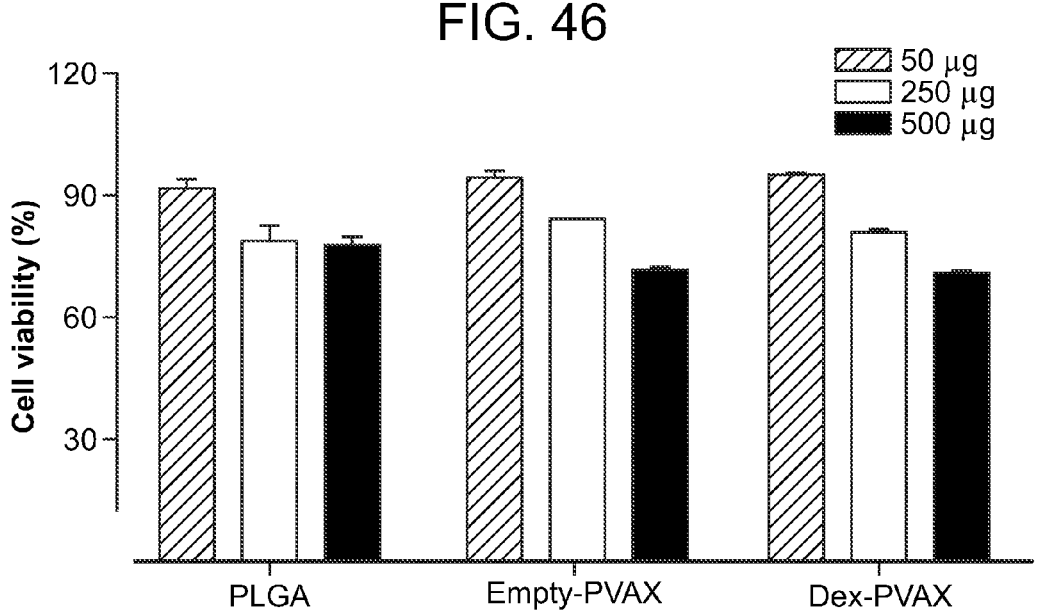
FIG. 46 is a bar graph illustrating the cytotoxicity of porous PVAX microparticles determined by MTT [3-(4,5-dimethylthiazol-2-yl)-2,5-diphenyltetrazolium bromide] assay.

Results are illustrated in FIG. 46. Porous PVAX and Dex-PVAX microparticles showed minimal cytotoxicity to RAW 264.7 cells at concentrations less than 500 µg/mL, comparable to PLGA microparticles.

Lung Biocompatibility

Figure 47:
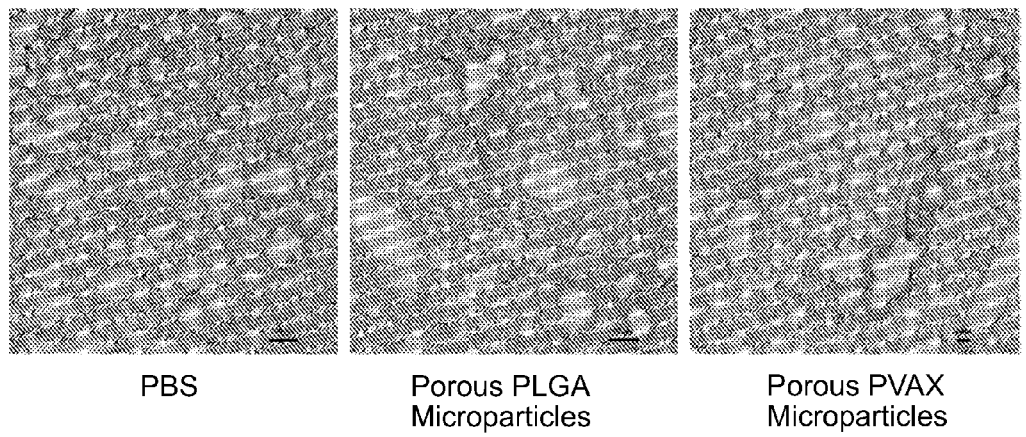
FIG. 47 is a set of figures illustrating biocompatibility of porous PVAX microparticles.

Porous microparticles (PLGA and PVAX) of equivalent physical characteristics were suspended in sterile saline at a concentration of 1 mg/mL. BALB/C mice (~20 g, Orient Bio, Korea) were anesthetized using isoflurane (Hana Pharma, Korea). A small incision was made to expose the trachea. The trachea was punctuated using a sterile syringe and 50 µL of particle suspension were injected. After injection, mice were sutured and allowed to recover. After mice were sacrificed on day 5, lung tissues were collected and stained using heamatoxylin and eosin. Mice were given porous PLGA or PVAX microparticles intratracheally at a dose of 2.5 mg/kg. Results are illustrated in FIG. 47.

Porous PLGA microparticles induced inflammatory responses, evidenced by the infiltration of leukocytes and airway thickening. However, porous PVAX microparticles induced minimal or no inflammation, demonstrating great biocompatibility and potential for inhalable drug delivery systems.

Mouse Model of Allergic Asthma

Figure 48:
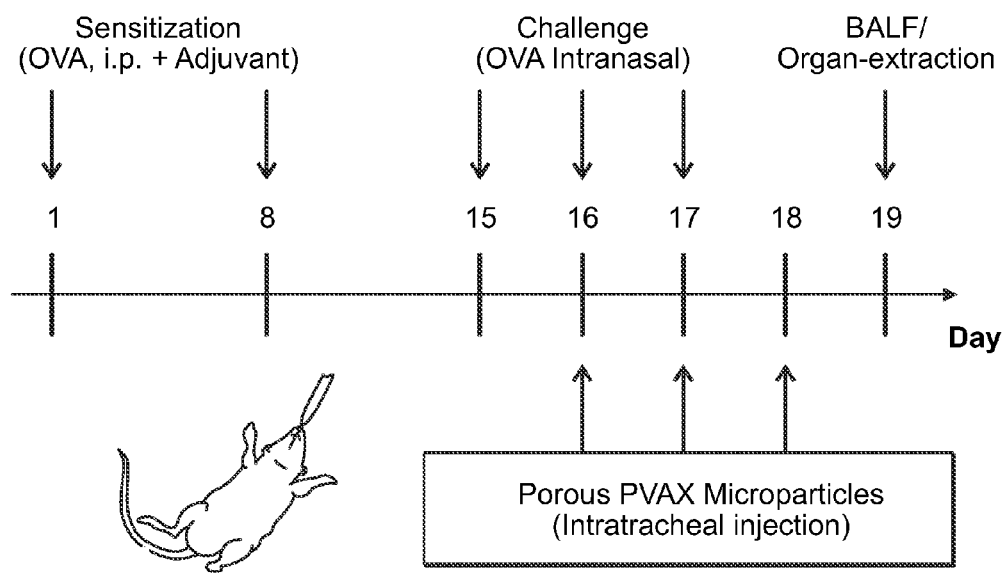
FIG. 48 is a schematic illustration of a protocol for a mouse model of ovalbumin (OVA)-induced allergic asthma.

As illustrated in FIG. 48, BALB/c mice (n=4) anesthetized under isoflurane were sensitized by intraperitoneally with 75 µg ovalbumin (OVA, Sigma-Aldrich, St. Louis. Mo.) and 2 mg of aluminum hydroxide (Sigma-Aldrich, St. Louis, Mo.) dissolved in 200 µL phosphate buffered saline (PBS) on days 1 and 8. On days 15, 16 and 17, mice were challenged intranasally with 50 µg of OVA. PVAX microparticles (25 or 50 µg) were injected mice intratracheally on days 16, 17 and 18. A sham group was given PBS only. On day 19, the mice were sacrificed and lung lobes were isolated along with the trachea.

Lungs were also lavaged with 500 µL of PBS introduced through the trachea. BALF (bronchiolavage fluid) was centrifuged at 300×g for 5 min, and cells were rinsed and resuspended with PBS. Aliquots of the cell suspension were applied to slides by Cytospin (Hanil, Korea) at 500×g for 5 minutes allowed to air dry and stained with modified Wright's stain (Hema-3, Fisher Scientific). The numbers of macrophages, eosinophils, neutrophils and lymphocytes were determined morphologically and a minimum of 200 cells per slide were counted under the microscope (Eclipse, Nikon, Japan). The level of TNF-α in the supernatant of BALF was measured with an ELISA kit as advised by manufacturer (eBioScience, San Diego, Calif.). Lungs were perfused with PBS, removed and fixed in 4% buffered formalin. Lungs were embedded in paraffin and serial paraffin sections (3 µm) were cut. The sections were stained with hematoxylin (Yeongdong Pharma, Korea) and eosin (Showa Chemicals, Japan). Results are illustrated in FIGS. 49-51.

Figure 49:
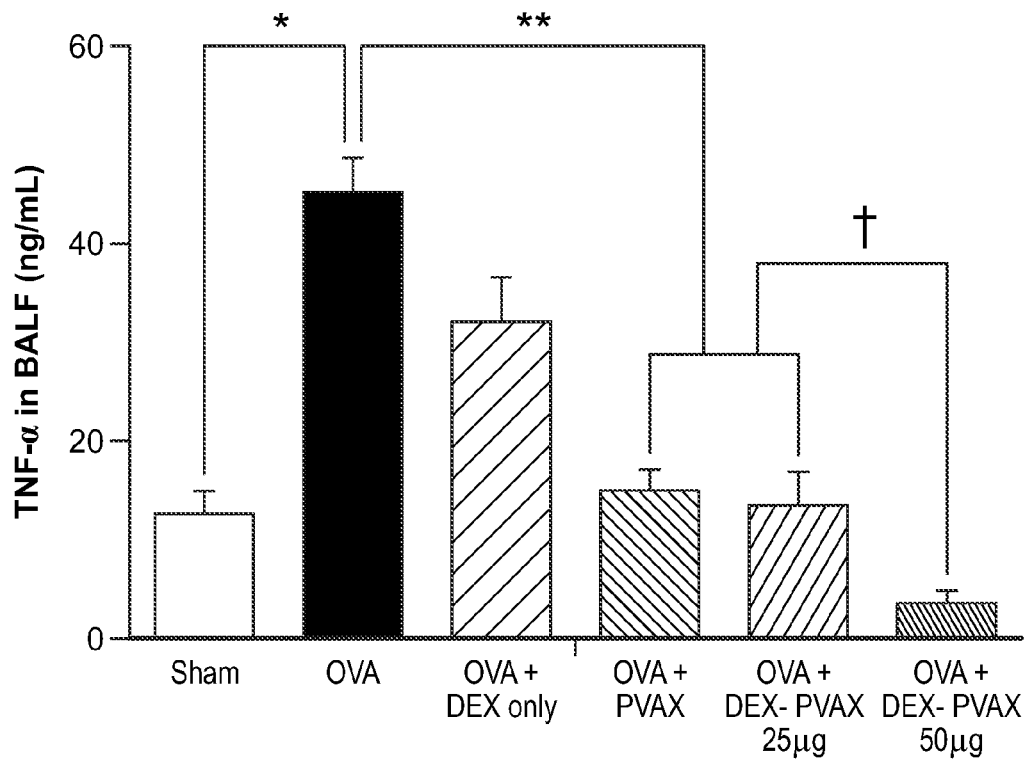
FIG. 49 is a bar graph illustrating the enhanced anti-inflammatory activity of dexamethasone-PVAX microparticles on OVA-induced allergic airway inflammation.
Figure 50A:
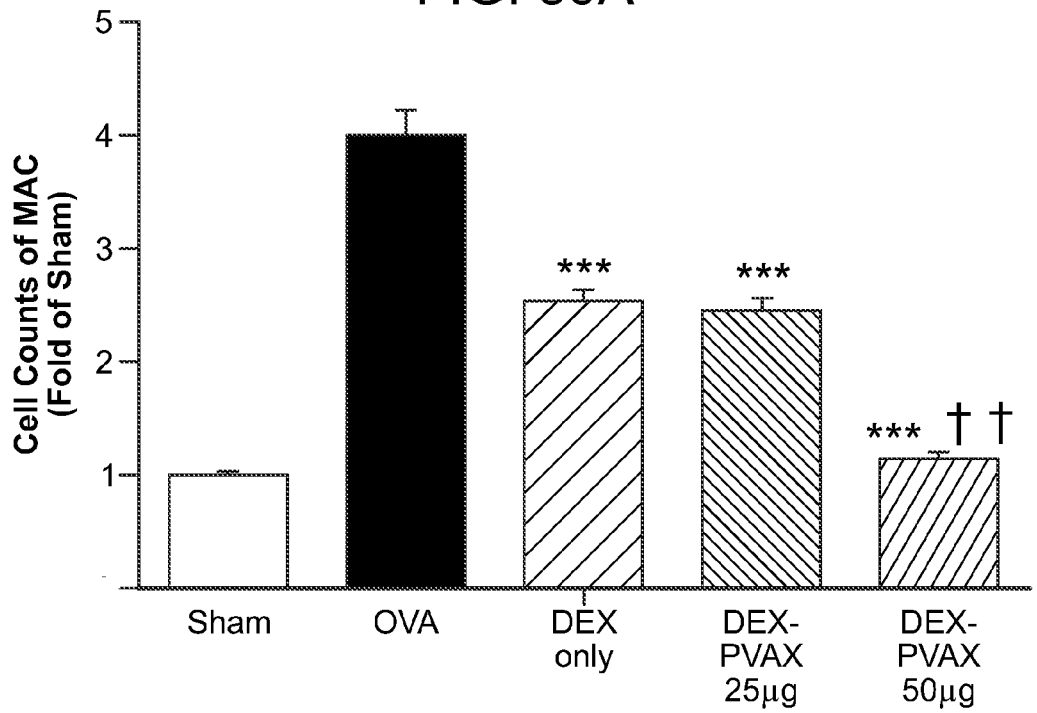
FIGS. 50A-50D, is a set of bar graphs illustrating the effects of dexamethasone-PVAX microparticles on inflammatory cell populations in BALF of OVA-sensitized and challenged mice. ***p<0.001 relative to OVA, †p<0.01, ††p<0.001 relative to dexamethasone.
Figure 50B:
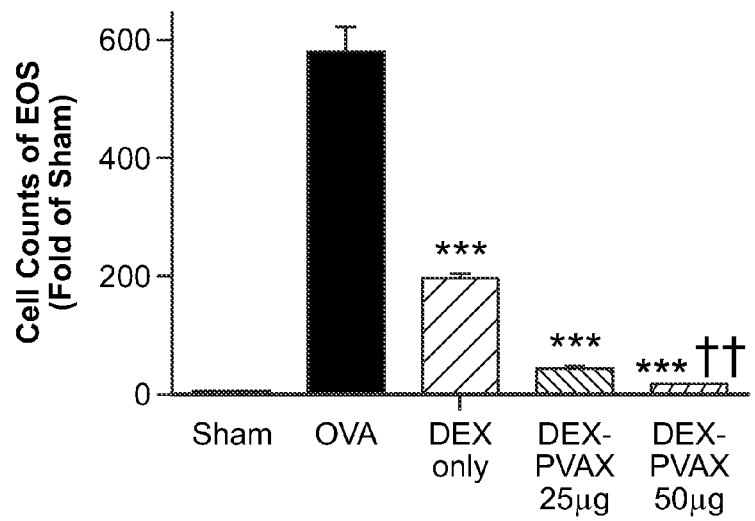
Figure 50C:
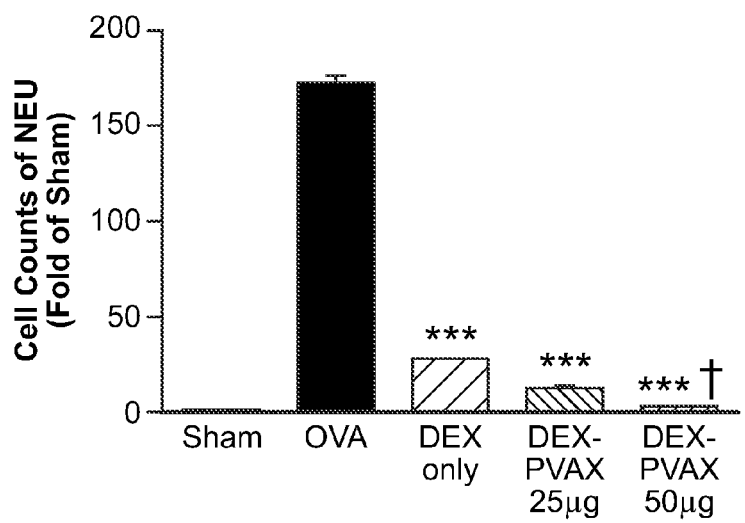
Figure 50D:
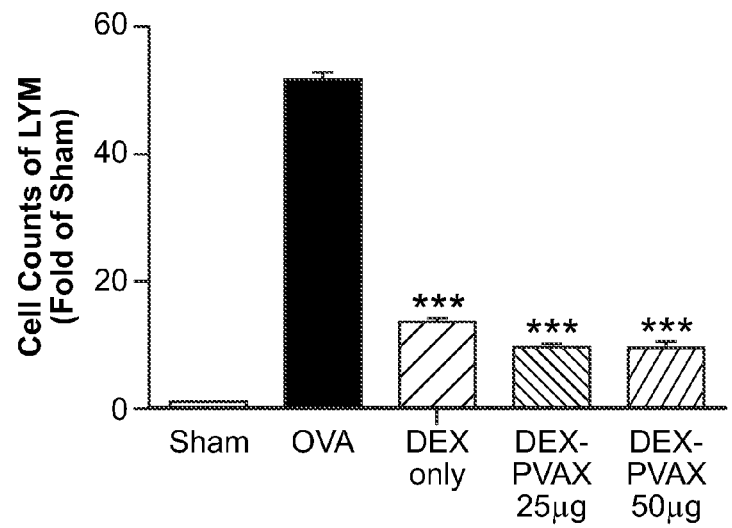

As illustrated in FIG. 49, OVA sensitization and challenge increased the expression of pro-inflammatory TNF-α in BALF. PVAX and VA suppressed the expression of TNF-α. A dose of 25 µg of Dex-PVAX microparticles showed the same extent of anti-inflammatory activity as 50 µg of PVAX microparticles. PVAX microparticles at a dose of 50 µg remarkably reduced the expression of TNF-α. Results demonstrate the synergistic anti-inflammatory activity of PVAX microparticles with a payload of Dex.

As illustrated in FIG. 50, OVA sensitization and challenge increased the number of inflammatory cells, macrophages (MAC), eosinophils (EOS), lymphocytes (LYM) and neutrophils (NEU). Anti-inflammatory drug Dex reduced the inflammatory cell recruitment significantly. However, Dex-PVAX microparticles showed more potent inhibitory effects of inflammatory cell recruitment, demonstrating the great potential of PVAX as a drug delivery system and synergistic effects with Dex.

Figure 51:
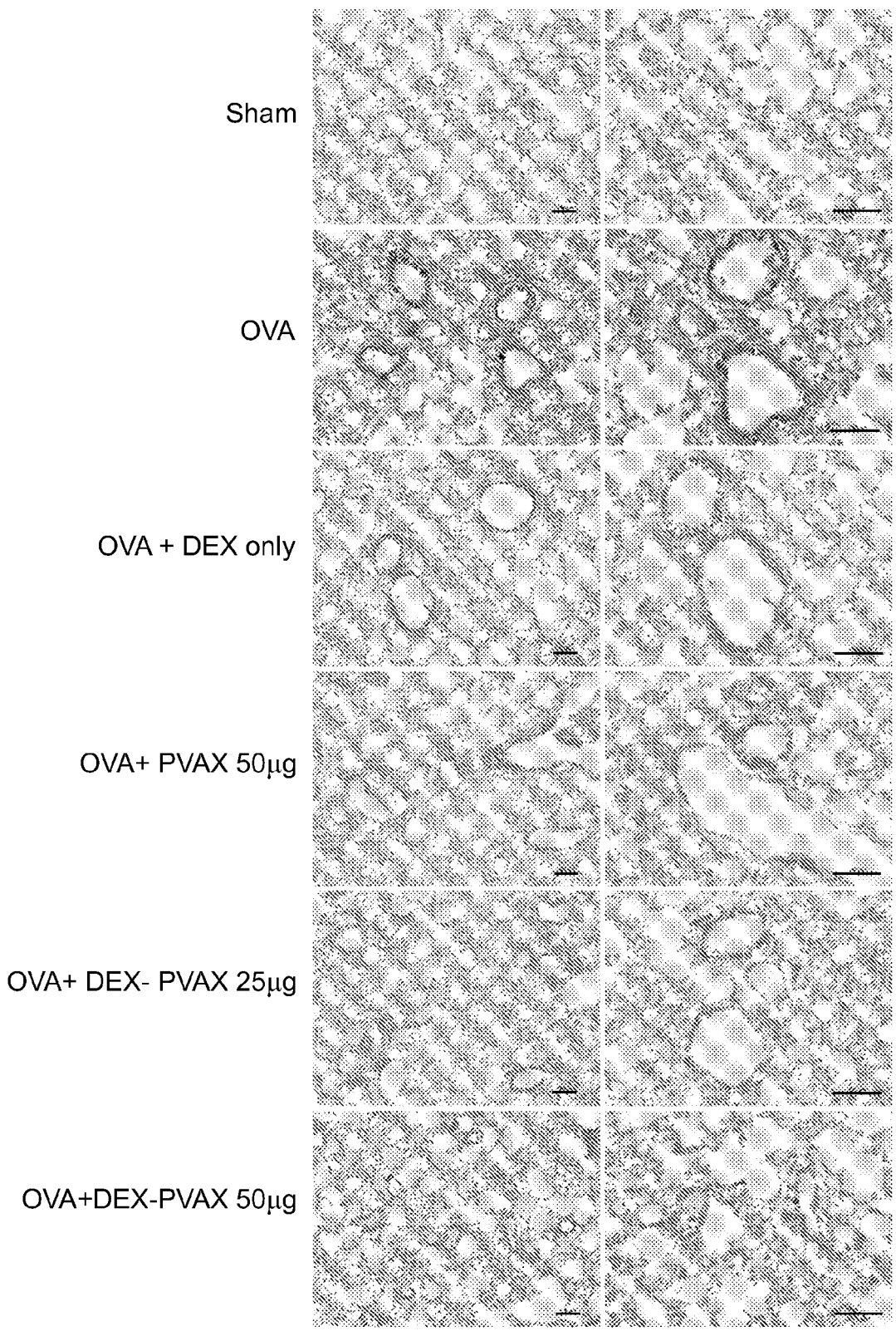
FIG. 51 is a set of photographs illustrating H&E staining of lung of OVA sensitized and challenged mice.

As illustrated in FIG. 51, OVA sensitization and challenge induced severe peribronchial inflammation and airway remodeling, such as airway thickening and a massive infiltration of inflammatory cells. A group of mice treated with Dex or PVAX alone showed reduced inflammatory responses. However, Dex-PVAX microparticles exhibited remarkable reduction of airway remodeling and inflammatory responses, in a dose dependent manner.

Figure 56:
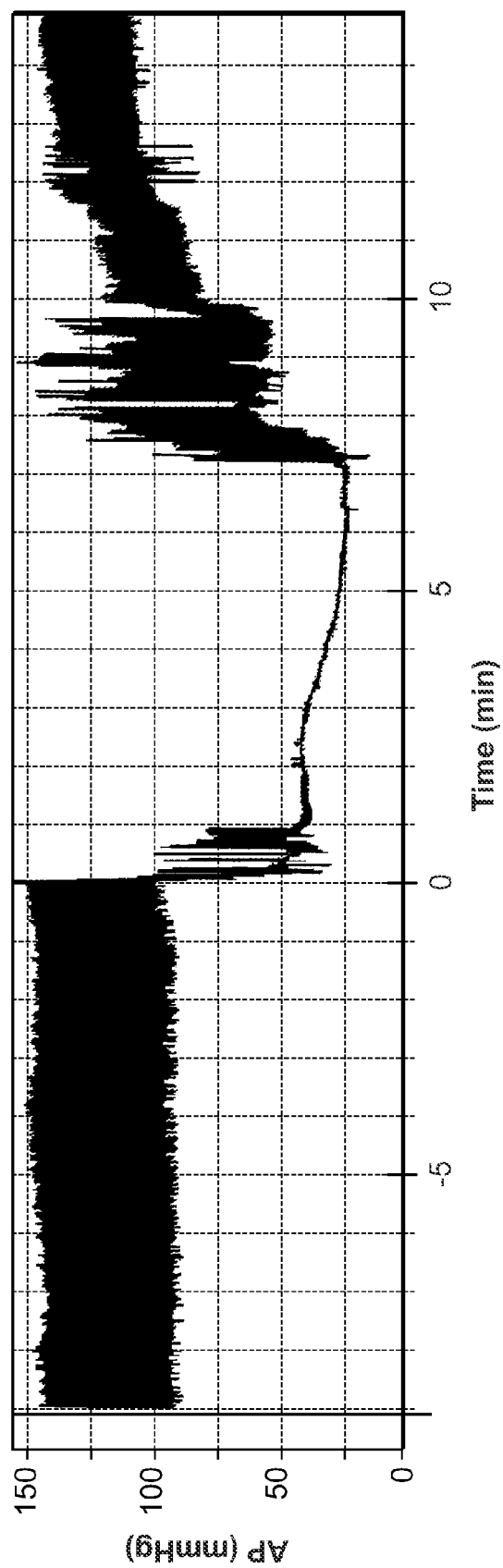
FIG. 56 is a graph illustrating the KCl-induced murine whole body CAR I/R injury model.

Example 14: Therapy for Cardiac Arrest/Resuscitation (CAR) Reperfusion Injury In Vivo A model of whole body ischemia/reperfusion, which would closely mimic CPB reperfusion injury, was developed. Whole body CAR reperfusion was induced by infusion of KCl (25 mEq/L) and discontinuation from the ventilation, which resulted in rapid loss of blood pressure (FIG. 56). Resuscitation protocol was initiated 6 minutes after of cardiac arrest by reconnecting the ventilation, CPR and epinephrine injection (20 µl/g). Resuscitation protocol was continued till restoration of spontaneous circulation. Resuscitation was abandoned if spontaneous circulation was not achieved within 5 minutes. Inflammatory marker TNF-<from various tissues, such as brain, heart and the kidneys, were increased in these tissues after CAR.

Example 15: Safety Profile of PVAX in Rodents

The safety profile of PVAX was determined through administration of 3 mg/kg of PVAX daily for 7 days in mice. Serum tests for renal and hepatic function showed no significant abnormalities after 7 days. In addition, there was no obvious histological evidence of accumulated toxicity in the different organs associated with administration of PVAX for 7 days, demonstrating the excellent in vivo biocompatibility of PVAX.

Example 16: Comparison of PVAX and HPOX at 20% Mole Fraction

HPOX corresponds to a poly(p-hydroxy-benzyl alcohol (HBA)-oxalic acid) copolymer. To explore whether PVAX nanoparticles have improved therapeutic potential compared with HPOX nanoparticles, the inhibition of activity of caspase-3 and PARP-1 and expression of inflammation markers (TNF-α and MCP-1) by HPOX and PVAX was compared using hindlimb ischemia/reperfusion (I/R) injury in vivo.

In this study, HPOX was formulated with the ratio of HBA to 1,4-cyclohexanedimethanol of 20%, and PVAX was formulated with the ratio of vanillyl alcohol (VA) to 1,4-cyclohexanedimethanol of 20%.

Figure 52A:
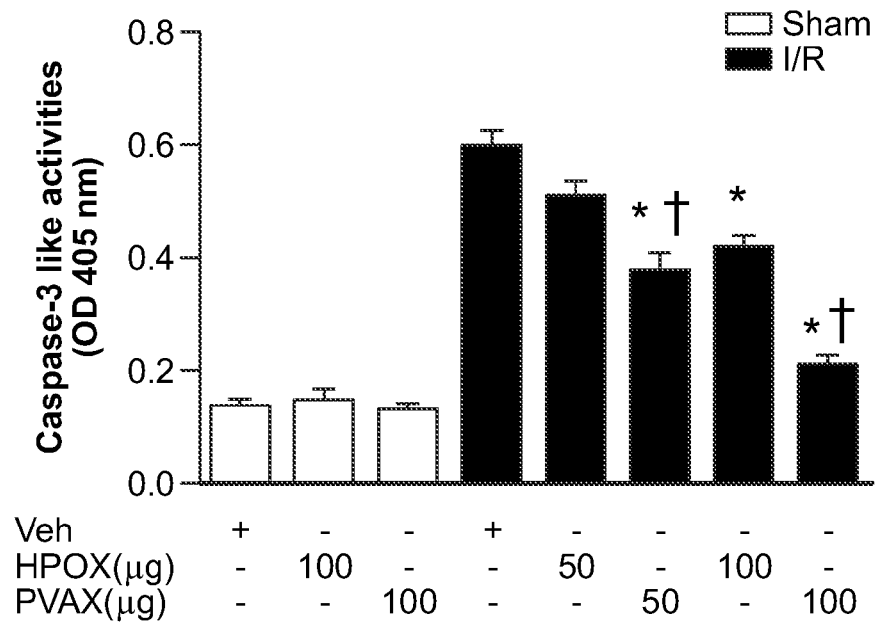
FIGS. 52A-52B, is a set of bar graphs illustrating the anti-apoptotic effect of PVAX and HPOX nanoparticles after hindlimb I/R.
Figure 52B:
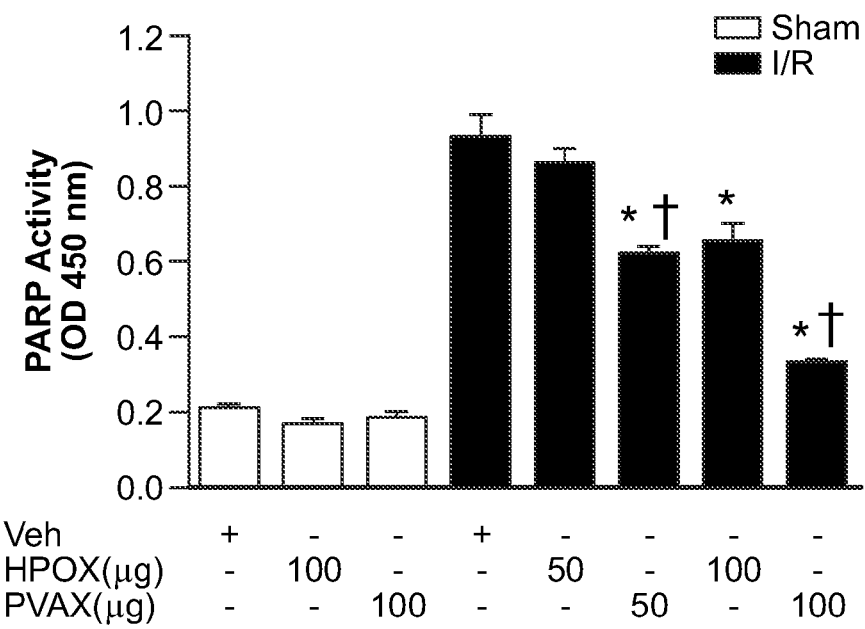

The concentration dependent inhibition of PARP-1 and caspase-3 activities in gastrocnemius muscle after hindlimb I/R using PVAX or HPOX nanoparticles was tested. 50 µg of HPOX did not show significant inhibition of PARP-1 and caspase-3 activation by I/R (FIGS. 52A-52B). However, there was significant inhibition of PARP-1 and caspase-3 activities at the same dose of PVAX. Similar effects were observed with the doses of 100 µg of HPOX and PVAX nanoparticles.

Figure 53A:
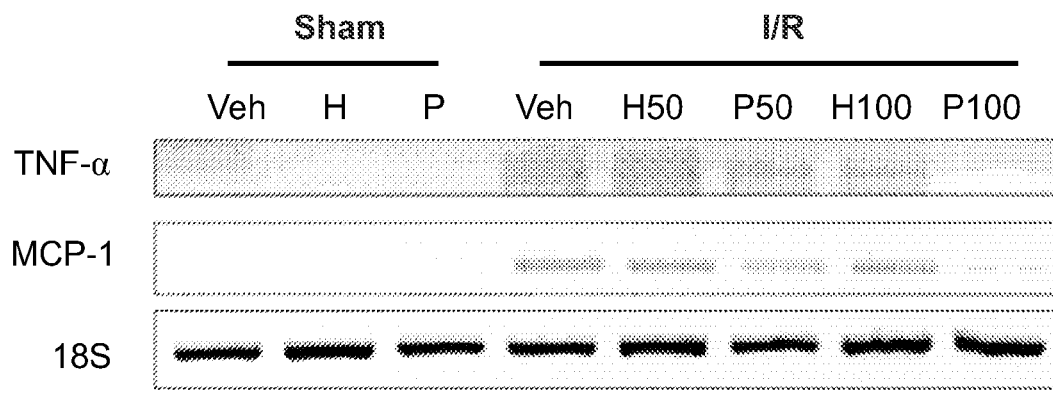
FIGS. 53A-53C, is a set of bar graphs illustrating the anti-inflammatory effect of PVAX and HPOX nanoparticles after hindlimb VR.
Figure 53B:
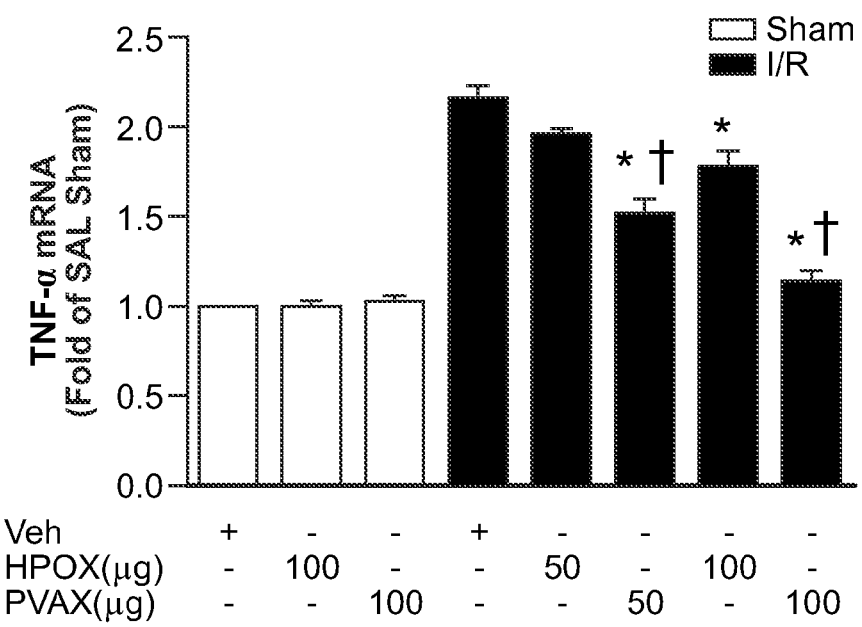
Figure 53C:
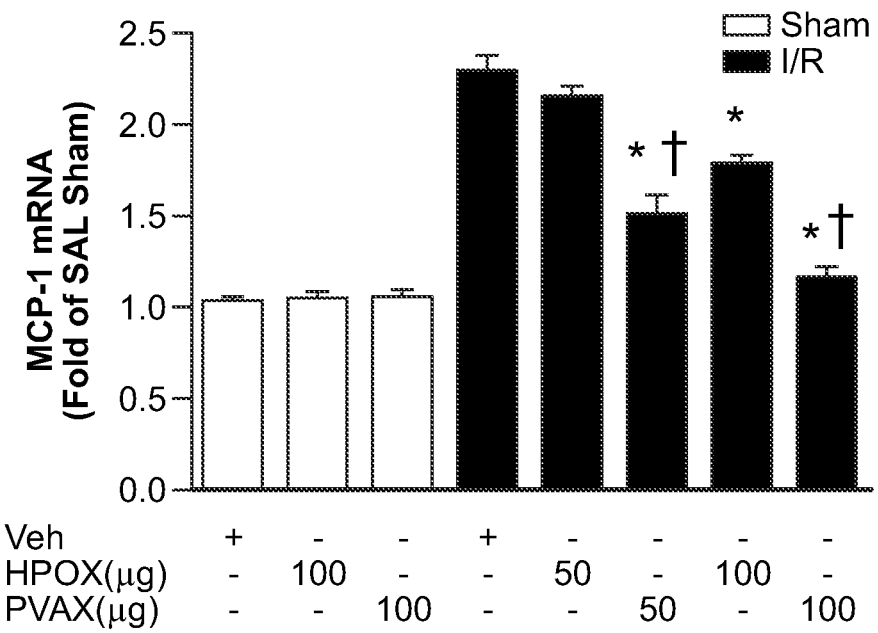

Moreover, PVAX nanoparticles after I/R at low dose (50 µg) significantly attenuated various markers of inflammation, such as TNF-α (tumor necrosis factor-alpha) and MCP-1 (monocyte chemotactic protein-1), but HPOX did not (FIGS. 53A-53C). These results indicated that PVAX nanoparticles have unexpected and significantly greater and anti-oxidant and anti-inflammatory properties compared with HPOX nanoparticles in I/R model in vivo.

Example 17: Comparison of PVAX at 20% and 60% Mole Fraction

An advantage of PVAX over HPOX is that PVAX is more stable and allows for greater loading (i.e., greater molar ratio) of vanillyl alcohol (VA) over 1,4-cyclohexanedimethanol (CHDM). For HPOX, loading greater than 20% HBA-CHDM was not feasible due to instability of the particles. However, PVAX allowed greater ratio of VA-CHDM (up to 60%), providing greater therapeutic effects without significant compromise of the stability.

To investigate how the therapeutic potential of PVAX 60 nanoparticles (60% ratio loading of VA-CHDM) compares to that of PVAX 20 nanoparticles (20% ratio loading of VA-CHDM), inhibition of activity of caspase-3 and PARP-1 and expression of inflammation marker (TNF-α) using hindlimb ischemia/reperfusion (I/R) injury in vivo were examined.

Figure 54A:
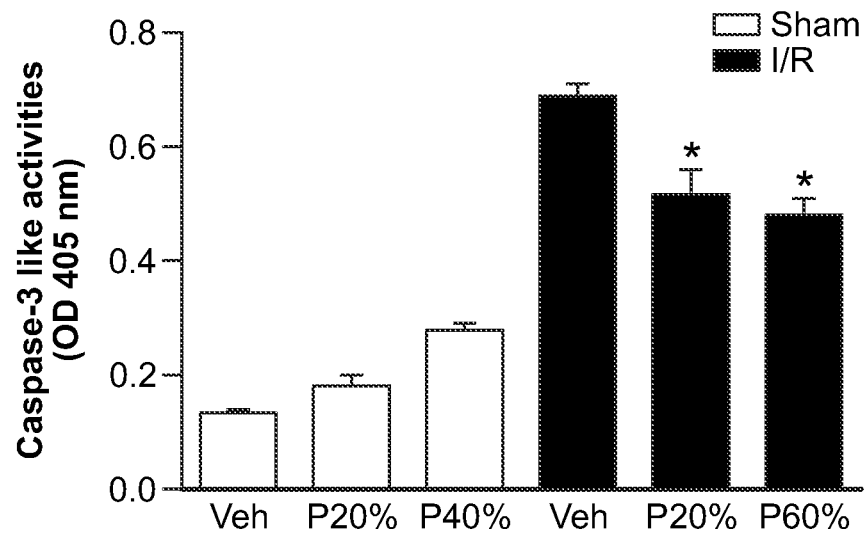
FIGS. 54A-54B, is a set of bar graphs illustrating the anti-apoptotic effect of PVAX 20 and PVAX 60 nanoparticles after hindlimb I/R.
Figure 54B:
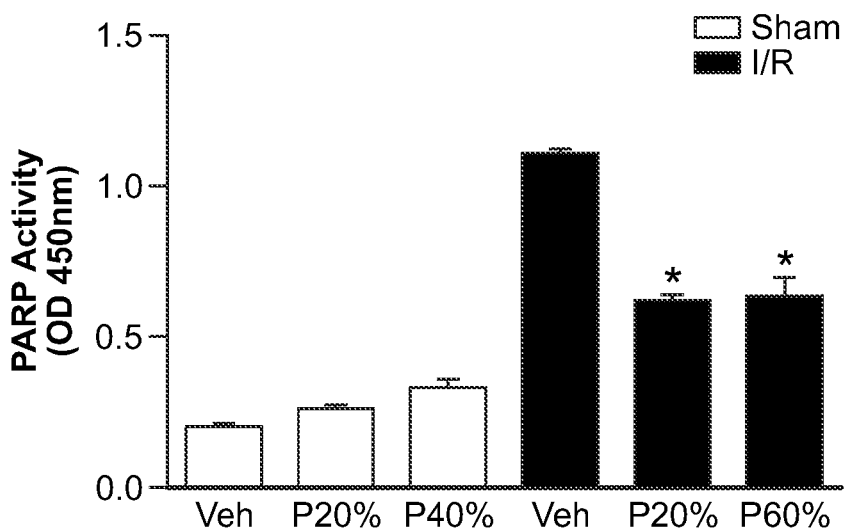
Figure 55:
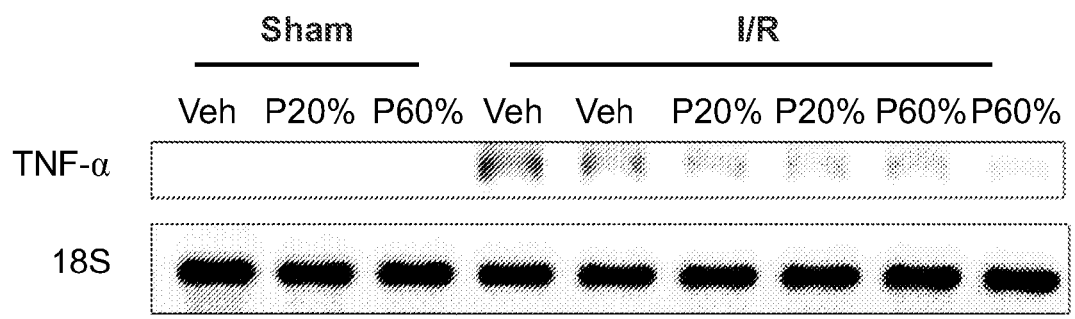
FIG. 55 is a gel photograph illustrating the anti-inflammatory effect of PVAX 20 and PVAX 60 nanoparticles after hindlimb FR, through imaging of mRNA expression of TNF-α. S=Saline, P20=PVAX20, P60=PVAX60, N=3-4/each group.

PVAX 20 (25 μg) and PVAX 60 (25 rig) at equal concentration significantly attenuated both activation of caspase-3 and PARP-1 (FIGS. 54A-54B) and expression of TNF-α, as compared with saline group after I/R. There was a discernible trend for greater protective effect with PVAX 60, but did not reach statistical significance (FIG. 55).

Example 18: Preparation of Pharmaceutical Compositions

Formulation examples for pharmaceutical compositions containing the PVAX microparticles of the present invention are herein described, but these formulation examples are not intended to limit the scope of the present invention.
Preparation of Powder Formulation
PVAX microparticles: 20 mg
Lactose: 100 mg
Talc: 10 mg
The above components were mixed and filled into an airtight bag, thereby preparing a powder formulation,
Preparation of Tablet Formulation
PVAX microparticles: 10 mg
Maize starch: 1100 mg
Lactose: 100 mg
Magnesium stearate: 2 mg
The above components were mixed and compressed into a tablet according to a conventional tablet preparation method, thereby preparing a tablet formulation,
Preparation of Capsule Formulation
PVAX microparticles: 10 mg
Crystalline cellulose: 3 mg
Lactose: 14.8 mg
Magnesium stearate: 0.2 mg
According to a conventional capsule preparation method, the above components were mixed and filled into a gelatin capsule, thereby preparing a capsule formulation.
Preparation of Injectable Formulation
PVAX microparticles: 10 mg
Mannitol: 180 mg
Sterile distilled water: 2,974 mg
$Na_2HPO_4*H_2O$: 26 mg
According to a conventional method, an injectable formulation was prepared by placing the above components into each ampule (2 ml).
Preparation of Liquid Formulation
PVAX microparticles: 20 mg
Isomerized sugar: 10 g
Mannitol: 5 g
Purified water: q.s.
According to a conventional method, a liquid formulation was prepared by dissolving each of the above components in purified water, adding a suitable amount of lemon fragrance thereto, mixing the above components with each other, adding purified water to the mixture to make a total volume of 100 ml, and then filling the solution into a brown bottle, followed by sterilization.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating or preventing a complication or condition associated with solid organ transplantation in a subject in need thereof, wherein the complication or condition is reperfusion injury, and the method comprises administering to the subject a therapeutically effective amount of a pharmaceutically acceptable composition comprising a microparticle as an active ingredient,
   wherein the microparticle comprises a copolymer comprising 2-(4-hydroxymethyl)-2-methoxy-phenoxy)-2-oxoacetic acid (VAOX) as a monomer, and
   wherein the copolymer undergoes at least partial degradation to release vanillyl alcohol within the body of the subject.

2. The method of claim 1, wherein the copolymer further comprises 2-((4-(hydroxymethyl)cyclohexyl)methoxy)-2-oxoacetic acid (CHDOX) as a monomer.

3. The method of claim 2, wherein the copolymer is represented by Formula (I):

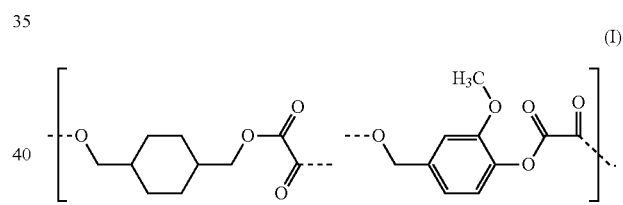

4. The method of claim 3, wherein in (I) the number of CHDOX monomers is an integer ranging from 10 to 50, and the number of VAOX monomers is an integer ranging from 5 to 30.

5. The method of claim 3, wherein in (I) the molar ratio of CHDOX to VAOX ranges from about 4:1 to about 2:3.

6. The method of claim 3, wherein the average molecular weight of (I) is about 10,000-20,000 Dalton.

7. The method of claim 1, wherein the microparticle has an average diameter ranging from about 200 nm to about 20 μm.

* * * * *